(12) United States Patent
Jia et al.

(10) Patent No.: US 11,760,756 B2
(45) Date of Patent: Sep. 19, 2023

(54) CRYSTALLINE FORM OF A PD-1/PD-L1 INHIBITOR

(71) Applicant: Incyte Corporation, Wilmington, DE (US)

(72) Inventors: Zhongjiang Jia, Kennett Square, PA (US); Shili Chen, Newark, DE (US); Mei Li, Newark, DE (US); Pingli Liu, Wilmington, DE (US); Yongchun Pan, Wilmington, DE (US); Yongzhong Wu, Glen Mills, PA (US); Jiacheng Zhou, Newark, DE (US)

(73) Assignee: Incyte Corporation, Wilmington, DE (US)

( * ) Notice: Subject to any disclaimer, the term of this patent is extended or adjusted under 35 U.S.C. 154(b) by 27 days.

(21) Appl. No.: 17/520,264

(22) Filed: Nov. 5, 2021

(65) Prior Publication Data
US 2022/0144832 A1 May 12, 2022

Related U.S. Application Data

(60) Provisional application No. 63/110,733, filed on Nov. 6, 2020.

(51) Int. Cl.
*C07D 471/04* (2006.01)

(52) U.S. Cl.
CPC ........ *C07D 471/04* (2013.01); *C07B 2200/13* (2013.01)

(58) Field of Classification Search
CPC .................................................... C07D 471/04
USPC ......................................................... 514/300
See application file for complete search history.

(56) References Cited

U.S. PATENT DOCUMENTS

| | | | |
|---|---|---|---|
| 3,272,781 A | 9/1966 | Goodrow | |
| 4,208,328 A | 6/1980 | Lavallee et al. | |
| 4,789,711 A | 12/1988 | Monnier et al. | |
| 5,077,164 A | 12/1991 | Ueda et al. | |
| 6,114,497 A | 9/2000 | Tada et al. | |
| 6,297,351 B1 | 10/2001 | Murayama et al. | |
| 6,372,907 B1 | 4/2002 | Lee et al. | |
| 6,521,618 B2 | 2/2003 | Boschelli et al. | |
| 6,867,200 B1 | 3/2005 | Allen et al. | |
| 7,320,989 B2 | 1/2008 | Anderson et al. | |
| 7,417,065 B2 | 8/2008 | Mi et al. | |
| 7,488,802 B2 | 2/2009 | Collins et al. | |
| 7,491,245 B2 | 2/2009 | Glenn et al. | |
| 7,691,870 B2 | 4/2010 | Buchstaller et al. | |
| 7,851,489 B2 | 12/2010 | Borzilleri et al. | |
| 7,943,743 B2 | 5/2011 | Korman et al. | |
| 8,008,449 B2 | 8/2011 | Korman et al. | |
| 8,163,743 B2 | 4/2012 | Baldwin et al. | |
| 8,168,757 B2 | 5/2012 | Finnefrock et al. | |
| 8,217,149 B2 | 7/2012 | Irving et al. | |
| 8,541,424 B2 | 9/2013 | DeGoey et al. | |
| 8,993,604 B2 | 3/2015 | Byrd et al. | |
| 9,085,576 B2 | 7/2015 | Minatti et al. | |
| 9,163,017 B2 | 10/2015 | DeGoey et al. | |
| 9,394,365 B1 | 7/2016 | Eisenbach-Schwartz et al. | |
| 9,540,322 B2 | 1/2017 | Jorgensen et al. | |
| 9,603,950 B1 | 3/2017 | Li et al. | |
| 9,611,261 B2 | 4/2017 | Minatti et al. | |
| 9,643,922 B2 | 5/2017 | Jorgensen et al. | |
| 10,017,520 B2 | 7/2018 | Koehler et al. | |
| 10,202,343 B2 | 2/2019 | Jorgensen et al. | |
| 10,308,644 B2 | 6/2019 | Wu et al. | |
| 10,618,916 B2 | 4/2020 | Wu et al. | |
| 10,669,271 B2 | 6/2020 | Wu et al. | |
| 10,793,565 B2 | 10/2020 | Wu et al. | |
| 10,800,768 B2 | 10/2020 | Wu et al. | |
| 10,806,785 B2 * | 10/2020 | Lu .................... | G01N 33/5026 |
| 10,906,920 B2 | 2/2021 | Wu et al. | |
| 11,124,511 B2 | 9/2021 | Wu et al. | |
| 11,339,149 B2 | 5/2022 | Wu et al. | |
| 11,401,279 B2 | 8/2022 | Li et al. | |
| 11,407,749 B2 | 8/2022 | Wu et al. | |
| 11,414,433 B2 | 8/2022 | Wu et al. | |
| 11,465,981 B2 | 10/2022 | Wu et al. | |
| 11,566,026 B2 | 1/2023 | Wu et al. | |
| 11,572,366 B2 | 2/2023 | Li et al. | |
| 11,608,337 B2 | 3/2023 | Li et al. | |
| 11,613,536 B2 | 3/2023 | Wu et al. | |
| 2002/0082266 A1 | 6/2002 | Gallant et al. | |
| 2003/0134843 A1 | 7/2003 | Lubisch et al. | |
| 2003/0191115 A1 | 10/2003 | Pinto et al. | |
| 2004/0018986 A1 | 1/2004 | Pitlik et al. | |

(Continued)

FOREIGN PATENT DOCUMENTS

| | | |
|---|---|---|
| CA | 2355249 | 6/2000 |
| CA | 3099994 | 11/2019 |

(Continued)

OTHER PUBLICATIONS

Indian Office Action in Indian Application No. 202017053661, dated Jun. 3, 2022, 5 pages.
Stahl et al., "Handbook of Pharmaceutical Salts: Properties, Selection, and Use," Wiley, 2002, p. 329-350.
Abdellaoui et al., "Palladium-catalyzed non-directed C-H bond arylation of difluorobenzenes and dichlorobenzenes bearing benzoxazole or benzothiazole," Catalysis Communications, 2015, 71:13-16.
Ahmed et al., "Enantioselective Polymerization of Epoxides Using Biaryl-Linked Bimetallic Cobalt Catalysts: A Mechanistic Study," J Am Chem Soc., 2013, 135(50):18901-18911.
Alverez et al., "Structure-Activity Study of Bioisosteric Trifluoromethyl and Pentafluorosulfanyl Indole Inhibitors of the AAA ATPase p97," ACS Med Chem., 2015, 6(12):1225-1230.

(Continued)

*Primary Examiner* — Niloofar Rahmani
(74) *Attorney, Agent, or Firm* — Fish & Richardson P.C.

(57) ABSTRACT

The present invention relates to crystalline forms of the PD-1/PD-L1 inhibitor (R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl) pyrrolidine-3-carboxylic acid, including methods of preparation thereof, and related synthetic intermediates, where the compound is useful in the treatment of various diseases including infectious diseases and cancer.

46 Claims, 19 Drawing Sheets

(56) References Cited

U.S. PATENT DOCUMENTS

| | | |
|---|---|---|
| 2004/0058938 A1 | 3/2004 | Cullmann et al. |
| 2004/0063963 A1 | 4/2004 | Ueno et al. |
| 2004/0082635 A1 | 4/2004 | Hashimoto et al. |
| 2004/0186114 A1 | 9/2004 | Cirillo et al. |
| 2004/0214040 A1 | 10/2004 | Lee et al. |
| 2005/0187230 A1 | 8/2005 | Ding et al. |
| 2005/0245536 A1 | 11/2005 | Hao et al. |
| 2005/0260126 A1 | 11/2005 | Kudo et al. |
| 2005/0288295 A1 | 12/2005 | Currie et al. |
| 2006/0004010 A1 | 1/2006 | Habashita et al. |
| 2006/0084650 A1 | 4/2006 | Dong et al. |
| 2006/0089362 A1 | 4/2006 | Seno et al. |
| 2006/0178367 A1 | 8/2006 | Currie et al. |
| 2006/0183746 A1 | 8/2006 | Currie et al. |
| 2006/0229337 A1 | 10/2006 | Brittelli et al. |
| 2006/0270686 A1 | 11/2006 | Kelly et al. |
| 2007/0099938 A1 | 5/2007 | Ohmoto et al. |
| 2007/0191395 A1 | 8/2007 | Kawakami et al. |
| 2008/0045536 A1 | 2/2008 | Vaccaro et al. |
| 2008/0139557 A1 | 6/2008 | Blomgren et al. |
| 2008/0153834 A1 | 6/2008 | Blomgren et al. |
| 2008/0280891 A1 | 11/2008 | Kelly et al. |
| 2009/0163545 A1 | 6/2009 | Goldfarb |
| 2009/0253735 A1 | 10/2009 | Almario-Garcia et al. |
| 2009/0281075 A1 | 11/2009 | Roughton et al. |
| 2009/0281120 A1 | 11/2009 | Nakai et al. |
| 2009/0304821 A1 | 12/2009 | Notoya et al. |
| 2010/0155712 A1 | 6/2010 | Kitamura |
| 2010/0160292 A1 | 6/2010 | Whitney et al. |
| 2010/0160303 A1 | 6/2010 | Liu et al. |
| 2010/0249151 A1 | 9/2010 | Klein et al. |
| 2010/0267775 A1 | 10/2010 | Negoro et al. |
| 2010/0267778 A1 | 10/2010 | Kusuda et al. |
| 2010/0273832 A1 | 10/2010 | Jung et al. |
| 2010/0292227 A1 | 11/2010 | Yoakim et al. |
| 2011/0053915 A1 | 3/2011 | Ivaschenko et al. |
| 2011/0062858 A1 | 3/2011 | Yersin et al. |
| 2011/0065699 A1 | 3/2011 | De Peretti et al. |
| 2011/0065700 A1 | 3/2011 | De Peretti et al. |
| 2011/0065745 A1 | 3/2011 | De Peretti et al. |
| 2011/0124640 A1 | 5/2011 | Liu et al. |
| 2011/0294781 A1 | 12/2011 | Yamamoto et al. |
| 2011/0301145 A1 | 12/2011 | Barbosa, Jr. et al. |
| 2012/0058996 A1 | 3/2012 | Liu et al. |
| 2012/0295884 A1 | 11/2012 | Altmann et al. |
| 2012/0323002 A1 | 12/2012 | Yamamoto et al. |
| 2012/0328569 A1 | 12/2012 | McComas et al. |
| 2013/0096118 A1 | 4/2013 | Liu et al. |
| 2013/0131063 A1 | 5/2013 | Castro et al. |
| 2013/0203741 A1 | 8/2013 | Suzuki et al. |
| 2013/0203747 A1 | 8/2013 | Yoakim et al. |
| 2013/0203754 A1 | 8/2013 | Yang et al. |
| 2013/0253011 A1 | 9/2013 | Jung et al. |
| 2014/0058097 A1 | 2/2014 | Kobayashi et al. |
| 2014/0088117 A1 | 3/2014 | Burch et al. |
| 2014/0128382 A1 | 5/2014 | Wu et al. |
| 2014/0243306 A1 | 8/2014 | Heng et al. |
| 2014/0275058 A1 | 9/2014 | Minatti et al. |
| 2014/0288094 A1 | 9/2014 | Bennett et al. |
| 2014/0378447 A1 | 12/2014 | Okano et al. |
| 2015/0005279 A1 | 1/2015 | Bonafoux et al. |
| 2015/0011751 A1 | 1/2015 | Kawakami et al. |
| 2015/0073024 A1 | 3/2015 | Sasikumar et al. |
| 2015/0181880 A1 | 7/2015 | Takahashi |
| 2015/0210680 A1 | 7/2015 | Kobayashi et al. |
| 2015/0232478 A1 | 8/2015 | Ishida et al. |
| 2015/0239868 A1 | 8/2015 | Pais et al. |
| 2015/0252011 A1 | 9/2015 | Minatti et al. |
| 2015/0258505 A1 | 9/2015 | Hironaka et al. |
| 2015/0291549 A1 | 10/2015 | Chupak et al. |
| 2015/0299227 A1 | 10/2015 | Wolkenberg et al. |
| 2015/0307465 A1 | 10/2015 | Scott et al. |
| 2015/0376172 A1 | 12/2015 | Guba et al. |
| 2016/0015690 A1 | 1/2016 | Babaoglu et al. |
| 2016/0046648 A1 | 2/2016 | Petrukhin et al. |
| 2016/0130251 A1 | 5/2016 | Graupe et al. |
| 2016/0194295 A1 | 7/2016 | Sasikumar et al. |
| 2016/0229816 A1 | 8/2016 | Sato et al. |
| 2016/0280695 A1 | 9/2016 | Minatti et al. |
| 2017/0107216 A1 | 4/2017 | Wu et al. |
| 2017/0145025 A1 | 5/2017 | Li et al. |
| 2017/0174671 A1 | 6/2017 | Wu et al. |
| 2017/0174679 A1 | 6/2017 | Lajkiewicz et al. |
| 2017/0304282 A1 | 10/2017 | Rocco et al. |
| 2017/0320875 A1 | 11/2017 | Li et al. |
| 2017/0342060 A1 | 11/2017 | Lu et al. |
| 2017/0362253 A1 | 12/2017 | Xiao et al. |
| 2018/0016260 A1 | 1/2018 | Yu et al. |
| 2018/0057486 A1 | 3/2018 | Wu et al. |
| 2018/0177784 A1 | 6/2018 | Wu et al. |
| 2018/0177870 A1 | 6/2018 | Liu et al. |
| 2018/0179179 A1 | 6/2018 | Wu et al. |
| 2018/0179197 A1 | 6/2018 | Wu et al. |
| 2018/0179201 A1 | 6/2018 | Wu et al. |
| 2018/0179202 A1 | 6/2018 | Wu et al. |
| 2018/0273519 A1 | 9/2018 | Wu et al. |
| 2019/0040082 A1 | 2/2019 | Xiao et al. |
| 2019/0062345 A1 | 2/2019 | Xiao et al. |
| 2019/0071439 A1 | 3/2019 | Li et al. |
| 2019/0144439 A1 | 5/2019 | Wu et al. |
| 2019/0202824 A1 | 7/2019 | Wu et al. |
| 2019/0225601 A1 | 7/2019 | Wu et al. |
| 2019/0270706 A1 | 9/2019 | Jorgensen et al. |
| 2019/0300524 A1 | 10/2019 | Wu et al. |
| 2019/0345170 A1 | 11/2019 | Wu et al. |
| 2020/0172533 A1 | 6/2020 | Wu et al. |
| 2020/0172541 A1 | 6/2020 | Li et al. |
| 2020/0181126 A1 | 6/2020 | Lu et al. |
| 2020/0255424 A1 | 8/2020 | Wu et al. |
| 2020/0277309 A1 | 9/2020 | Wu et al. |
| 2020/0283423 A1 | 9/2020 | Yu et al. |
| 2020/0325115 A1 | 10/2020 | Wu et al. |
| 2020/0397893 A1 | 12/2020 | Liu et al. |
| 2020/0407357 A1 | 12/2020 | Lajkiewicz et al. |
| 2021/0002276 A1 | 1/2021 | Wu et al. |
| 2021/0017164 A1 | 1/2021 | Lu et al. |
| 2021/0017175 A1 | 1/2021 | Li et al. |
| 2021/0040090 A1 | 2/2021 | Jia et al. |
| 2021/0094976 A1 | 4/2021 | Li et al. |
| 2021/0107900 A1 | 4/2021 | Wu et al. |
| 2021/0115025 A1 | 4/2021 | Yu et al. |
| 2021/0115068 A1 | 4/2021 | Wu et al. |
| 2021/0139511 A1 | 5/2021 | Jia et al. |
| 2021/0221819 A1 | 7/2021 | Li et al. |
| 2021/0317139 A1 | 10/2021 | Xiao et al. |
| 2021/0347771 A1 | 11/2021 | Wu et al. |
| 2021/0363137 A1 | 11/2021 | Wu et al. |
| 2021/0380584 A1 | 12/2021 | Wu et al. |
| 2022/0089588 A1 | 3/2022 | Wu et al. |
| 2022/0144830 A1 | 5/2022 | Zhou et al. |
| 2022/0144831 A1 | 5/2022 | Wang et al. |
| 2022/0193050 A1 | 6/2022 | Yang et al. |
| 2022/0194931 A1 | 6/2022 | Wu et al. |
| 2022/0213090 A1 | 7/2022 | Wu et al. |
| 2022/0340600 A1 | 10/2022 | Li et al. |
| 2022/0348594 A1 | 11/2022 | Wu et al. |
| 2023/0100875 A1 | 3/2023 | Lajkiewicz et al. |

FOREIGN PATENT DOCUMENTS

| | | |
|---|---|---|
| CL | 2018001531 | 7/2018 |
| CL | 2018003734 | 2/2019 |
| CL | 2018003701 | 4/2019 |
| CL | 2018003697 | 5/2019 |
| CL | 2019001744 | 10/2019 |
| CL | 2020002511 | 9/2020 |
| CN | 1344256 | 4/2002 |
| CN | 101891895 | 11/2010 |
| CN | 101910158 | 12/2010 |
| CN | 101993415 | 3/2011 |
| CN | 103933036 | 7/2014 |
| CN | 104045552 | 9/2014 |
| CN | 104211726 | 12/2014 |
| CN | 105164121 | 12/2015 |

(56) References Cited

FOREIGN PATENT DOCUMENTS

| | | |
|---|---|---|
| CN | 105705489 | 6/2016 |
| EP | 0361069 | 4/1990 |
| EP | 0644460 | 3/1995 |
| EP | 1505068 | 2/2005 |
| EP | 1644370 | 4/2006 |
| EP | 1942105 | 7/2008 |
| EP | 2233474 | 9/2010 |
| EP | 2402345 | 1/2012 |
| EP | 2871179 | 5/2015 |
| EP | 2824099 | 1/2018 |
| FR | 1425700 | 1/1966 |
| JP | H 10316853 | 12/1998 |
| JP | 2000128986 | 5/2000 |
| JP | 2000128987 | 5/2000 |
| JP | 2000212281 | 8/2000 |
| JP | 2001114893 | 4/2001 |
| JP | 2001163975 | 6/2001 |
| JP | 3461397 | 10/2003 |
| JP | 2003287634 | 10/2003 |
| JP | 2004059761 | 2/2004 |
| JP | 2004091369 | 3/2004 |
| JP | 2004294556 | 10/2004 |
| JP | 2005002330 | 1/2005 |
| JP | 2005248082 | 9/2005 |
| JP | 2005290301 | 10/2005 |
| JP | 2006290883 | 10/2006 |
| JP | 2008218327 | 9/2008 |
| JP | 2010202530 | 9/2010 |
| JP | 2010540452 | 12/2010 |
| JP | 2013084945 | 5/2013 |
| JP | 2014520866 | 8/2014 |
| JP | 2014532066 | 12/2014 |
| JP | 2015155397 | 8/2015 |
| JP | 2015193612 | 11/2015 |
| JP | 2016135778 | 7/2016 |
| JP | 2016532710 | 10/2016 |
| JP | 2019523231 | 8/2019 |
| JP | 2019530732 | 10/2019 |
| JP | 2020504737 | 2/2020 |
| JP | 2020504739 | 2/2020 |
| JP | 2020514271 | 5/2020 |
| JP | 6911031 | 7/2021 |
| KR | 1715090 | 3/2015 |
| KR | 1717601 | 12/2015 |
| KR | 1653560 | 2/2016 |
| TW | 103143948 | 12/2014 |
| TW | 201625527 | 7/2016 |
| WO | WO 98/27108 | 6/1998 |
| WO | WO 1999/018096 | 4/1999 |
| WO | WO 99/44992 | 9/1999 |
| WO | WO 00/35886 | 6/2000 |
| WO | WO 01/07409 | 2/2001 |
| WO | WO 2001/047883 | 7/2001 |
| WO | WO 01/74815 | 10/2001 |
| WO | WO 2002/000196 | 1/2002 |
| WO | WO 02/14321 | 2/2002 |
| WO | WO 02/48147 | 6/2002 |
| WO | WO 02/066477 | 8/2002 |
| WO | WO 02/071827 | 9/2002 |
| WO | WO 02/078700 | 10/2002 |
| WO | WO 02/083672 | 10/2002 |
| WO | WO 02/088124 | 11/2002 |
| WO | WO 03/022845 | 3/2003 |
| WO | WO 03/030901 | 4/2003 |
| WO | WO 03/031587 | 4/2003 |
| WO | WO 03/042402 | 5/2003 |
| WO | WO 2004/006906 | 1/2004 |
| WO | WO 2004/033454 | 4/2004 |
| WO | WO 2004/035588 | 4/2004 |
| WO | WO 2004/085385 | 10/2004 |
| WO | WO 2004/089940 | 10/2004 |
| WO | WO 2005/000833 | 1/2005 |
| WO | WO 2005/005429 | 1/2005 |
| WO | WO 2005/014543 | 2/2005 |
| WO | WO 2005/014599 | 2/2005 |
| WO | WO 2005/023761 | 3/2005 |
| WO | WO 2005/034869 | 4/2005 |
| WO | WO 2005/047290 | 5/2005 |
| WO | WO 2005/063710 | 7/2005 |
| WO | WO 2005/077948 | 8/2005 |
| WO | WO 2005/079802 | 9/2005 |
| WO | WO 2005/080316 | 9/2005 |
| WO | WO 2005/086808 | 9/2005 |
| WO | WO 2005/086904 | 9/2005 |
| WO | WO 2005/097751 | 10/2005 |
| WO | WO 2005/103022 | 11/2005 |
| WO | WO 2005/105798 | 11/2005 |
| WO | WO 2006/034317 | 3/2006 |
| WO | WO 2006/034337 | 3/2006 |
| WO | WO 2006/050803 | 5/2006 |
| WO | WO 2006/053121 | 5/2006 |
| WO | WO 2006/094235 | 9/2006 |
| WO | WO 2006/099075 | 9/2006 |
| WO | WO 2006/125101 | 11/2006 |
| WO | WO 2007/004954 | 1/2007 |
| WO | WO 2007/034282 | 3/2007 |
| WO | WO 2007/038314 | 4/2007 |
| WO | WO 2007/061764 | 5/2007 |
| WO | WO 2007/067711 | 6/2007 |
| WO | WO 2007/069565 | 6/2007 |
| WO | WO 2007/096764 | 8/2007 |
| WO | WO 2007/113226 | 10/2007 |
| WO | WO 2007/146712 | 12/2007 |
| WO | WO 2008/011560 | 1/2008 |
| WO | WO 2008/021745 | 2/2008 |
| WO | WO 2008/027812 | 3/2008 |
| WO | WO 2008/032171 | 3/2008 |
| WO | WO 2008/033854 | 3/2008 |
| WO | WO 2008/033857 | 3/2008 |
| WO | WO 2008/033858 | 3/2008 |
| WO | WO 2008/057254 | 5/2008 |
| WO | WO 2008/062182 | 5/2008 |
| WO | WO 2008/064317 | 5/2008 |
| WO | WO 2008/064318 | 5/2008 |
| WO | WO 2008/071944 | 6/2008 |
| WO | WO 2008/079965 | 7/2008 |
| WO | WO 2008/104077 | 9/2008 |
| WO | WO 2008/104278 | 9/2008 |
| WO | WO 2008/104279 | 9/2008 |
| WO | WO 2008/111299 | 9/2008 |
| WO | WO 2008/114002 | 9/2008 |
| WO | WO 2008/118122 | 10/2008 |
| WO | WO 2008/133274 | 11/2008 |
| WO | WO 2008/134553 | 11/2008 |
| WO | WO 2008/141249 | 11/2008 |
| WO | WO 2008/156712 | 12/2008 |
| WO | WO 2009/027733 | 3/2009 |
| WO | WO 2009/038759 | 3/2009 |
| WO | WO 2009/039397 | 3/2009 |
| WO | WO 2009/059162 | 5/2009 |
| WO | WO 2009/062059 | 5/2009 |
| WO | WO 2009/075830 | 6/2009 |
| WO | WO 2009/077197 | 6/2009 |
| WO | WO 2009/079683 | 7/2009 |
| WO | WO 2009/106539 | 9/2009 |
| WO | WO 2009/106597 | 9/2009 |
| WO | WO 2009/123986 | 10/2009 |
| WO | WO 2009/139576 | 11/2009 |
| WO | WO 2009/143156 | 11/2009 |
| WO | WO 2009/146358 | 12/2009 |
| WO | WO 2010/011837 | 1/2010 |
| WO | WO 2010/029950 | 3/2010 |
| WO | WO 2010/036959 | 4/2010 |
| WO | WO 2010/056875 | 5/2010 |
| WO | WO 2010/064020 | 6/2010 |
| WO | WO 2010/071885 | 6/2010 |
| WO | WO 2010/075376 | 7/2010 |
| WO | WO 2010/080474 | 7/2010 |
| WO | WO 2010/089411 | 8/2010 |
| WO | WO 2010/104306 | 9/2010 |
| WO | WO 2010/115736 | 10/2010 |
| WO | WO 2010/119264 | 10/2010 |
| WO | WO 2010/130034 | 11/2010 |
| WO | WO 2011/002635 | 1/2011 |

(56) References Cited

FOREIGN PATENT DOCUMENTS

| | | |
|---|---|---|
| WO | WO 2011/008709 | 1/2011 |
| WO | WO 2011/018170 | 2/2011 |
| WO | WO 2011/044181 | 4/2011 |
| WO | WO 2011/047129 | 4/2011 |
| WO | WO 2011/047319 | 4/2011 |
| WO | WO 2011/050245 | 4/2011 |
| WO | WO 2009/096202 | 5/2011 |
| WO | WO 2011/066342 | 6/2011 |
| WO | WO 2011/082400 | 7/2011 |
| WO | WO 2011/097607 | 8/2011 |
| WO | WO 2011/113606 | 9/2011 |
| WO | WO 2011/117264 | 9/2011 |
| WO | WO 2011/140202 | 11/2011 |
| WO | WO 2011/159877 | 12/2011 |
| WO | WO 2011/161699 | 12/2011 |
| WO | WO 2012/016133 | 2/2012 |
| WO | WO 2012/033735 | 3/2012 |
| WO | WO 2012/034363 | 3/2012 |
| WO | WO 2012/047856 | 4/2012 |
| WO | WO 2012/052730 | 4/2012 |
| WO | WO 2012/052745 | 4/2012 |
| WO | WO 2012/068406 | 5/2012 |
| WO | WO 2012/080376 | 6/2012 |
| WO | WO 2012/088411 | 6/2012 |
| WO | WO 2012/100342 | 8/2012 |
| WO | WO 2012/125886 | 9/2012 |
| WO | WO 2012/129562 | 9/2012 |
| WO | WO 2012/139425 | 10/2012 |
| WO | WO 2012/159565 | 11/2012 |
| WO | WO 2012/166951 | 12/2012 |
| WO | WO 2012/168733 | 12/2012 |
| WO | WO 2012/175991 | 12/2012 |
| WO | WO 2013/008095 | 1/2013 |
| WO | WO 2013/033901 | 3/2013 |
| WO | WO 2013/040528 | 3/2013 |
| WO | WO 2013/057650 | 4/2013 |
| WO | WO 2013/059594 | 4/2013 |
| WO | WO 2013/120040 | 8/2013 |
| WO | WO 2013/134113 | 9/2013 |
| WO | WO 2013/157021 | 10/2013 |
| WO | WO 2013/163404 | 10/2013 |
| WO | WO 2014/009295 | 1/2014 |
| WO | WO 2014/009296 | 1/2014 |
| WO | WO 2014/017087 | 1/2014 |
| WO | WO 2014/039595 | 3/2014 |
| WO | WO 2014/061693 | 4/2014 |
| WO | WO 2014/081878 | 5/2014 |
| WO | WO 2014/113388 | 7/2014 |
| WO | WO 2014/114532 | 7/2014 |
| WO | WO 2014/121085 | 8/2014 |
| WO | WO 2014/133046 | 9/2014 |
| WO | WO 2014/138484 | 9/2014 |
| WO | WO 2014/138791 | 9/2014 |
| WO | WO 2014/151634 | 9/2014 |
| WO | WO 2014/152536 | 9/2014 |
| WO | WO 2014/159959 | 10/2014 |
| WO | WO 2014/181287 | 11/2014 |
| WO | WO 2014/186035 | 11/2014 |
| WO | WO 2014/210255 | 12/2014 |
| WO | WO 2015/000715 | 1/2015 |
| WO | WO 2015/013635 | 1/2015 |
| WO | WO 2015/018940 | 2/2015 |
| WO | WO 2015/033299 | 3/2015 |
| WO | WO 2015/033301 | 3/2015 |
| WO | WO 2015/034820 | 3/2015 |
| WO | WO 2015/036927 | 3/2015 |
| WO | WO 2015/086498 | 6/2015 |
| WO | WO 2015/086499 | 6/2015 |
| WO | WO 2015/086502 | 6/2015 |
| WO | WO 2015/086512 | 6/2015 |
| WO | WO 2015/095337 | 6/2015 |
| WO | WO 2015/101622 | 7/2015 |
| WO | WO 2015/120364 | 8/2015 |
| WO | WO 2015/150097 | 10/2015 |
| WO | WO 2015/160641 | 10/2015 |
| WO | WO 2015/175678 | 11/2015 |
| WO | WO 2015/197028 | 12/2015 |
| WO | WO 2016/044604 | 3/2016 |
| WO | WO 2016/094688 | 6/2016 |
| WO | WO 2016/116525 | 7/2016 |
| WO | WO 2016/118404 | 7/2016 |
| WO | WO 2016/156282 | 10/2016 |
| WO | WO 2017/035405 | 3/2017 |
| WO | WO 2017/066227 | 4/2017 |
| WO | WO 2017/070089 | 4/2017 |
| WO | WO 2017/070320 | 4/2017 |
| WO | WO 2017/087777 | 5/2017 |
| WO | WO 2017/106634 | 6/2017 |
| WO | WO 2017/108569 | 6/2017 |
| WO | WO 2017/109041 | 6/2017 |
| WO | WO 2017/112617 | 6/2017 |
| WO | WO 2017/112730 | 6/2017 |
| WO | WO 2017/192961 | 11/2017 |
| WO | WO 2017/205464 | 11/2017 |
| WO | WO 2017/222976 | 12/2017 |
| WO | WO 2017/223239 | 12/2017 |
| WO | WO 2018/013789 | 1/2018 |
| WO | WO 2018/026971 | 2/2018 |
| WO | WO 2018/044783 | 3/2018 |
| WO | WO 2018/045084 | 3/2018 |
| WO | WO 2016/057500 | 4/2018 |
| WO | WO 2018/116259 | 6/2018 |
| WO | WO 2018/119036 | 6/2018 |
| WO | WO 2018/119221 | 6/2018 |
| WO | WO 2018/119224 | 6/2018 |
| WO | WO 2018/119236 | 6/2018 |
| WO | WO 2018/119263 | 6/2018 |
| WO | WO 2018/119266 | 6/2018 |
| WO | WO 2018/119286 | 6/2018 |
| WO | WO 2018/195321 | 10/2018 |
| WO | WO 2019/023575 | 1/2019 |
| WO | WO 2019/032547 | 2/2019 |
| WO | WO 2019/034172 | 2/2019 |
| WO | WO 2019/191707 | 10/2019 |
| WO | WO 2019/192506 | 10/2019 |
| WO | WO 2019/204609 | 10/2019 |
| WO | WO 2020/086556 | 4/2020 |
| WO | WO 2020/088357 | 5/2020 |
| WO | WO 2020/156323 | 8/2020 |
| WO | WO 2021/030162 | 2/2021 |

OTHER PUBLICATIONS

Amaya et al., "Synthesis of three-dimensionally arranged bis-biphenol ligand on hexaaryl benzene scaffold and its application for cross-pinacol coupling reaction," Tetrahedron Letters, 2011, 52(35):4567-4569.
Anyika et al., "Point-to-Axial Chirality Transfer—A New Probe for "Sensing" the Absolute Configurations of Monoamines," J Am Chem Soc., 2014, 136(2):550-553.
Argentina Office Action in Argentina Application No. 20170103634, dated Jan. 27, 2022, 7 pages.
Arkin et al., "Small-Molecule Inhibitors of Protein-Protein Interactions: Progressing toward the Reality," Chemistry & Biology, Sep. 2014, 21:1102-1114.
Arkin et al., "Small-Molecule Inhibitors of Protein-Protein Interactions: Progressing Towards the Dream," Nature Reviews, Apr. 2004, 3:301-317.
Artz et al., "Host-guest complexation. 28. Hemispherands with four self-organizing units," J Am Chem Soc., 1984, 106(7):2160-2171.
Atzrodt et al., "The Renaissance of H/D Exchange," Angew Chem Int Ed., 2007, 7744-7765.
Australian Office Action in Australian Application No. 2016358100, dated May 8, 2020, 5 pages.
Australian Notice of Allowance in Australian Application No. 2017382870, dated Mar. 15, 2022, 4 pages.
Azuma et al., "B7-H1 is a ubiquitous antiapoptotic receptor on cancer cells," Blood, Apr. 1, 2018, 111(7):3635-3643.
Barakat, "Do We Need Small Molecule Inhibitors for the Immune Checkpoints?" J. Pharma. Care Health Sys., 2014, 1(4):1000e119.
Barber et al., "Restoring function in exhausted CD8 T cells during chronic viral infection," Nature, Feb. 2006, 439:682-687.

(56) References Cited

OTHER PUBLICATIONS

Bastin et al., "Salt Selection and Optimisation for Pharmaceutical New Chemical Entities," Org Proc Res Dev., dated Jan. 1, 2000, pp. 4(5):427-435.
Bentley et al., "Antenna Biphenols: Development of Extended Wavelength Chiroptical Reporters," J Org Chem., 2016, 81(3):1185-1191.
Berg, "Modulation of Protein-Protein Interactions with Small Organic Molecules," Angew. Chem. Int. Ed., 2003, 42:2462-2481.
Berge et al., "Pharmaceutical Salts," J. Pharm. Sci., Jan. 1977, 66(1):1-19.
Blank et al., "PD-L1/B7H-1 Inhibits the Effector Phase of Tumor Rejection by T Cell Receptor (TCR) Transgenic CD8+ T Cells," Cancer Res., Feb. 2004, 64(3):1140-5.
Blom et al., "Optimizing Preparative LC-MS Configurations and Methods for Parallel Synthesis Purification", J. Combi. Chem., 2003, 5:670-83.
Blom et al., "Preparative LC-MS Purification: Improved Compound Specific Method Optimization", J, Combi. Chem., Nov. 2004, 6:874-883.
Blom, "Two-Pump At Column Dilution Configuration for Preparative LC-MS", K. Blom, J. Combi. Chem., 2002, 4:295-301.
Brazilian Office Action in Brazilian Application No. BR112018012756-6, dated Jan. 5, 2021, 6 pages.
Brass et al., "Radiation damage to 2-(2'-hydroxyphenyl)benzothiazoles," Radiation Physics and Chemistry, Jul. 1992, 41:379-387.
Buisman et al., "Chiral Cooperativity in Diastereomeric Diphosphite Ligands: Effects on the Rhodium-Catalyzed Enantioselective Hydroformylation of Styrene," Organometallics, 1997, 16(13):2929-2939.
Caira, "Crystalline Polymorphism of Organic Compounds," Topics in Current Chemistry, Jan. 1, 1998, 198:163-208.
Camara et al., "Multiple dermatofibromas: Dermoscopic patterns," Indian journal of dermatology, 2013, 58(3):243.
Carter et al., "PD-1:PD-L inhibitory pathway affects both CD4+ and CD8+ T cells and is overcome by IL-2," Eur. J. Immunol., 2002, 32(3):634-643.
Chang et al., "Blocking of the PD-1/PD-L1 Interaction by a d-Peptide Antagonist for Cancer Immunotherapy" Angew. Chem. Int. Ed., 2015, 26 pages; Supporting Information for 127(40):11926-11930.
Chang et al., "Blocking of the PD-1/PD-L1 Interaction by a d-Peptide Antagonist for Cancer Immunotherapy," Angew. Chem. Int. Ed., 2015, 127(40):11926-11930.
Chen et al., "Anti-PD-1/PD-L1 therapy of human cancer: past, present, and future," J. Clin Invest., Sep. 2015, 125(9):3384-3391.
Cheng et al., "Cancer-associated fibroblasts induce PDL1+ neutrophils through the IL6-STAT3 pathway that foster immune suppression in hepatocellular carcinoma," Cell Death and Disease, 2018, 9:422.
Cheng et al., "Recent Advances in Small Molecule Based Cancer Immunotherapy," Eur J Med Chem., 2018, 157:582-598.
Cheng et al., "Structure and Interactions of the Human Programmed Cell Death 1 Receptor," J. Bio. Chem., Apr. 2013, 288(17):11771-11785.
Cheng et al., "Synthetic connections to the aromatic directed metalation reaction. Iterative ortho metalation-cross coupling tactics for the construction of polyphenyls," Tetrahedron Letters, 1978, 28(43):5097-5098.
Chilean Office Action in Chilean Application No. 201801685, dated Aug. 20, 2019, 18 pages.
Chilean Office Action in Chilean Application No. 201803701, dated Nov. 22, 2019, 18 pages.
Chilean Office Action in Chilean Application No. 201901744, dated Apr. 14, 2020, 19 pages.
Chilean Office Action in Chilean Application No. 2922-2020, dated Dec. 8, 2021, 21 pages.
Chinese Office Action in Chinese Application No. 201680077700.8, dated Jul. 2, 2021, 23 pages.
Chinese Search Report in Chinese Application No. 201780049752.9, dated Dec. 28, 2020, 5 pages.

Clayden et al., "Conformational Preference and Remote (1,10) Stereocontrol in Biphenyl-2,2'-dicarboxamides," Org. Lett., 2001, 3(26):4133-4136.
Colombian Office Action in Colombian Application No. NC2019/0000386, dated Sep. 25, 2020, 18 pages.
Cram et al., "Host-guest complexation. 29. Expanded hemispherands," J Am Chem Soc., 1984, 106(11):6386-3292.
Cram et al., "Host-guest complexation. 32. Spherands composed of cyclic urea and anisyl units," J Am Chem Soc., 1984, 106(23):7150-7167.
Cram et al., "Host-guest complexation. 26. Cavitands composed of fluorobenzene units bonded in their 2,6-positions to form macrocycles," J Am Chem Soc., 1984, 106(3):695-701.
Cram et al., "Spherand hosts containing cyclic urea units," J Am Chem Soc., 1982, 104(24):6828-6830.
Curis, "Overview and Path for Growth," Aurigene Strategic Collaboration, Jan. 21, 2015, 13 slides.
Database accession No. 1478989-52-4 abstract, Nov. 22, 2013, 1 page.
Database Accession No. 1568738-04-4 abstract, Mar. 14, 2014, 1 page.
Database Accession No. 1580823-55-7 abstract, Apr. 6, 2014, 1 page.
Database Accession No. 1581556-71-9 abstract, Apr. 8, 2014, 1 page.
Database Accession No. 1590700-72-3 abstract, Apr. 27, 2014, 1 page.
Database accession No. 2013:447446 abstract, 2013, 1 page.
De Lucca et al., "Small Molecule Reversible Inhibitors of Bruton's Tyrosine Kinase (BTK): Structure-Activity Relationships Leading to the Identification of 7-(2-Hydroxypropan-2-yl)-4-[2-methyl-3-(4-oxo-3,4-dihydroquinazolin-3-yl)phenyl]-9H-carbazole-1-carboxamide (BMS-935177)," Journal of Medicinal Chemistry, 2016, 59(17):7915-7935.
Dhanunjayarao et al., "Synthesis and Optical Properties of Salicylaldimine-Based Diboron Complexes," Eur J Inorg Chem., 2014, 3:539-545.
Differding, "AUNP-12—A Novel Peptide Therapeutic Targeting PD-1 Immune Checkpoint Pathway for Cancer Immunotherapy—Structure Activity Relationships & Peptide / Peptidomimetic Analogs," Differding Consulting s.p.r.l. (Belgium), Feb. 26, 2014, 12 pages.
Dolan et al., "PD-1 Pathway Inhibitors: Changing the Landscape of Cancer Immunotherapy," Cancer Control, Jul. 2014, 21(3):231-237.
Domling et al., "Programmed Death-1: Therapeutic Success after More than 100 Years of Cancer Immunotherapy," Angew. Chem. Int. Ed., 2014, 53:2283-2288.
Dong et al., "Tumor-associated B7-H1 promotes T-cell apoptosis: a potential mechanism of immune evasion," Nature Medicine, Aug. 2002, 8(8):793-800.
Ecuador Opposition in Ecuador Application No. SENADI-2019-3773, dated Oct. 10, 2019, 29 pages.
Escarcega-Bobadilla et al., "A Recyclable Trinuclear Bifunctional Catalyst Derived from a Tetraoxo Bis-Zn(salphen) Metalloligand," Chemistry—A European Journal., 2013, 19(8):2641-2648.
Escarcega-Bobadilla et al., "Metal-directed assembly of chiral bis-Zn(II) Schiff base structures," Dalton Transactions, 2012, 41(32):9766-9772.
Escarcega-Bobadilla et al., "Versatile Switching in Substrate Topicity: Supramolecular Chirality Induction in Di- and Trinuclear Host Complexes," Chemistry—A European Journal, 2012:8(22):6805-6810.
Eurasian Office Action in Eurasian Application No. 201990074/28, dated Oct. 3, 2019, 5 pages.
European Communication in European Application No. 16805690.1, dated Jan. 22, 2020, 5 pages.
European Communication in European Application No. 16805690.1, dated Jul. 10, 2018, 6 pages.
European Communication in European Application No. 16805690.1, dated Nov. 5, 2020, 4 pages.
European Communication in European Application No. 17743174.9, dated Jan. 31, 2020, 5 pages.

(56) References Cited

OTHER PUBLICATIONS

European Communication in European Application No. 20202254.7, dated Apr. 1, 2022, 4 pages.
Fabris et al., "Central to Axial Transfer of Chirality in Menthone or Camphor-Derived 2,2'-Biphenols," J Org Chem., 1997, 62(21):7156-7164.
FDA Report, "22 Case Studies Where Phase 2 and Phase 3 Trials Had Divergent Results," U.S. Food and Drug Administration, Jan. 2017, 44 pages.
Francisco et al., "The PD-1 Pathway in Tolerance and Autoimmunity," Immunol. Rev., Jul. 2010, 236:219-242.
Freeman et al., "Engagement of the Pd-1 Immunoinhibitory Receptor by a Novel B7 Family Member Leads to Negative Regulation of Lymphocyte Activation," J. Exp. Med., Oct. 2000, 192(7):1027-34.
Freeman, "Structures of PD-1 with its ligands: Sideways and dancing cheek to cheek," PNAS, Jul. 2008, 105(30):10275-10276.
Freindorf, M., "Vibronic couplings in an excited state of hydrogen bond dimeric systems," Acta Physica Polonica, 1990, A78(6):825-839.
Gong et al., "Rhodium(I)-catalyzed regiospecific dimerization of aromatic acids: two direct C-H bond activations in water," Angewandte Chemie, 2015, 54(19):5718-5721.
Goswami et al., "A turn on ESIPT probe for rapid and ratiometric Iluorogenic detection of homocysteine and cysteine in water with live cell-imaging," Tetrahedron Letters, 2014, 55(2):490-494.
Gould et al. "Salt selection for basic drugs," Int J Pharma., 1986, 33(1-3):201-217.
Green et al., "Synthesis and investigation of the configurational stability of some dimethylammonium borate salts," J. Chem. Soc., Perkin Trans. 1, 2000, 24:4403-4408.
Greenwald et al., "The B7 Family Revisited," Annu. Rev. Immunol., 2005, 23:515-548.
Gu et al., "Undo the brake of tumour immune tolerance with antibodies, peptide mimetics and small molecule compounds targeting PD-1/PD-L1 checkpoint at different locations for acceleration of cytotoxic immunity to cancer cells," Clinical and Experimental Pharmacology and Physiology, 2019, 46(2):105-115.
Han et al., "Synthesis of binuclear phenoxyimino organoaluminum complexes and their use as the catalyst precursors for efficient ring-opening polymerisation of E-caprolactone," Dalton Transactions, 2013, 41:12346-12353.
Helgeson et al., "Host-guest complexation. 66. 18-Membered-ring spherands containing five anisyl groups," J Am Chem Soc., 1993, 1115(24):11506-11511.
Hilfiker "Relevance of Solid-state Properties for Pharmaceutical Products," Polymorphism in the Pharmaceutical Industry, Jan. 1, 2006, pp. 1-19.
Highlights Prescribing Information, "Opdivo," Revised Apr. 2019, 90 pages.
Highlights Prescribing Information, "Keytruda," Revised Feb. 2019, 66 pages.
Hu et al., "Novel highly active binuclear neutral nickel and palladium complexes as precatalysts for norbomene polymerization," Journal of Molecular Catalysis A: Chemical 253, 2006, 155-164.
Hu et al., "Syntheses and Ethylene Polymerization Behavior of Supported Salicylaldimine-Based Neutral Nickel(II) Catalysts," Organometallics, 2007, 26(10):2609-2615.
Hu et al., "Synthesis and Ethylene Polymerization Activity of a Novel, Highly Active Single-Component Binuclear Neutral Nickel(II) Catalyst," Organometallics, 2005, 24(11):2628-2632.
Huang et al, "The prognostic significance of PD-L1 in bladder cancer," Oncol. Rep., 2015, 33:3075-3084.
Huang et al., "Pharmacological treatment for keloids," Expert opinion on pharmacotherapy, 2013, 14(15):2087-2100.
Huddle et al., "Reactions of alkyl-lithium compounds with aryl halides," J Chem Soc., Perkin I, 1980, 12:2617-2625.
HuGEMM™ and HuCELL™ Models, "FactSheet," CrownBio, Oct. 2016, 8 pages.
Indian Office Action with Indian Application No. 201817026809, dated Apr. 29, 2020, 6 pages.
Indian Office Action with Indian Application No. 201917001998, dated Nov. 24, 2020, 7 pages.
Indian Office Action with Indian Application No. 201917028273, dated Feb. 15, 2021, 5 pages.
International Preliminary Report on Patentability in International Application No. PCT/US2017/041899, dated Jan. 15, 2019, 7 pages.
International Preliminary Report on Patentability in International Application No. PCT/US2016/057487, dated May 3, 2018, 7 pages.
International Preliminary Report on Patentability in International Application No. PCT/US2016/062730, dated May 31, 2018, 7 pages.
International Preliminary Report on Patentability in International Application No. PCT/US2016/067155, dated Jun. 19, 2018, 10 pages.
International Preliminary Report on Patentability in International Application No. PCT/US2016/067925, dated Jun. 26, 2018, 8 pages.
International Preliminary Report on Patentability in International Application No. PCT/US2017/031242, dated Nov. 6, 2018, 7 pages.
International Preliminary Report on Patentability in International Application No. PCT/US2017/034173, dated Nov. 27, 2018, 8 pages.
International Preliminary Report on Patentability in International Application No. PCT/US2017/038120, dated Dec. 25, 2018, 6 pages.
International Preliminary Report on Patentability in International Application No. PCT/US2017/048880, dated Mar. 5, 2019, 9 pages.
International Preliminary Report on Patentability in International Application No. PCT/US2017/067880, dated Jun. 25, 2019, 7 pages.
International Preliminary Report on Patentability in International Application No. PCT/US2017/067886, dated Jun. 25, 2019, 9 pages.
International Preliminary Report on Patentability in International Application No. PCT/US2017/067904, dated Jun. 25, 2019, 7 pages.
International Preliminary Report on Patentability in International Application No. PCT/US2017/067946, dated Jun. 25, 2019, 9 pages.
International Preliminary Report on Patentability in International Application No. PCT/US2017/067951, dated Jun. 25, 2019, 8 pages.
International Preliminary Report on Patentability in International Application No. PCT/US2017/067984, dated Jun. 25, 2019, 7 pages.
International Preliminary Report on Patentability in International Application No. PCT/US2019/025036, dated Oct. 15, 2020, 7 pages.
International Preliminary Report on Patentability in International Application No. PCT/US2019/031728, dated Nov. 17, 2020, 7 pages.
International Preliminary Report on Patentability in International Application No. PCT/US2020/045311, dated Feb. 17, 2022, 8 pages.
International Preliminary Report on Patentability in International Application No. PCT/US2020/053190, dated Apr. 5, 2022, 7 pages.
International Preliminary Report on Patentability in International Application No. PCT/US2020/059817, dated May 17, 2022, 12 pages.
International Search Report and Written Opinion in International Application No. PCT/US2016/057487, dated Dec. 8, 2016, 11 pages.
International Search Report and Written Opinion in International Application No. PCT/US2016/062730, dated Feb. 9, 2017, 12 pages.
International Search Report and Written Opinion in International Application No. PCT/US2016/067155, dated Apr. 24, 2017, 26 pages.
International Search Report and Written Opinion in International Application No. PCT/US2016/067925, dated Mar. 27, 2017, 13 pages.

(56) References Cited

OTHER PUBLICATIONS

International Search Report and Written Opinion in International Application No. PCT/US2017/031242, dated Jun. 20, 2017, 22 pages.
International Search Report and Written Opinion in International Application No. PCT/US2017/034173, dated Aug. 8, 2017, 15 pages.
International Search Report and Written Opinion in International Application No. PCT/US2017/038120, dated Aug. 1, 2017, 14 pages.
International Search Report and Written Opinion in International Application No. PCT/US2017/041899, dated Sep. 5, 2017, 12 pages.
International Search Report and Written Opinion in International Application No. PCT/US2017/048880, dated Oct. 23, 2017, 15 pages.
International Search Report and Written Opinion in International Application No. PCT/US2017/067880, dated Mar. 21, 2018, 13 pages.
International Search Report and Written Opinion in International Application No. PCT/US2017/067886, dated Mar. 23, 2018, 24 pages.
International Search Report and Written Opinion in International Application No. PCT/US2017/067904, dated Mar. 22, 2018, 14 pages.
International Search Report and Written Opinion in International Application No. PCT/US2017/067946, dated May 22, 2018, 16 pages.
International Search Report and Written Opinion in International Application No. PCT/US2017/067951, dated Mar. 27, 2018, 15 pages.
International Search Report and Written Opinion in International Application No. PCT/US2017/067984, dated Mar. 22, 2018, 14 pages.
International Search Report and Written Opinion in International Application No. PCT/US2019/025036, dated Jul. 3, 2019, 12 pages.
International Search Report and Written Opinion in International Application No. PCT/US2019/031728, dated Jun. 25, 2019, 12 pages.
International Search Report and Written Opinion in International Application No. PCT/US2020/045311, dated Oct. 2, 2020, 14 pages.
International Search Report and Written Opinion in International Application No. PCT/US2020/059817, dated Mar. 29, 2021, 19 pages.
International Search Report and Written Opinion in International Application No. PCT/US2020/053190, dated Jan. 29, 2021, 13 pages.
International Search Report and Written Opinion in International Application No. PCT/US2021/058338, dated Feb. 9, 2022, 15 pages.
International Search Report and Written Opinion in International Application No. PCT/US2021/058334, dated Apr. 25, 2022, 23 pages.
International Search Report and Written Opinion in International Application No. PCT/US2021/063965, dated Apr. 12, 2022, 20 pages.
International Search Report and Written Opinion in International Application No. PCT/US2021/058268, dated Apr. 21, 2022, 22 pages.
Invitation to Pay Fee's in International Application No. PCT/US2021/058268, dated Jan. 31, 2022, 16 pages.
Invitation to Pay Fee's in International Application No. PCT/US2021/058334, dated Feb. 3, 2022, 12 pages.
Israeli Office Action in Israeli Application No. 259,406, dated Mar. 11, 2020, 10 pages.
Israeli Office Action in Israeli Application No. 260,166, dated Jun. 2, 2020, 13 pages.
Israeli Office Action in Israeli Application No. 287,267, dated Feb. 15, 2022, 4 pages.
Iwai et al., "Involvement of PD-L1 on tumor cells in the escape from host immune system and tumor immunotherapy by PD-L1 blockade," PNAS, Sep. 2002, 99(19):12293-12297.
Japanese Office Action in Japanese Application No. 2018526213, dated Oct. 13, 2020, 10 pages.
Japanese Office Action in Japanese Application No. 2019-534122, dated Oct. 19, 2021, 10 pages.
Japanese Office Action in Japanese Application No. 2019-534195, dated Nov. 1, 2021, 8 pages.
Japanese Office Action in Japanese Application No. 2019-534196, dated Nov. 9, 2021, 8 pages.
Jiang et al., "Self-immobilizing binuclear neutral nickel catalyst for ethylene polymerization: Synthesis and catalytic studies," J Mol Cat., 2013, 380:139-143.
Kayal et al., "3,3'-Bis(triphenylsilyl)biphenoxide as a Sterically Hindered Ligand on Fe(II), Fe(III), and Cr(II)," Inorg Chem., 2002, 41(2):321-330.
Keir et al., "PD-1 and Its Ligands in Tolerance and Immunity," Annu. Rev. Immunol., 2008, 26:677-704.
Kerekes et al., "Aurora kinase inhibitors based on the imidazo[1,2-a]pyrazine core: fluorine and deuterium incorporation improve oral absorption and exposure," J Med Chem., 2011, 54(1):201-210.
Koch et al., "Nucleophilic reactions of pyridines and imidazoles with vinyl and aromatic halides," J Org Chem., 1993, 58(6):1409-1414.
Komiyama et al, "IL-17 Plays an Important Role in the Development of Experimental Autoimmune Encephalomyelitis," J. Immunol., Jul. 2006, 177:566-73.
Latchman et al., "PD-L2 is a second ligand for PD-1 and inhibits T cell activation," Nat. Immunol., Mar. 2001, 2(3):261-268.
Lazar-Molnar et al., "Crystal structure of the complex between programmed death-1 (PD-1) and its ligand PD-L2," PNAS, Jul. 2008, 105(30):10483-10488.
Legon'kova et al., "Interaction of o,o-dihalo o'-hydroxy azo compounds with metallic copper. II. Preparation of oligomeric azo compounds from monoazo compounds," Mosk Khim-Tekhnol Inst im Mendeleeva., 1968, 11(11):1281-1284 Machine Translation.
Legon'kova et al., "Interaction of o,o-dihalogeno o-hydroxy azo compounds with metallic copper," Trudy Instituta—Moskovskii Khimiko-Tekhnologicheskii Institut imeni D. I. Mendeleeva, 1965, 48:120-125 Machine Translation.
Lehtonen et al., "Comparison of quaternary methyl-, ethyl- and butylammonium hydroxides as alkylating reagents in pyrolysis-GC/MS studies of aquatic fulvic acid," Journal of Analytical and Applied Pyrolysis, 2003, 68-69:315-329.
Lexico.com, "Synonyms of Enhance," Oxford Dictionary, retrieved on Dec. 9, 2021, retrieved from URL <https://www.lexico.com/synonynns/enhance>, 4 pages.
Li et al., "A 3D Mesomeric Supramolecular Structure of a Cu(II) Coordination Polymer with 1,1'-Biphenyl-2,2',3,3'-tetracarboxylic Acid and 5,5'-Dimethyl-2,2'-bipyridine Ligands," J Inorg and Organomet Poly Mat., 2012, 22(6):1320-1324.
Li et al., "A Mini-Review for Cancer Immunotherapy: Molecular Understanding of PD-1/PD-L1 Pathway & Translational Blockade of Immune Checkpoints," Int. J. Mol. Soc., 2016, 17:1151, 22 pages.
Li et al., "Analysis of Receptor Tyrosine Kinase Internalization Using Flow Cytometry," Methods Mol. Biol., 2008, 457:305-317.
Li et al., "Asymmetric Alternating Copolymerization of Meso-epoxides and Cyclic Anhydrides: Efficient Access to Enantiopure Polyesters," J. Am. Chem. Soc., 2016, 138(36):11493-11496.
Li et al., "Discovery of peptide inhibitors targeting human programmed death 1 (PD-1) receptor," Oncotarget, Aug. 2016, 7(40):64967-64976.
Lin et al., "The PD-1/PD-L1 complex resembles the antigen-binding Fv domains of antibodies and T cell receptors," PNAS, Feb. 2008, 105(8):3011-3016.
Lipson et al., "From Discovery to Development: Blocking PD-1 and its Ligands," The Melanoma Letter, A Publication of The Skin Cancer Foundation, vol. 31, Summer 2013, 6 pages.

(56) References Cited

OTHER PUBLICATIONS

Liu et al., "Asymmetric Copolymerization of CO2 with meso-Epoxides Mediated by Dinuclear Cobalt(III) Complexes: Unprecedented Enantioselectivity and Activity," Angewandte Chemie, 2013, 52(44):11594-11598.
Liu et al., "Development of amino- and dimethylcarbamate-substituted resorcinol as programmed cell death-1 (PD-1) inhibitor," Eur J Pharm Sci, 2016, 88:50-58.
Mahoney et al., "The Next Immune-Checkpoint Inhibitors:PD-1/PD-L1 Blockade in Melanoma," Clin. Therapeutics, Nov. 2015, 37(4):761-782.
Maier et al., "Effects of the stationary phase and the solvent on the stereodynamics of biphep ligands quantified by dynamic three-column HPLC," Angewante Chemie, 2012, 51(12):2985-2988.
Manecke et al., "Preparation and properties of chelate-forming monomeric and polymeric Schiff bases derived from salicylaldehyde and 2,5-dihydroxyterephthalaldehyde. I," Makromolekulare Chemie, 1970, 133:61-82 English Abstract.
Manecke et al., "Preparation and properties of monomeric and polymeric Schiff bases derived from salicylaldehyde and 2,5-dihydroxyterephthalaldehyde. II. Electrical conductivity," Makromolekulare Chemie, 1972, 160:111-126 English Abstract.
Mexican Office Action in Mexican Application No. MX/a/2018/007774, dated Apr. 8, 2021, 5 pages.
Mexican Office Action in Mexican Application No. MX/a/2018/016273, dated Mar. 26, 2021, 5 pages.
Miyaura and Suzuki, "Palladium-Catalyzed Cross-Coupling Reactions of Organoboron Compounds," Chem Rev., 1995, 95:2457-2483.
Mochida et al., "Rhodinm-Catalyzed Regioselective Olefination Directed by a Carboxylic Group," J Org Chem, 2011, 76(9):3024-3033.
Moneta et al., "Boron templated synthesis of macrocyclic hosts containing convergent hydroxy or methoxy groups," Bulletin de la Societe Chimique de France, 1988, 6:995-1004 (English Abstract).
Nallasivam et al., "Development of Unimolecular Tetrakis(piperidin-4-ol) as a Ligand for Suzuki-Miyaura Cross-Coupling Reactions: Synthesis of Incrustoporin and Preclamol," 2015, Eur J Org Chem., 2015(16):3558-3567.
Nero et al., "Oncogenic protein interfaces: small molecules, big challenges," Nature Reviews, Apr. 2014, 14:248-262.
Nishimura et al., "Autoimmune Dilated Cardiomyopathy in PD-1 Receptor-Deficient Mice," Science, Jan. 2001, 291:319-322.
Nishimura et al., "Development of Lupus-like Autoimmune Diseases by Disruption of the PD-1 Gene Encoding an ITIM Motif-Carrying Immunoreceptor," Immunity, Aug. 1999, 11:141-151.
Nishimura et al., "PD-1: an inhibitory immunoreceptor involved in peripheral tolerance," TRENDS in Immunology, May 2001, 22(5):265-268.
Nishino et al., "Copper-Mediated C-H/C-H Biaryl Coupling of Benzoic Acid Derivatives and 1,3-Azoles," Angew. Chem. Int. Ed., 2013, 52:4457-4461.
Normand et al., "Dinuclear vs. mononuclear complexes: accelerated, metal-dependent ring-opening polymerization of lactide," Chem. Commun., 2013, 49(99):11692-11694.
Okazaki and Honjo, "The PD-1-PD-L pathway in immunological tolerance," Trends Immunol., Apr. 2006, 4:195-201.
Okazaki et al., "A rheostat for immune responses: the unique properties of PD-1 and their advantages for clinical application," Nature Immunology, Dec. 2013, 14(12):1212-1218.
Paek et al., "Chiral host. Attempted synthesis using McMurray reaction as a final ring closure method," Bulletin of the Korean Chemical Society, 1989, 10(6):572-577.
Paek et al.., "Facile syntheses and multi-orthofunctionalizations of tertiary benzamides," Bulletin of the Korean Chemical Society, 1993, 14(6):732-739.
Pardoll, "The blockade of immune checkpoints in cancer immunotherapy," Nature, Apr. 2012, 12:252-264.

Parry et al., "CTLA-4 and PD-1 Receptors Inhibit T-Cell Activation by Distinct Mechanisms," Mol. Cell. Biol., Nov. 2005, 25(21):9543-9553.
Parsons et al., "Directed ortho metalation reactions. Expedient synthesis of 3,3'-disubstituted 1,1'-bi-(2-phenols) (BIPOLS)," Tetrahedron Letters, 1994, 35(41):7537-7540.
Pascolutti et al., "Structure and Dynamics of PD-L1 and an Ultra-High-Affinity PD-1 Receptor Mutant," Structure, Oct. 2016, 24:1719-1728.
Paulini et al., "Orthogonal Multipolar Interactions in Structural Chemistry and Biology," Angew. Chem. Int. Ed., 2005, 44:1788-1805.
Pearson et al., "The formation of complexes between aza-derivatives of crown ethers and primary alkylammonium salts. Part 5. Chiral macrocyclic diamines," J. Chem. Soc., Perkin I, 1979, 12:3113-3126.
Pfeiffer et al., "Inner complex salts of the aldimine and azo series," Journal fuer Praktische Chemie, 1937, 149:217-296 Machine Translation.
Pierre et al., "Synthesis of a new macrobicyclic siderophoric host molecule with six converging phenolate groups," Angewandte Chemie, 1991, 103(1):75-76 Machine Translation.
Postow et al., "Immune Checkpoint Blockade in Cancer Therapy," J. Clinical Oncology, Jun. 2015, 33(17):1974-1982.
Press Release Archive, "Boehringer Ingelheim and Yale University collaborate to investigate novel immunotherapy targets across several therapeutic areas," Boehringer Ingelheim, Jan. 13, 2015, 2 pages.
Puehlhofer et al., "SASAPOS cascades of perfluorinated aromatic carboxylic acids: low-temperature decarboxylation triggered by electrostatic effects of polycationic ligand sets," Euro J of Org Chem., 2004, 5:1002-1007.
Punniyamurthy et al., "Enantiomerically pure bicyclo[3.3.1]nona-2,6-diene as the sole source of enantioselectivity in BIPHEP-Rh asymmetric hydrogenation," Chem Comm,, 2008, 41:5092-5094.
Qin et al., "The Diverse Function of PD-1/PD-L Pathway Beyond Cancer," Frontiers In Immunology, Oct. 2019, 10(2298):1-16.
Reck et al., "Pembrolizumab versus Chemotherapy for PD-L1-Positive Non-Small-Cell Lung Cancer," N Engl J Med., Nov. 10, 2016, 375(19):1823-1833.
Rowe et al., "Fumaric Acid" Handbook of pharmaceutical excipients, Jan. 1, 2009, pp. 276-277, 309-310, 393-396.
Sabatier et al., "Prognostic and predictive value of PDL1 expression in breast cancer," Oncotarget, Mar. 2015, 6(7):5449-5464.
Sharma et al., "Palladium-Catalyzed Decarboxylative Acylation of O-Phenyl Carbamates with Alpha-Oxocarboxylic Acids at Room Temperature," Advanced Synthesis & Catalysis, 2013, 355(4):667-672.
Sharpe et al, "The function of programmed cell death 1 and its ligands in regulating autoimmunity and infection," Nat. Immunol., Mar. 2007 8(3):239-245.
Sharpe et al., "The B7-CD28 Superfamily," Nature Reviews, Feb. 2002, 2:116-126.
Sorrell et al., "3,3'-Disubstituted 2,2'-biphenols. Synthesis of nonplanar, tetradentate chelating ligands," J Org Chem., 1985, 50(26):5765-5769.
STN Search Report dated Dec. 20, 2016, 117 pages.
STN Search Report dated Apr. 14, 2016, 79 pages.
STN Search Report dated Apr. 29, 2016, 69 pages.
STN Search Report dated Apr. 30, 2018, 8 pages.
STN Search Report dated Aug. 19, 2016, 23 pages.
STN Search Report dated Aug. 30, 2016, 4 pages.
STN Search Report dated Dec. 15, 2016, 4 pages.
STN Search Report dated Dec. 16, 2016, 25 pages.
STN Search Report dated Dec. 16, 2016, 4 pages.
STN Search Report dated Dec. 19, 2016, 11 pages.
STN Search Report dated Jul. 12, 2016, 4 pages.
STN Search Report dated Jun. 16, 2016, 8 pages.
STN Search Report dated Jun. 6, 2016, 115 pages.
STN Search Report dated Mar. 27, 2018, 4 pages.
STN Search Report dated May 24, 2016, 92 pages.
STN Search Report dated Sep. 12, 2016, 4 pages.
STN Search Report dated Sep. 12, 2016, 17 pages.

(56) References Cited

OTHER PUBLICATIONS

STN Search Report dated Sep. 2, 2016, 115 pages.
STN Search Report dated Sep. 27, 2017, 4 pages.
STN Search Report, dated May 1, 2016, 12 pages.
Storz, "Intellectual property issues of immune checkpoint inhibitors," mAbs, Jan. 2016, 8(1):10-26.
Suarez et al., "Inhibitors of TAM subfamily of tyrosine kinases: synthesis and biological evaluation," European Journal of Medicinal Chemistiy, 2013, 61:2-25.
Sumrit et al., "Aluminum complexes containing salicylbenzoxazole ligands and their application in the ring-opening polymerization of rac-lactide and ε-caprolactone," Dalton Transactions (2016), 45(22), 9250-9266.
Sun et al., "Studies on Synthesis and Properties of Some New Dibenzocyclobromonium," Chemical Journal of Chinese Universities, 1998, 19(12), 6 pages (English Abstract).
Sznol et al., "Antagonist Antibodies to PD-1 and B7-H1 (PD-L1) in the Treatment of Advanced Human Cancer," Clin Cancer Res., Mar. 1, 2013, 19(5):1021-1034.
Taiwan Office Action in Taiwan Application No. 105133530, dated Oct. 15, 2020, 8 pages.
Taiwan Office Action in Taiwan Application No. 105137807, dated Nov. 12, 2020, 12 pages.
Taiwan Office Action in Taiwan Application No. 105141804, dated Nov. 9, 2020, 9 pages.
Tang et al., "Facile synthesis of enantioenriched phenol-sulfoxides and their aluminum complexes," OrgBiomol Chem., 2016, 14(24):5580-5585.
Thiel et al., "Small-Molecule Stabilization of Protein-Protein Interactions: An Underestimated Concept in Drug Discovery?" Angew. Chem. Int. Ed., 2012, 51:2012-2018.
Tucker et al., "Host-guest complexation. 52. Bridged and chiral hemispheranda," J Org Chem., 1989, 54(23):5460-5482.
Ukraine Office Action in Ukraine Application No. a 2019 00525, dated Jan. 14, 2021, 11 pages.
Umau et al., "Directed ortho metalation. Suzuki cross coupling connections. Convenient regiospecific routes to functionalized m- and p-teraryls and m-quinquearyls," Tetrahedron Letters, 1992, 33(20):2773-2776.
Vaddepally et al., "Review of Indications of FDA-Approved Immune Checkpoint Inhibitors per NCCN Guidelines with the Level of Evidence," Cancers, 2020, 12(3):738.
Velcheti et al., "Programmed death-1/programmed death-1 ligand axis as a therapeutic target in oncology: current insights," Journal of Receptor Ligand and Channel Research, Dec. 2014, 8(23):1-7.
Wang et al., "The prognostic value of PD-L1 expression for non-small cell lung cancer patients: A meta-analysis," Eur. J. Surg. Oncol., 2015, 41:450-456.
Wang et al., "A binuclear Zn(II)-Zn(II) complex from a 2-hydroxybenzohydrazide-derived Schiff base for selective detection of pyrophosphate," Dalton Transactions, Oct. 2014, 43(37):14142-14146.
Wang et al., "Molecular Modeling and Functional Mapping of B7-H1 and B7-DC Uncouple Costimulatory Function from PD-1 Interaction," J. Exp. Med., Apr. 2013, 197(3):1083-1091.
Wei et al., "Strength of PD-1 signaling differentially affects T-cell effector functions," PNAS, Apr. 2013, E2480-E2489.
Weinmann, "Cancer Immunotherapy: Selected Targets and Small-Molecule Modulators," Chem. Med. Chem., 2016, 11:450-466.
Weiss et al., "Electrostatic activation of SNAr-reactivity by sulfonylonio substituents," Zeitschrift fuer Naturforschung, 2001, 56(12):1360-1368 English Abstract.
Weiss et al., "Electrostatics and color: Massive electrostatic perturbation of chromophores by ion cluster ligands," J Am Chem Soc., 2007, 129(3):547-553.
Weiss et al., "First-ever per(onio) substitution of benzene: the role of the counterion," Angewandte Chemie, 1995, 34(12):1319-1321.
Weiss et al., "Massive electrostatic effects on heteropolar C-C disconnections: Transforming a phenyl anion into a potent leaving group," Euro J Org Chem., 2005, 16:3530-3535.
Weiss et al., "Poly-onio substituted quinones as strong electron acceptors," Inst Org Chem., 1986, 98(10):925-926.
Weiss et al., "SASAPOS, not Sisyphus: highly efficient 20-step one-pot synthesis of a discrete organic-inorganic ion cluster with a porphyrin core," Angewandte Chemie International Edition, 2002, 41(20):3815-3817.
Weiss et al., "Syntheses and Reactions of Polycationically Substituted Azido- and Diazidobenzenes," Eur J Org Chem., Nov. 2007, 31:5270-5276.
Wells et al., "Reaching for high-hanging fmit in drug discovery at protein-protein interfaces," Nature, Dec. 2007, 450:1001-1009.
Wu et al., "Targeting the BACE1 Active Site Flap Leads to a Potent Inhibitor That Elicits Robust Brain AB Reduction in Rodents," ACS Medicinal Chemistry Letters, 2016, 7(3):271-276.
Wuts et al., "Protective Groups in Organic Synthesis," 4th Ed., 2007, 1111 pages.
www.medscape.com [online]. "The 'Family Business' Behind the Flurry of PD-1 Inhibitors," Sep. 10, 2014. [Retrieved on Jan. 29, 2015], Retrieved from the Internet: URL<http://www.medscape.com/viewarticle/831448_print>. 3 pages.
Xiong et al., "Biaryl-Bridged Salalen Ligands and Their Application in Titanium-Catalyzed Asymmetric Epoxidation of Olefins with Aqueous H2O2," Eur J Org Chem., 2011, 23:4289-4292.
Xu et al., "Design, synthesis and biological evaluation of deuterated nintedanib for improving pharmacokinetic properties," J Label Compd RadioPharm., Jun. 15, 2015, 58(7):308-312.
Xu et al., "Quantitative structure-activity relationship study on BTK inhibitors by modified multivariate adaptive regression spline and CoMSIA methods," SAR QSAR Environ Res., 2015, 26(4):279-300.
Yao et al., "PD-1 as an Immune Modulatory Receptor," Cancer J., 2014, 20(4):262-264.
Yin et al., "Strategies for Targeting Protein-Protein Interactions With Synthetic Agents," Angew. Chem. Int. Ed., 2005, 44:4130-4163.
Young et al., "Discovery of highly potent and selective Bruton's tyrosine kinase inhibitors: Pyridazinone analogs with improved metabolic stability," Bioorganic & Medicinal Chemistry Letters, 2016, 26(2):575-579.
Young et al., "Potent and selective Bruton's tyrosine kinase inhibitors: Discovery of GDC-0834," Bioorganic & Medicinal Chemistiy Letters, 2015, 25(6):1333-1337.
Zak et al., "Structural basis for small molecule targeting of the programmed death ligand 1 (PD-L1)" Oncotarget, Apr. 2016, 19 pages; Supplemental Material for 2016, 7(21):30323-30335.
Zak et al., "Structural basis for small molecule targeting of the programmed death ligand 1 (PD-L1)," Oncotarget, 2016, 7(21):30323-30335.
Zak et al., "Structure of the Complex of Human Programmed Death 1, PD-1, and Its Ligand PD-L1: with Supplemental Information," Structure, Dec. 2015, 23:2341-2348.
Zang et al., "Four 2D metal-organic networks incorporating Cd-cluster SUBs: hydrothermal synthesis, structures and photoluminescent properties," CrystEngComm, 2009, 11(1):122-129.
Zarganes-Tzitzikas, "Inhibitors of programmed cell death 1 (PD-1): a patent review (2010-2015)," Expert Opinion on Therapeutic Patents, Sep. 19, 2016, 26(9):973-977.
Zhan et al., "From monoclonal antibodies to small molecules: the development of inhibitors targeting the PD-1/PD-L1 pathway," Drug Discovery Today, Apr. 2016, 10 pages.
Zhang et al., "Biaryl-Based Macrocyclic and Polymeric Chiral (Salophen)Ni(II) Complexes: Synthesis and Spectroscopic Study," J Org Chem., 2001, 66(2):481-487.
Zhang et al., "Electrospray mass spectrum of a per(onio)-substituted benzene: retention of Coulombic charge upon collisionally activated decomposition," J Am Soc. Mass. Spectrom., 1998, 9(1):15-20.
Zhang et al., "Non-symmetrical diarylcarboxylic acids via rhodium(I)-catalyzed regiospecific crossdehydrogenation coupling of aromatic acids: twofold direct C-H bond activations in water," RSC Advances, 2016, 6(64):91617-91620.
Zhang et al., "Structural and Functional Analysis of the Costimulatory Receptor Programmed Death-1," Immunity, Mar. 2004, 20:337-347.

(56) References Cited

OTHER PUBLICATIONS

Zhao et al., "Design, synthesis and organocatalysis of 2,2'-biphenol-based prolinamide organocatalysts in the asymmetric direct aldol reaction in water," Synlett, 2013, 24(20):2743-2747.

Otter et al., "The human papillomavirus as a common pathogen in oropharyngeal, anal and cervical cancers," Clin Oncol (R Coll Radiol), Feb. 2019, 31(2):81-90.

Rowe et al., "Fumaric Acid" Handbook of pharmaceutical excipients, Jan. 1, 2009, pp. 276-277, 318-321, 663-666.

\* cited by examiner

CRYSTALLINE FORM OF A PD-1/PD-L1 INHIBITOR

CROSS-REFERENCE TO RELATED APPLICATIONS

The present application claims the benefit of U.S. Provisional Application No. 63/110,733, filed Nov. 6, 2020, which is incorporated herein by reference in its entirety.

FIELD OF THE INVENTION

This application relates to crystalline forms of PD-1/PD-L1 inhibitor (R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl) pyrrolidine-3-carboxylic acid, including methods of preparation thereof, and related synthetic intermediates, where the compound is useful in the treatment of various diseases including infectious diseases and cancer.

BACKGROUND OF THE INVENTION

The immune system plays an important role in controlling and eradicating diseases such as cancer. However, cancer cells often develop strategies to evade or to suppress the immune system in order to favor their growth. One such mechanism is altering the expression of co-stimulatory and co-inhibitory molecules expressed on immune cells (Postow et al, J. Clinical Oncology 2015, 1-9). Blocking the signaling of an inhibitory immune checkpoint, such as PD-1, has proven to be a promising and effective treatment modality.

Programmed cell death-1 (PD-1), also known as CD279, is a cell surface receptor expressed on activated T cells, natural killer T cells, B cells, and macrophages (Greenwald et al, Annu. Rev. Immunol 2005, 23:515-548; Okazaki and Honjo, Trends Immunol 2006, (4):195-201). It functions as an intrinsic negative feedback system to prevent the activation of T-cells, which in turn reduces autoimmunity and promotes self-tolerance. In addition, PD-1 is also known to play a critical role in the suppression of antigen-specific T cell response in diseases like cancer and viral infection (Sharpe et al, Nat Immunol 2007 8, 239-245; Postow et al, J. Clinical Oncol 2015, 1-9).

The structure of PD-1 consists of an extracellular immunoglobulin variable-like domain followed by a transmembrane region and an intracellular domain (Parry et al, Mol Cell Biol 2005, 9543-9553). The intracellular domain contains two phosphorylation sites located in an immunoreceptor tyrosine-based inhibitory motif and an immunoreceptor tyrosine-based switch motif, which suggests that PD-1 negatively regulates T cell receptor-mediated signals. PD-1 has two ligands, PD-L1 and PD-L2 (Parry et al, Mol Cell Biol 2005, 9543-9553; Latchman et al, Nat Immunol 2001, 2, 261-268), and they differ in their expression patterns. PD-L1 protein is upregulated on macrophages and dendritic cells in response to lipopolysaccharide and GM-CSF treatment, and on T cells and B cells upon T cell receptor and B cell receptor signaling. PD-L1 is also highly expressed on almost all tumor cells, and the expression is further increased after IFN-γ treatment (Iwai et al, PNAS 2002, 99(19):12293-7; Blank et al, Cancer Res 2004, 64(3):1140-5). In fact, tumor PD-L1 expression status has been shown to be prognostic in multiple tumor types (Wang et al, Eur J Surg Oncol 2015; Huang et al, Oncol Rep 2015; Sabatier et al, Oncotarget 2015, 6(7): 5449-5464). PD-L2 expression, in contrast, is more restricted and is expressed mainly by dendritic cells (Nakae et al, J Immunol 2006, 177:566-73). Ligation of PD-1 with its ligands PD-L1 and PD-L2 on T cells delivers a signal that inhibits IL-2 and IFN-γ production, as well as cell proliferation induced upon T cell receptor activation (Carter et al, Eur J Immunol 2002, 32(3):634-43; Freeman et al, J Exp Med 2000, 192(7):1027-34). The mechanism involves recruitment of SHP-2 or SHP-1 phosphatases to inhibit T cell receptor signaling such as Syk and Lck phosphorylation (Sharpe et al, Nat Immunol 2007, 8, 239-245). Activation of the PD-1 signaling axis also attenuates PKC-θ activation loop phosphorylation, which is necessary for the activation of NF-κB and AP1 pathways, and for cytokine production such as IL-2, IFN-γ and TNF (Sharpe et al, Nat Immunol 2007, 8, 239-245; Carter et al, Eur J Immunol 2002, 32(3):634-43; Freeman et al, J Exp Med 2000, 192(7):1027-34).

Several lines of evidence from preclinical animal studies indicate that PD-1 and its ligands negatively regulate immune responses. PD-1-deficient mice have been shown to develop lupus-like glomerulonephritis and dilated cardiomyopathy (Nishimura et al, Immunity 1999, 11:141-151; Nishimura et al, Science 2001, 291:319-322). Using an LCMV model of chronic infection, it has been shown that PD-1/PD-L1 interaction inhibits activation, expansion and acquisition of effector functions of virus-specific CD8 T cells (Barber et al, Nature 2006, 439, 682-7). Together, these data support the development of a therapeutic approach to block the PD-1-mediated inhibitory signaling cascade in order to augment or "rescue" T cell response. Accordingly, there is a need for new compounds and salts that block PD-1/PD-L1 protein/protein interaction. For the development of a drug, it is typically advantageous to employ a form of the drug having desirable properties with respect to its preparation, purification, reproducibility, stability, bioavailability, and other characteristics. Accordingly, the solid crystalline forms of the compound provided herein help satisfy the ongoing need for the development of PD-1/PD-L1 inhibitors for the treatment of diseases.

SUMMARY OF THE INVENTION

The present disclosure is directed to crystalline forms of (R)-1-((7-cyano-2-(3'-(3-(((R)-3-hydroxypyrrolidin-1-yl) methyl)-1,7-naphthyridin-8-ylamino)-2,2'-dimethylbiphenyl-3-yl)benzo[d]oxazol-5-yl)methyl)pyrrolidine-3-carboxylic acid.

The present disclosure is further directed to pharmaceutical compositions comprising a crystalline form described herein, and at least one pharmaceutically acceptable carrier or excipient. The present disclosure is further directed to solid dosage forms comprising the pharmaceutical compositions.

The present disclosure is further directed to a method of inhibiting PD-1/PD-L1 interaction comprising administering to a patient the crystalline forms described herein. The present disclosure also provides uses of the crystalline forms described herein in the manufacture of a medicament for use in inhibiting PD-1/PD-L1 interaction. The present disclosure also provides the crystalline forms described herein for use in inhibiting PD-1/PD-L1 interaction.

The present disclosure is further directed to treating a disease or disorder associated with inhibition of PD-1/PD-L1 interaction comprising administering to a patient the crystalline forms described herein. The present disclosure also provides uses of the crystalline forms described herein in the manufacture of a medicament for use in treating a disease or disorder associated with inhibition of PD-1/PD-L1 interaction. The present disclosure also provides the crystalline forms described herein for use in treating a disease or disorder associated with inhibition of PD-1/PD-L1 interaction.

The present disclosure is further directed to enhancing, stimulating and/or increasing the immune response in a patient comprising administering to a patient the crystalline forms described herein. The present disclosure also provides uses of the crystalline forms described herein in the manufacture of a medicament for use in enhancing, stimulating and/or increasing the immune response in a patient. The present disclosure also provides the crystalline forms described herein for use in enhancing, stimulating and/or increasing the immune response in a patient.

The present invention is further directed to processes for preparing solid forms (e.g., crystalline and amorphous forms) described herein.

The details of one or more embodiments are set forth in the description below. Other features, objects, and advantages will be apparent from the description and from the claims.

DETAILED DESCRIPTION

Figure 1:
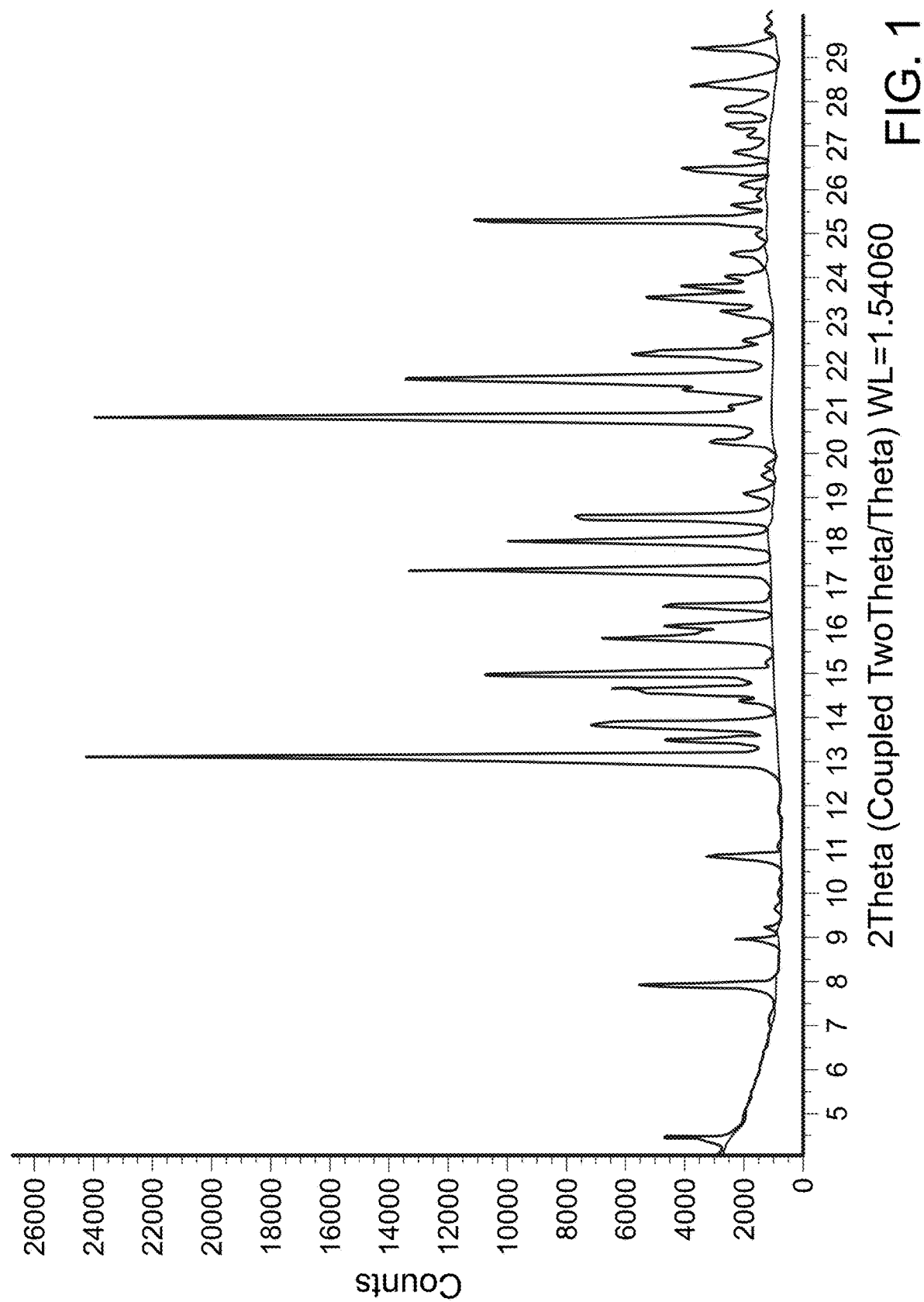
FIG. 1 shows an XRPD pattern of the crystalline Form I of Compound 1.

The present disclosure is directed to, inter alia, a crystalline form of (R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid (Compound 1).

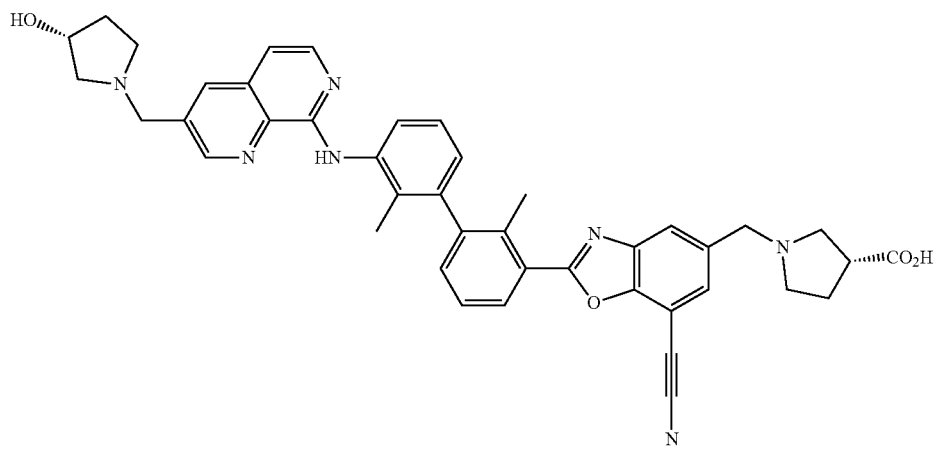

Compound 1

Compound 1 is described in U.S. Pat. No. 10,308,644, the entirety of which is incorporated herein by reference.

In some embodiments, the present disclosure is directed to a crystalline form of Compound 1:

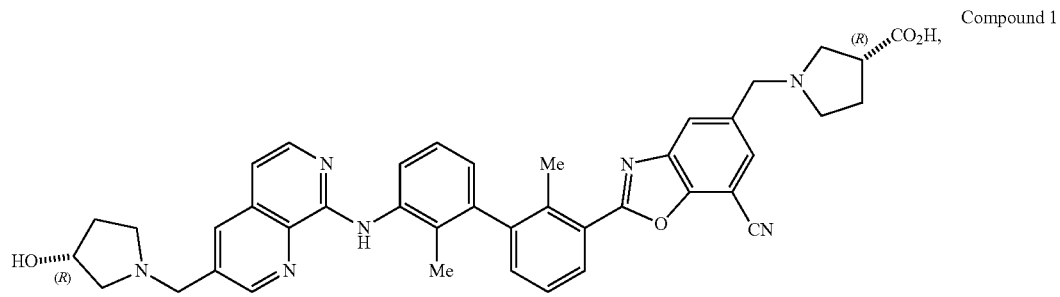

Compound 1 or a solvate thereof. In some embodiments, the form is non-solvated. In some embodiments, the form is a solvate. In some embodiments, the form is a tetrahydrofuran solvate.

Form I of Compound 1

In some embodiments, the crystalline form is Form I. In some embodiments, Form I is non-solvated. In some embodiments, the form has at least one XRPD peaks, in terms of 2-theta (±0.2 degrees), selected from 4.5, 7.9, 10.8, 13.1, 15.0, 17.3, 18.0, 20.8, 21.7, and 25.3 degrees. In some embodiments, the form has at least two XRPD peaks, in terms of 2-theta (±0.2 degrees), selected from 4.5, 7.9, 10.8, 13.1, 15.0, 17.3, 18.0, 20.8, 21.7, and 25.3 degrees. In some embodiments, the form has at least three XRPD peaks, in terms of 2-theta (±0.2 degrees), selected from 4.5, 7.9, 10.8, 13.1, 15.0, 17.3, 18.0, 20.8, 21.7, and 25.3 degrees. In some embodiments, the form has at least four XRPD peaks, in terms of 2-theta (±0.2 degrees), selected from 4.5, 7.9, 10.8, 13.1, 15.0, 17.3, 18.0, 20.8, 21.7, and 25.3 degrees. In some embodiments, the form has at least five XRPD peaks, in terms of 2-theta (±0.2 degrees), selected from 4.5, 7.9, 10.8, 13.1, 15.0, 17.3, 18.0, 20.8, 21.7, and 25.3 degrees. In some embodiments, the form has characteristic XRPD peaks, in terms of 2-theta (±0.2 degrees), at 4.5, 7.9, 10.8, 13.1, 15.0, 17.3, 18.0, 20.8, 21.7, and 25.3 degrees. In some embodiments, the form has at least one XRPD peaks, in terms of 2-theta (±0.2 degrees), selected from 4.5, 7.9, 10.8, 13.1, 15.0, 17.3, and 20.8 degrees. In some embodiments, the form has at least two XRPD peaks, in terms of 2-theta (±0.2 degrees), selected from 4.5, 7.9, 10.8, 13.1, 15.0, 17.3, and 20.8 degrees. In some embodiments, the form has at least three XRPD peaks, in terms of 2-theta (±0.2 degrees), selected from 4.5, 7.9, 10.8, 13.1, 15.0, 17.3, and 20.8 degrees. In some embodiments, the form has at least four XRPD peaks, in terms of 2-theta (±0.2 degrees), selected from 4.5, 7.9, 10.8, 13.1, 15.0, 17.3, and 20.8 degrees. In some embodiments, the form has at least five XRPD peaks, in terms of 2-theta (±0.2 degrees), selected from 4.5, 7.9, 10.8, 13.1, 15.0, 17.3, and 20.8 degrees. In some embodiments, the form has characteristic XRPD peaks, in terms of 2-theta (±0.2 degrees), at 4.5, 7.9, 10.8, 13.1, 15.0, 17.3, and 20.8 degrees.

In some embodiments, the form has at least one XRPD peaks, in terms of 2-theta (±0.2 degrees), selected from 4.5, 7.9, 9.0, 10.8, 13.1, 13.5, 13.8, 14.7, 15.0, 15.8, 16.1, 16.5, 17.3, 18.0, 18.5, 19.1, 20.8, 21.7, and 25.3 degrees. In some embodiments, the form has at least two XRPD peaks, in terms of 2-theta (±0.2 degrees), selected from 4.5, 7.9, 9.0, 10.8, 13.1, 13.5, 13.8, 14.7, 15.0, 15.8, 16.1, 16.5, 17.3, 18.0, 18.5, 19.1, 20.8, 21.7, and 25.3 degrees. In some embodiments, the form has at least three XRPD peaks, in terms of 2-theta (±0.2 degrees), selected from 4.5, 7.9, 9.0, 10.8, 13.1, 13.5, 13.8, 14.7, 15.0, 15.8, 16.1, 16.5, 17.3, 18.0, 18.5, 19.1, 20.8, 21.7, and 25.3 degrees. In some embodiments, the form has at least four XRPD peaks, in terms of 2-theta (±0.2 degrees), selected from 4.5, 7.9, 9.0, 10.8, 13.1, 13.5, 13.8, 14.7, 15.0, 15.8, 16.1, 16.5, 17.3, 18.0, 18.5, 19.1, 20.8, 21.7, and 25.3 degrees. In some embodiments, the form has at least five XRPD peaks, in terms of 2-theta (±0.2 degrees), selected from 4.5, 7.9, 9.0, 10.8, 13.1, 13.5, 13.8, 14.7, 15.0, 15.8, 16.1, 16.5, 17.3, 18.0, 18.5, 19.1, 20.8, 21.7, and 25.3 degrees. In some embodiments, the form has characteristic XRPD peaks, in terms of 2-theta (±0.2 degrees), at 4.5, 7.9, 9.0, 10.8, 13.1, 13.5, 13.8, 14.7, 15.0, 15.8, 16.1, 16.5, 17.3, 18.0, 18.5, 19.1, 20.8, 21.7, and 25.3 degrees.

Figure 2:
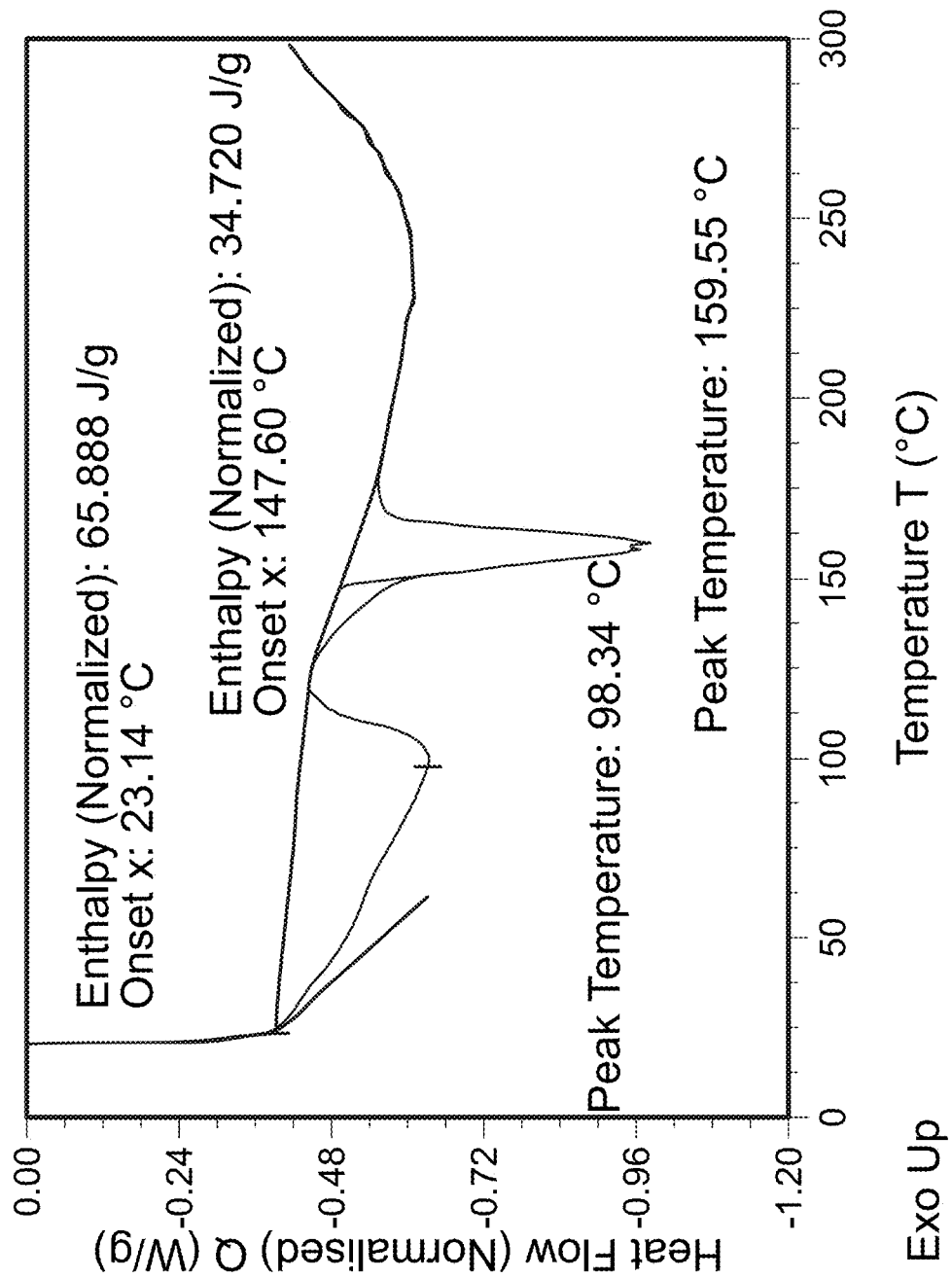
FIG. 2 shows a DSC thermogram of crystalline Form I of Compound 1.
Figure 3:
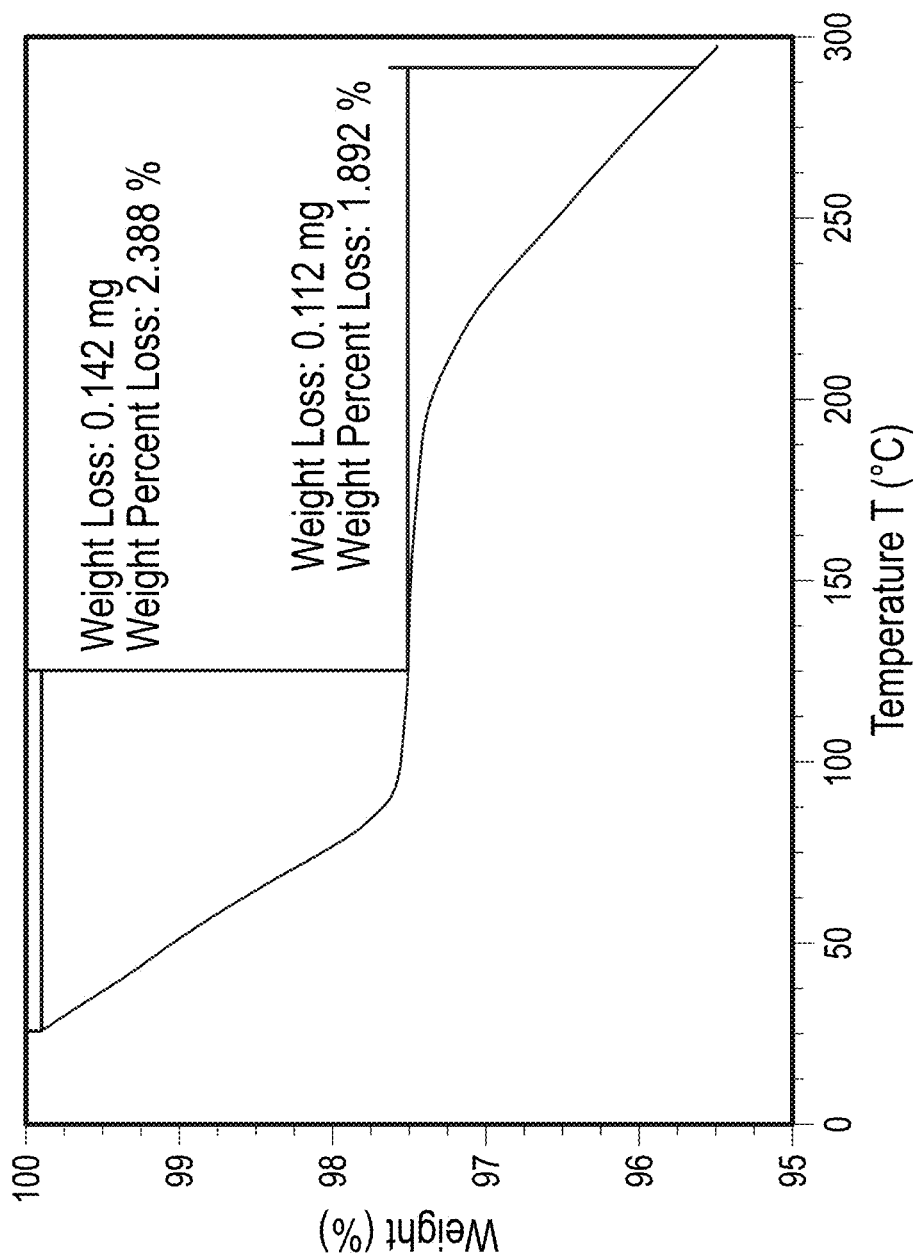
FIG. 3 shows a TGA thermogram of crystalline Form I of Compound 1.

In some embodiments, the form has an XRPD pattern as substantially shown in FIG. 1. In some embodiments, the form has a first endothermic peak with an onset temperature (±3° C.) at 23° C. and a maximum at 98° C. and a second endothermic peak with an onset temperature (±3° C.) at 147° C. and a maximum at 159° C. in a DSC thermogram. In some embodiments, the form has a DSC thermogram substantially as shown in FIG. 2. In some embodiments, the form has a TGA thermogram substantially as shown in FIG. 3.

Form IV of Compound 1

In some embodiments, the crystalline form is Form IV. In some embodiments, Form IV is non-solvated. In some embodiments, the form has at least one XRPD peaks, in terms of 2-theta (±0.2 degrees), selected from 6.5, 7.4, 12.3, 14.8, 17.4, 18.9, 19.8, and 24.2 degrees. In some embodiments, the form has at least two XRPD peaks, in terms of 2-theta (±0.2 degrees), selected from 6.5, 7.4, 12.3, 14.8, 17.4, 18.9, 19.8, and 24.2 degrees. In some embodiments, the form has at least three XRPD peaks, in terms of 2-theta (±0.2 degrees), selected from 6.5, 7.4, 12.3, 14.8, 17.4, 18.9, 19.8, and 24.2 degrees. In some embodiments, the form has at least four XRPD peaks, in terms of 2-theta (±0.2 degrees), selected from 6.5, 7.4, 12.3, 14.8, 17.4, 18.9, 19.8, and 24.2 degrees. In some embodiments, the form has at least five XRPD peaks, in terms of 2-theta (±0.2 degrees), selected from 6.5, 7.4, 12.3, 14.8, 17.4, 18.9, 19.8, and 24.2 degrees. In some embodiments, the form has characteristic XRPD peaks, in terms of 2-theta (±0.2 degrees), at 6.5, 7.4, 12.3, 14.8, 17.4, 18.9, 19.8, and 24.2 degrees.

In some embodiments, the form has at least one XRPD peaks, in terms of 2-theta (±0.2 degrees), selected from 4.0, 6.5, 7.4, 12.3, 13.7, 14.8, 15.6, 16.0, 16.7, 17.4, 18.9, 19.8, and 24.2 degrees. In some embodiments, the form has at least two XRPD peaks, in terms of 2-theta (±0.2 degrees), selected from 4.0, 6.5, 7.4, 12.3, 13.7, 14.8, 15.6, 16.0, 16.7, 17.4, 18.9, 19.8, and 24.2 degrees. In some embodiments, the form has at least three XRPD peaks, in terms of 2-theta (±0.2 degrees), selected from 4.0, 6.5, 7.4, 12.3, 13.7, 14.8, 15.6, 16.0, 16.7, 17.4, 18.9, 19.8, and 24.2 degrees. In some embodiments, the form has at least four XRPD peaks, in terms of 2-theta (±0.2 degrees), selected from 4.0, 6.5, 7.4, 12.3, 13.7, 14.8, 15.6, 16.0, 16.7, 17.4, 18.9, 19.8, and 24.2 degrees. In some embodiments, the form has at least five XRPD peaks, in terms of 2-theta (±0.2 degrees), selected from 4.0, 6.5, 7.4, 12.3, 13.7, 14.8, 15.6, 16.0, 16.7, 17.4, 18.9, 19.8, and 24.2 degrees. In some embodiments, the form has characteristic XRPD peaks, in terms of 2-theta (±0.2 degrees), at 4.0, 6.5, 7.4, 12.3, 13.7, 14.8, 15.6, 16.0, 16.7, 17.4, 18.9, 19.8, and 24.2 degrees.

Figure 10:
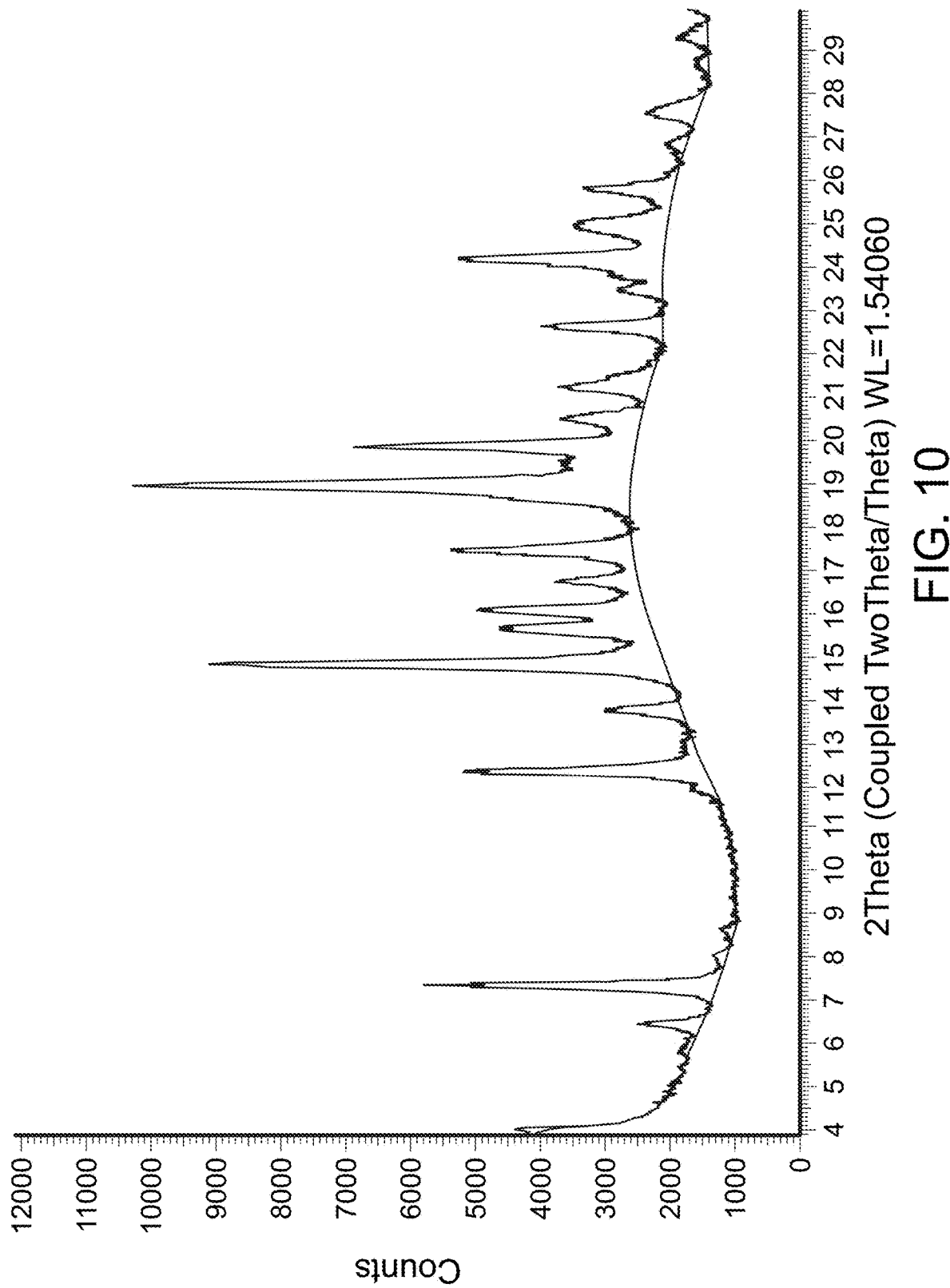
FIG. 10 shows an XRPD pattern of the crystalline Form IV of Compound 1.
Figure 11:
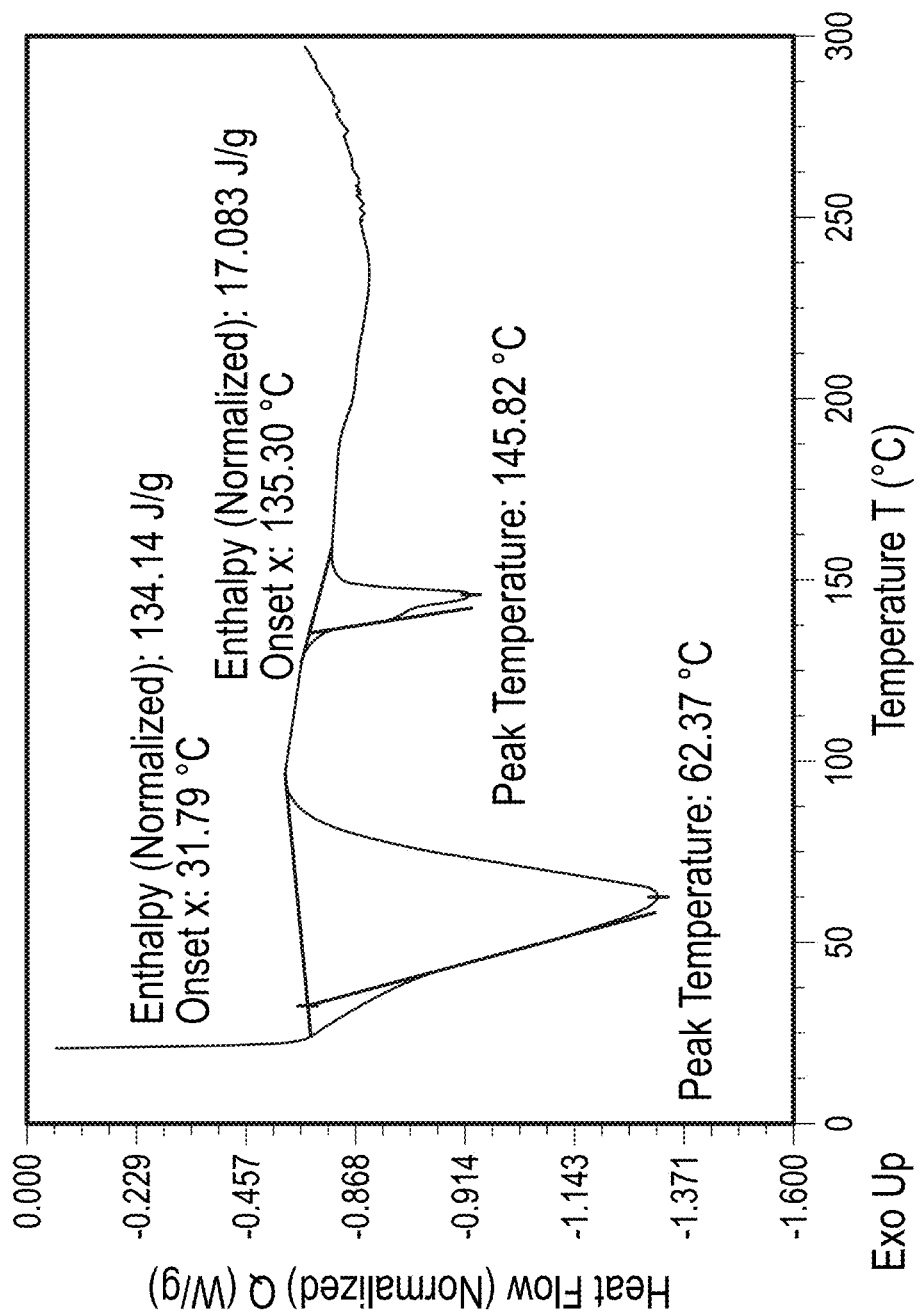
FIG. 11 shows a DSC thermogram of crystalline Form IV of Compound 1.
Figure 12:
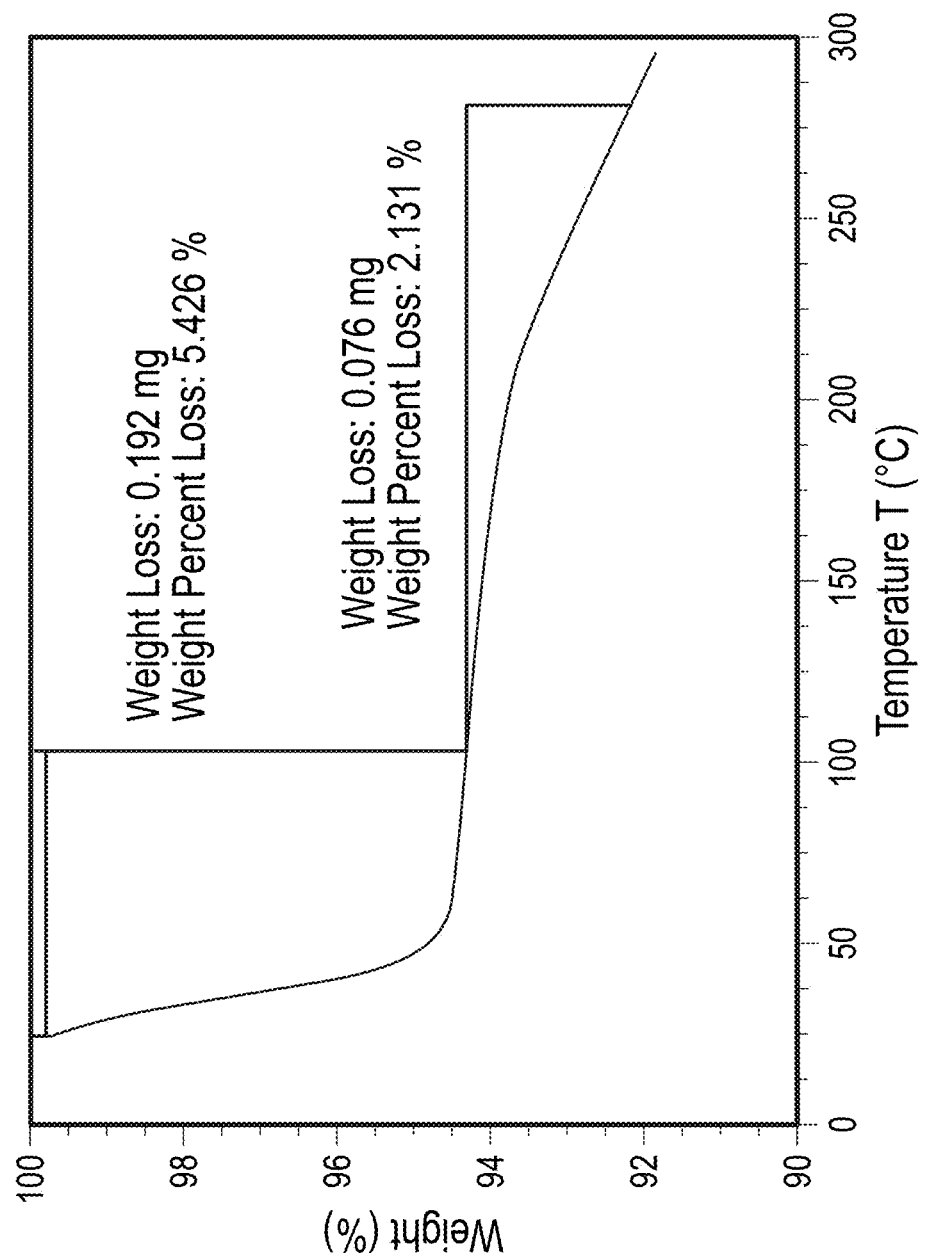
FIG. 12 shows a TGA thermogram of crystalline Form IV of Compound 1.

In some embodiments, the form has an XRPD pattern as substantially shown in FIG. 10. In some embodiments, the form has a first endothermic peak with an onset temperature (±3° C.) at 31° C. and a maximum at 62° C. and a second endothermic peak with an onset temperature (±3° C.) at 135° C. and a maximum at 145° C. in a DSC thermogram. In some embodiments, the form has a DSC thermogram substantially as depicted in FIG. 11. In some embodiments, the form has a TGA thermogram substantially as depicted in FIG. 12.

Form II of Compound 1

In some embodiments, the crystalline form is Form II. In some embodiments, Form II is a solvate. In some embodiments, Form II is a tetrahydrofuran solvate. In some embodiments, the form has at least one XRPD peak, in terms of 2-theta (±0.2 degrees), selected from 7.5, 9.9, 12.8, 13.4, 14.4, 15.0, 17.1, 19.8, and 23.3 degrees. In some embodiments, the form has at least two XRPD peaks, in terms of 2-theta (±0.2 degrees), selected from 7.5, 9.9, 12.8, 13.4, 14.4, 15.0, 17.1, 19.8, and 23.3 degrees. In some embodiments, the form has at least three XRPD peaks, in terms of 2-theta (±0.2 degrees), selected from 7.5, 9.9, 12.8, 13.4, 14.4, 15.0, 17.1, 19.8, and 23.3 degrees. In some embodiments, the form has at least four XRPD peaks, in terms of 2-theta (±0.2 degrees), selected from 7.5, 9.9, 12.8, 13.4, 14.4, 15.0, 17.1, 19.8, and 23.3 degrees. In some embodiments, the form has at least five XRPD peaks, in terms of 2-theta (±0.2 degrees), selected from 7.5, 9.9, 12.8, 13.4, 14.4, 15.0, 17.1, 19.8, and 23.3 degrees. In some embodiments, the form has characteristic XRPD peaks, in terms of 2-theta (±0.2 degrees), at 7.5, 9.9, 12.8, 13.4, 14.4, 15.0, 17.1, 19.8, and 23.3 degrees.

In some embodiments, the form has at least one XRPD peak, in terms of 2-theta (±0.2 degrees), selected from 7.5, 9.9, 12.8, 13.4, 14.4, 15.0, 17.1, 18.2, 18.9, 19.8, 22.9, and 23.3 degrees. In some embodiments, the form has at least two XRPD peaks, in terms of 2-theta (±0.2 degrees), selected from 7.5, 9.9, 12.8, 13.4, 14.4, 15.0, 17.1, 18.2, 18.9, 19.8, 22.9, and 23.3 degrees. In some embodiments, the form has at least three XRPD peaks, in terms of 2-theta (±0.2 degrees), selected from 7.5, 9.9, 12.8, 13.4, 14.4, 15.0, 17.1, 18.2, 18.9, 19.8, 22.9, and 23.3 degrees. In some embodiments, the form has at least four XRPD peaks, in terms of 2-theta (±0.2 degrees), selected from 7.5, 9.9, 12.8, 13.4, 14.4, 15.0, 17.1, 18.2, 18.9, 19.8, 22.9, and 23.3 degrees. In some embodiments, the form has at least five XRPD peaks, in terms of 2-theta (±0.2 degrees), selected from 7.5, 9.9, 12.8, 13.4, 14.4, 15.0, 17.1, 18.2, 18.9, 19.8, 22.9, and 23.3 degrees. In some embodiments, the form has characteristic XRPD peaks, in terms of 2-theta (±0.2 degrees), at 7.5, 9.9, 12.8, 13.4, 14.4, 15.0, 17.1, 18.2, 18.9, 19.8, 22.9, and 23.3 degrees.

In some embodiments, the form has at least one XRPD peak, in terms of 2-theta (±0.2 degrees), selected from 7.5, 9.7, 9.9, 10.7, 11.3, 11.6, 12.8, 12.9, 13.4, 14.4, 14.8, 15.0, 15.8, 16.1, 16.7, 17.1, 18.0, 18.2, 18.9, 19.6, 19.8, 20.0, 22.9, and 23.3 degrees. In some embodiments, the form has at least two XRPD peaks, in terms of 2-theta (±0.2 degrees), selected from 7.5, 9.7, 9.9, 10.7, 11.3, 11.6, 12.8, 12.9, 13.4, 14.4, 14.8, 15.0, 15.8, 16.1, 16.7, 17.1, 18.0, 18.2, 18.9, 19.6, 19.8, 20.0, 22.9, and 23.3 degrees. In some embodiments, the form has at least three XRPD peaks, in terms of 2-theta (±0.2 degrees), selected from 7.5, 9.7, 9.9, 10.7, 11.3, 11.6, 12.8, 12.9, 13.4, 14.4, 14.8, 15.0, 15.8, 16.1, 16.7, 17.1, 18.0, 18.2, 18.9, 19.6, 19.8, 20.0, 22.9, and 23.3 degrees. In some embodiments, the form has at least four XRPD peaks, in terms of 2-theta (±0.2 degrees), selected from 7.5, 9.7, 9.9, 10.7, 11.3, 11.6, 12.8, 12.9, 13.4, 14.4, 14.8, 15.0, 15.8, 16.1, 16.7, 17.1, 18.0, 18.2, 18.9, 19.6, 19.8, 20.0, 22.9, and 23.3 degrees. In some embodiments, the form has at least five XRPD peaks, in terms of 2-theta (±0.2 degrees), selected from 7.5, 9.7, 9.9, 10.7, 11.3, 11.6, 12.8, 12.9, 13.4, 14.4, 14.8, 15.0, 15.8, 16.1, 16.7, 17.1, 18.0, 18.2, 18.9, 19.6, 19.8, 20.0, 22.9, and 23.3 degrees. In some embodiments, the form has characteristic XRPD peaks, in terms of 2-theta (±0.2 degrees), at 7.5, 9.7, 9.9, 10.7, 11.3, 11.6, 12.8, 12.9, 13.4, 14.4, 14.8, 15.0, 15.8, 16.1, 16.7, 17.1, 18.0, 18.2, 18.9, 19.6, 19.8, 20.0, 22.9, and 23.3 degrees.

Figure 4:
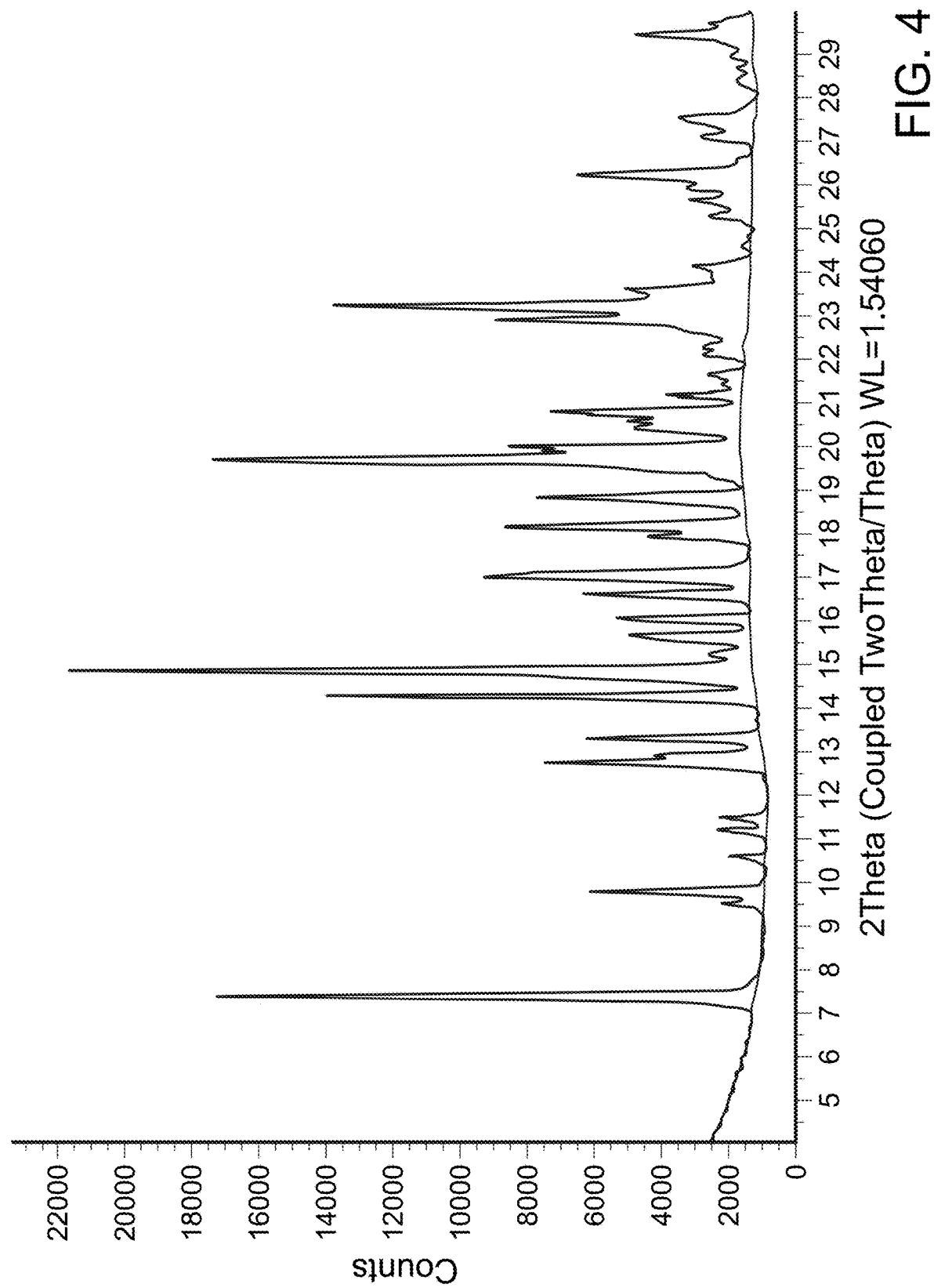
FIG. 4 shows an XRPD pattern of the crystalline Form II of Compound 1.
Figure 5:
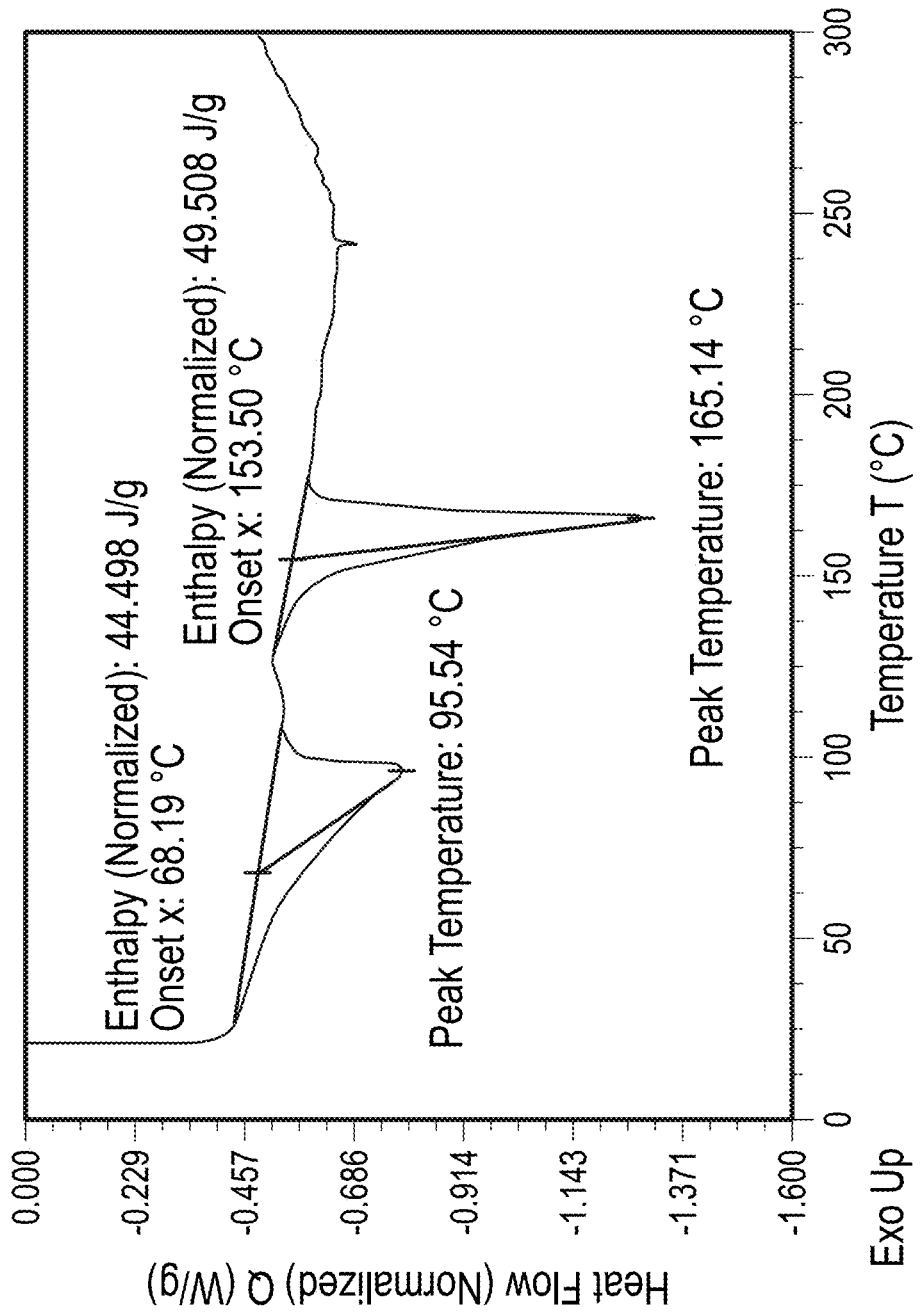
FIG. 5 shows a DSC thermogram of crystalline Form II of Compound 1.
Figure 6:
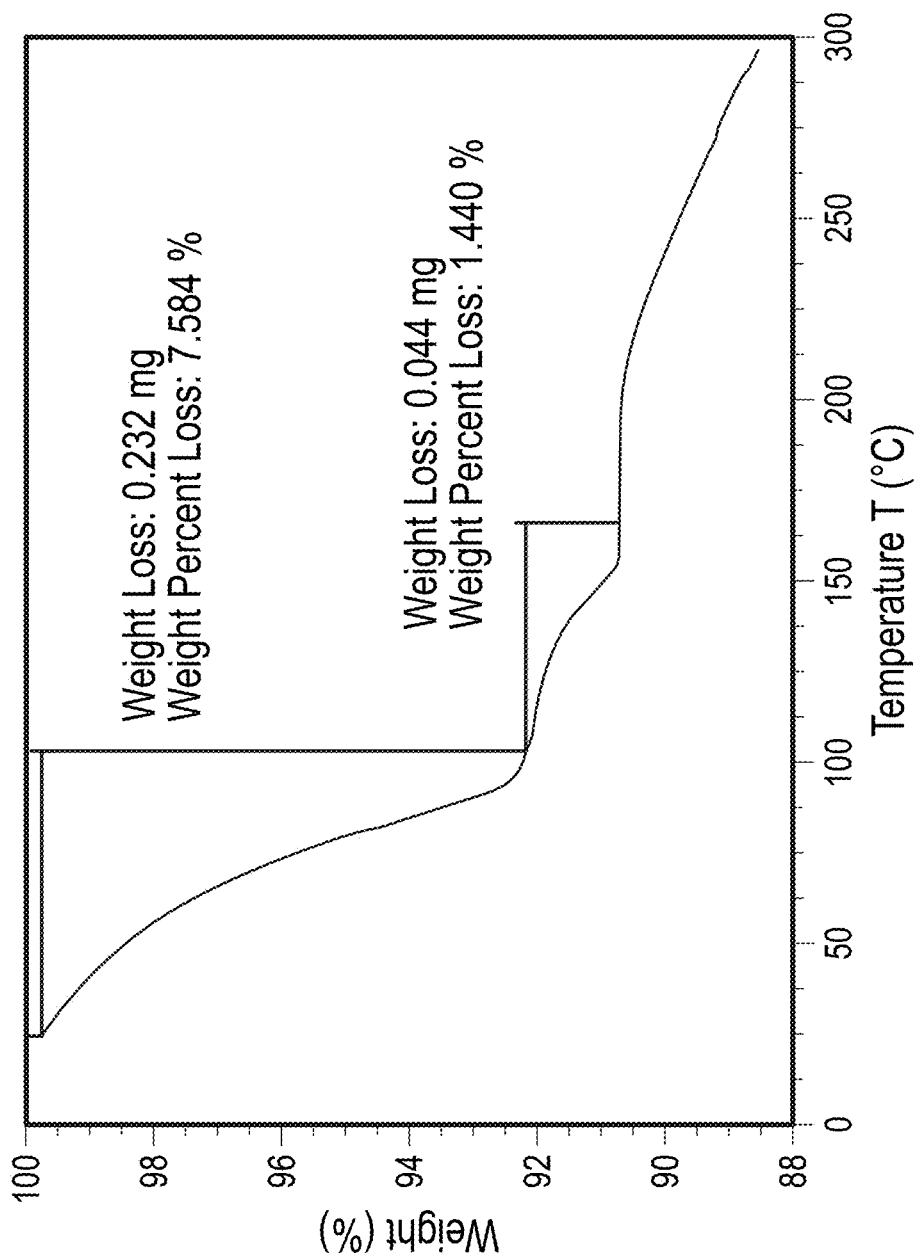
FIG. 6 shows a TGA thermogram of crystalline Form II of Compound 1.

In some embodiments, the form has an XRPD pattern as substantially shown in FIG. 4. In some embodiments, the form has a first endothermic peak with an onset temperature (±3° C.) at 68° C. and a maximum at 95° C. and a second endothermic peak with an onset temperature (±3° C.) at 153° C. and a maximum at 165° C. in a DSC thermogram. In some embodiments, the form has a DSC thermogram substantially as depicted in FIG. 5. In some embodiments, the form has a TGA thermogram substantially as depicted in FIG. 6.

Form III of Compound 1

In some embodiments, the crystalline form is Form III. In some embodiments, Form III is a solvate. In some embodiments, Form III is a tetrahydrofuran solvate. In some embodiments, the form has at least one XRPD peak, in terms of 2-theta (±0.2 degrees), selected from 5.9, 8.0, 12.6, 15.1, 17.0, 18.4, and 18.9 degrees. In some embodiments, the form has at least two XRPD peaks, in terms of 2-theta (±0.2 degrees), selected from 5.9, 8.0, 12.6, 15.1, 17.0, 18.4, and 18.9 degrees. In some embodiments, the form has at least three XRPD peaks, in terms of 2-theta (±0.2 degrees), selected from 5.9, 8.0, 12.6, 15.1, 17.0, 18.4, and 18.9 degrees. In some embodiments, the form has at least four XRPD peaks, in terms of 2-theta (±0.2 degrees), selected from 5.9, 8.0, 12.6, 15.1, 17.0, 18.4, and 18.9 degrees. In some embodiments, the form has at least five XRPD peaks, in terms of 2-theta (±0.2 degrees), selected from 5.9, 8.0, 12.6, 15.1, 17.0, 18.4, and 18.9 degrees. In some embodiments, the form has characteristic XRPD peaks, in terms of 2-theta (±0.2 degrees), at 5.9, 8.0, 12.6, 15.1, 17.0, 18.4, and 18.9 degrees.

In some embodiments, the form has at least one XRPD peak, in terms of 2-theta (±0.2 degrees), selected from 5.9, 8.0, 11.2, 12.6, 15.1, 17.0, 18.4, 18.9, and 21.7 degrees. In some embodiments, the form has at least two XRPD peaks, in terms of 2-theta (±0.2 degrees), selected from 5.9, 8.0, 11.2, 12.6, 15.1, 17.0, 18.4, 18.9, and 21.7 degrees. In some embodiments, the form has at least three XRPD peaks, in terms of 2-theta (±0.2 degrees), selected from 5.9, 8.0, 11.2, 12.6, 15.1, 17.0, 18.4, 18.9, and 21.7 degrees. In some embodiments, the form has at least four XRPD peaks, in terms of 2-theta (±0.2 degrees), selected from 5.9, 8.0, 11.2, 12.6, 15.1, 17.0, 18.4, 18.9, and 21.7 degrees. In some embodiments, the form has at least five XRPD peaks, in terms of 2-theta (±0.2 degrees), selected from 5.9, 8.0, 11.2, 12.6, 15.1, 17.0, 18.4, 18.9, and 21.7 degrees. In some embodiments, the form has characteristic XRPD peaks, in terms of 2-theta (±0.2 degrees), at 5.9, 8.0, 11.2, 12.6, 15.1, 17.0, 18.4, 18.9, and 21.7 degrees.

In some embodiments, the form has at least one XRPD peak, in terms of 2-theta (±0.2 degrees), selected from 5.9, 6.8, 8.0, 11.1, 11.2, 12.6, 14.9, 15.1, 15.3, 16.4, 16.7, 17.0, 18.4, 18.9, 21.7, and 24.2 degrees. In some embodiments, the form has at least two XRPD peaks, in terms of 2-theta (±0.2 degrees), selected from 5.9, 6.8, 8.0, 11.1, 11.2, 12.6, 14.9, 15.1, 15.3, 16.4, 16.7, 17.0, 18.4, 18.9, 21.7, and 24.2 degrees. In some embodiments, the form has at least three XRPD peaks, in terms of 2-theta (±0.2 degrees), selected from 5.9, 6.8, 8.0, 11.1, 11.2, 12.6, 14.9, 15.1, 15.3, 16.4, 16.7, 17.0, 18.4, 18.9, 21.7, and 24.2 degrees. In some embodiments, the form has at least four XRPD peaks, in terms of 2-theta (±0.2 degrees), selected from 5.9, 6.8, 8.0, 11.1, 11.2, 12.6, 14.9, 15.1, 15.3, 16.4, 16.7, 17.0, 18.4, 18.9, 21.7, and 24.2 degrees. In some embodiments, the form has at least five XRPD peaks, in terms of 2-theta (±0.2 degrees), selected from 5.9, 6.8, 8.0, 11.1, 11.2, 12.6, 14.9, 15.1, 15.3, 16.4, 16.7, 17.0, 18.4, 18.9, 21.7, and 24.2 degrees. In some embodiments, the form has characteristic XRPD peaks, in terms of 2-theta (±0.2 degrees), at 5.9, 6.8, 8.0, 11.1, 11.2, 12.6, 14.9, 15.1, 15.3, 16.4, 16.7, 17.0, 18.4, 18.9, 21.7, and 24.2 degrees.

Figure 7:
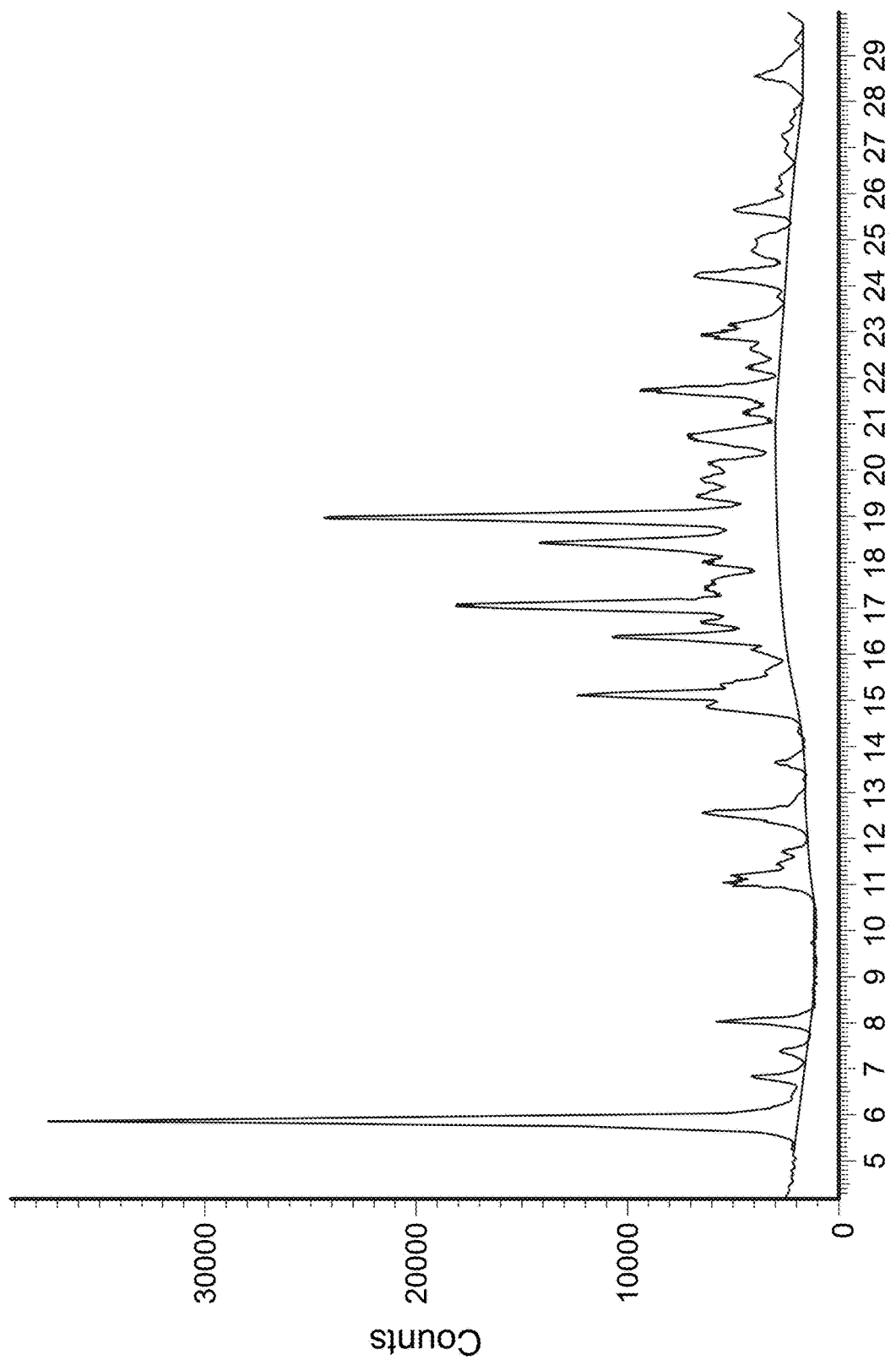
FIG. 7 shows an XRPD pattern of the crystalline Form III of Compound 1.
Figure 8:
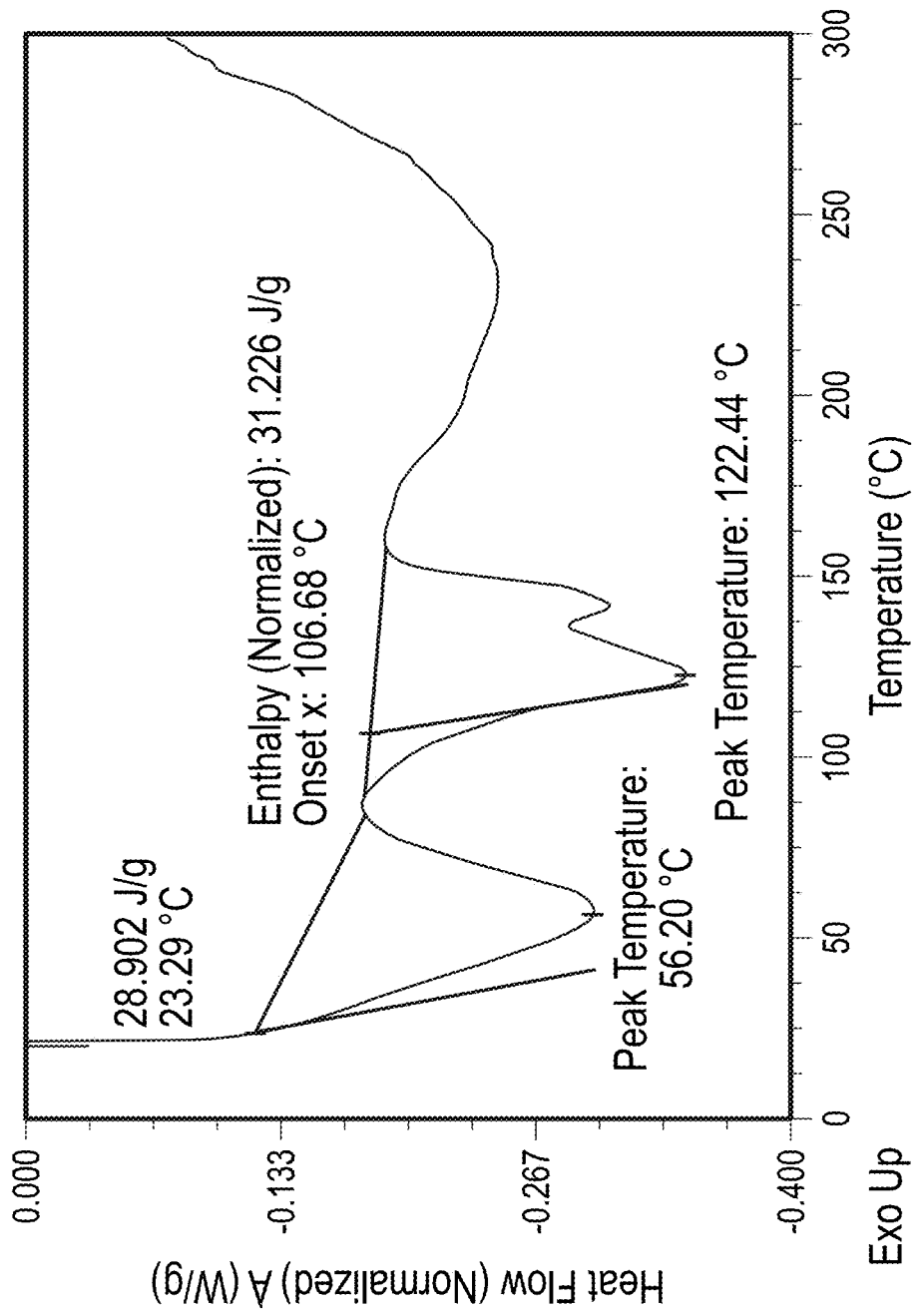
FIG. 8 shows a DSC thermogram of crystalline Form III of Compound 1.
Figure 9:
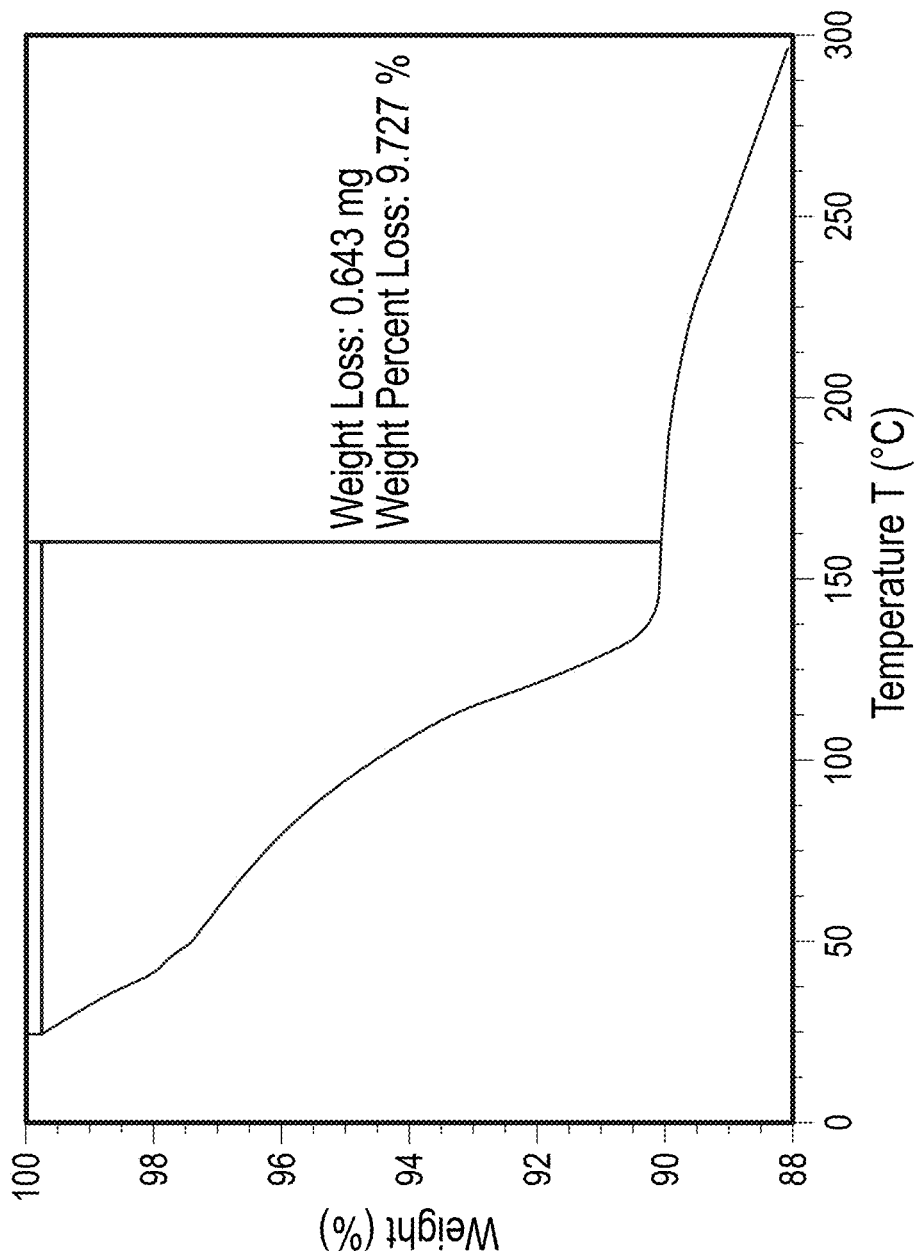
FIG. 9 shows a TGA thermogram of crystalline Form III of Compound 1.

In some embodiments, the form has an XRPD pattern as substantially shown in FIG. 7. In some embodiments, the crystalline form has a first endothermic peak with an onset temperature (±3° C.) at 23° C. and a maximum at 56° C. and a second endothermic peak with an onset temperature (±3° C.) at 106° C. and a maximum at 122° C. in a DSC thermogram. In some embodiments, the form has a DSC thermogram substantially as depicted in FIG. 8. In some embodiments, the form has a TGA thermogram substantially as depicted in FIG. 9.

Form V of Compound 1

In some embodiments, the crystalline form is Form V. In some embodiments, Form V is a solvate. In some embodiments, Form V is a tetrahydrofuran solvate. In some embodiments, the form has at least one XRPD peak, in terms of 2-theta (±0.2 degrees), selected from 5.8, 8.0, 12.5, 15.1, 16.3, 17.0, 18.3, 18.9, 20.7, and 21.7 degrees. In some embodiments, the form has at least two XRPD peaks, in terms of 2-theta (±0.2 degrees), selected from 5.8, 8.0, 12.5, 15.1, 16.3, 17.0, 18.3, 18.9, 20.7, and 21.7 degrees. In some embodiments, the form has at least three XRPD peaks, in terms of 2-theta (±0.2 degrees), selected from 5.8, 8.0, 12.5, 15.1, 16.3, 17.0, 18.3, 18.9, 20.7, and 21.7 degrees. In some embodiments, the form has at least four XRPD peaks, in terms of 2-theta (±0.2 degrees), selected from 5.8, 8.0, 12.5, 15.1, 16.3, 17.0, 18.3, 18.9, 20.7, and 21.7 degrees. In some embodiments, the form has at least five XRPD peaks, in terms of 2-theta (±0.2 degrees), selected from 5.8, 8.0, 12.5, 15.1, 16.3, 17.0, 18.3, 18.9, 20.7, and 21.7 degrees. In some embodiments, the form has characteristic XRPD peaks, in terms of 2-theta (±0.2 degrees), at 5.8, 8.0, 12.5, 15.1, 16.3, 17.0, 18.3, 18.9, 20.7, and 21.7 degrees.

In some embodiments, the form has at least one XRPD peak, in terms of 2-theta (±0.2 degrees), selected from 5.8, 8.0, 11.1, 12.5, 15.1, 16.3, 17.0, 18.0, 18.3, 18.9, 20.7, 21.7, and 22.9 degrees. In some embodiments, the form has at least two XRPD peaks, in terms of 2-theta (±0.2 degrees), selected from 5.8, 8.0, 11.1, 12.5, 15.1, 16.3, 17.0, 18.0, 18.3, 18.9, 20.7, 21.7, and 22.9 degrees. In some embodiments, the form has at least three XRPD peaks, in terms of 2-theta (±0.2 degrees), selected from 5.8, 8.0, 11.1, 12.5, 15.1, 16.3, 17.0, 18.0, 18.3, 18.9, 20.7, 21.7, and 22.9 degrees. In some embodiments, the form has at least four XRPD peaks, in terms of 2-theta (±0.2 degrees), selected from 5.8, 8.0, 11.1, 12.5, 15.1, 16.3, 17.0, 18.0, 18.3, 18.9, 20.7, 21.7, and 22.9 degrees. In some embodiments, the form has at least five XRPD peaks, in terms of 2-theta (±0.2 degrees), selected from 5.8, 8.0, 11.1, 12.5, 15.1, 16.3, 17.0, 18.0, 18.3, 18.9, 20.7, 21.7, and 22.9 degrees. In some embodiments, the form has characteristic XRPD peaks, in terms of 2-theta (±0.2 degrees), at 5.8, 8.0, 11.1, 12.5, 15.1, 16.3, 17.0, 18.0, 18.3, 18.9, 20.7, 21.7, and 22.9 degrees.

In some embodiments, the form has at least one XRPD peak, in terms of 2-theta (±0.2 degrees), selected from 5.8, 6.8, 8.0, 11.1, 12.5, 15.1, 16.3, 17.0, 18.0, 18.3, 18.9, 19.7, 20.0, 20.7, 21.7, 22.9, 24.2, 25.6, and 28.5 degrees. In some embodiments, the form has at least two XRPD peaks, in terms of 2-theta (±0.2 degrees), selected from 5.8, 6.8, 8.0, 11.1, 12.5, 15.1, 16.3, 17.0, 18.0, 18.3, 18.9, 19.7, 20.0, 20.7, 21.7, 22.9, 24.2, 25.6, and 28.5 degrees. In some embodiments, the form has at least three XRPD peaks, in terms of 2-theta (±0.2 degrees), selected from 5.8, 6.8, 8.0, 11.1, 12.5, 15.1, 16.3, 17.0, 18.0, 18.3, 18.9, 19.7, 20.0, 20.7, 21.7, 22.9, 24.2, 25.6, and 28.5 degrees. In some embodiments, the form has at least four XRPD peaks, in terms of 2-theta (±0.2 degrees), selected from 5.8, 6.8, 8.0, 11.1, 12.5, 15.1, 16.3, 17.0, 18.0, 18.3, 18.9, 19.7, 20.0, 20.7, 21.7, 22.9, 24.2, 25.6, and 28.5 degrees. In some embodiments, the form has at least five XRPD peaks, in terms of 2-theta (±0.2 degrees), selected from 5.8, 6.8, 8.0, 11.1, 12.5, 15.1, 16.3, 17.0, 18.0, 18.3, 18.9, 19.7, 20.0, 20.7, 21.7, 22.9, 24.2, 25.6, and 28.5 degrees. In some embodiments, the form has characteristic XRPD peaks, in terms of 2-theta (±0.2 degrees), at 5.8, 6.8, 8.0, 11.1, 12.5, 15.1, 16.3, 17.0, 18.0, 18.3, 18.9, 19.7, 20.0, 20.7, 21.7, 22.9, 24.2, 25.6, and 28.5 degrees.

Figure 13:
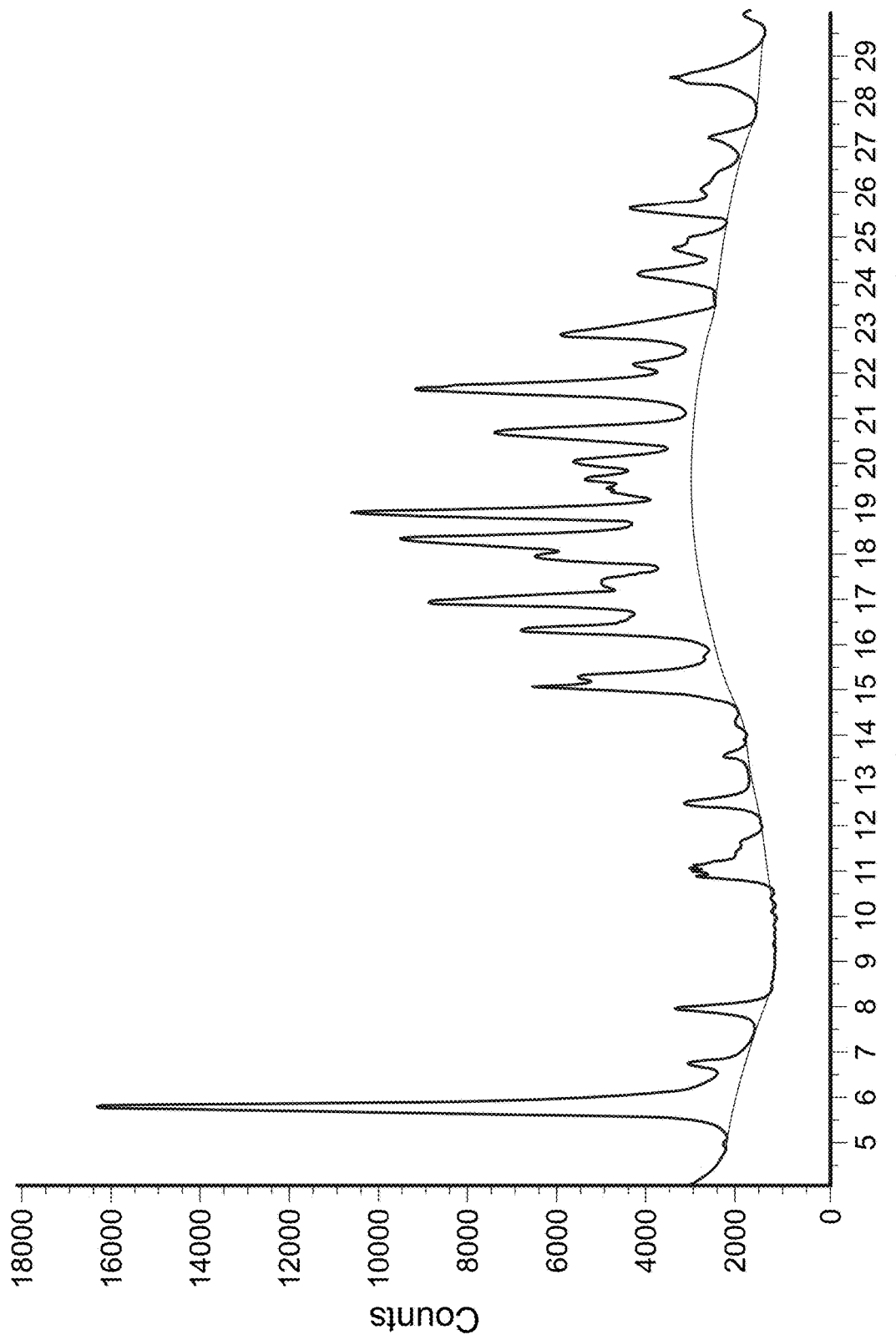
FIG. 13 shows an XRPD pattern of the crystalline Form V of Compound 1.
Figure 14:
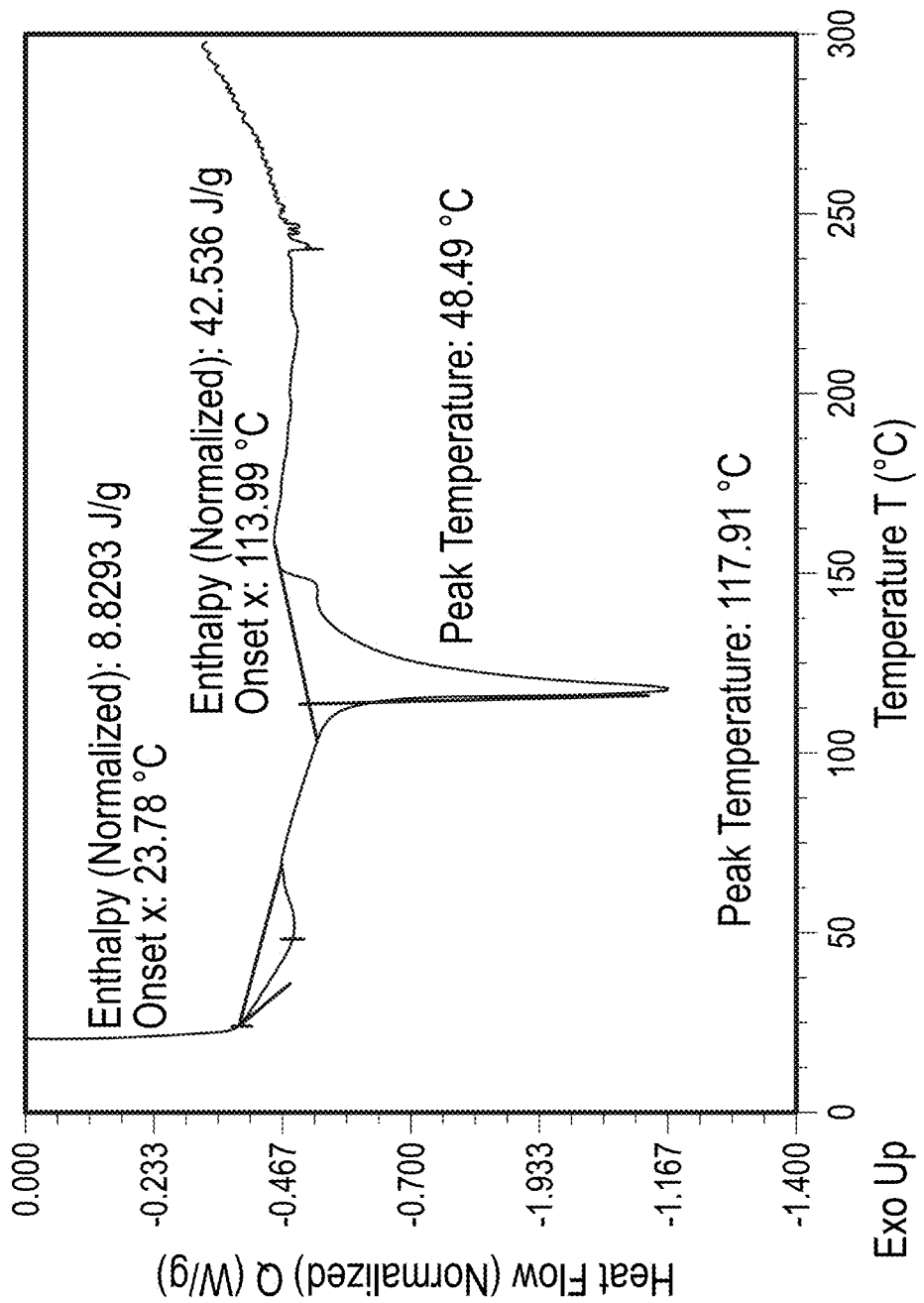
FIG. 14 shows a DSC thermogram of crystalline Form V of Compound 1.
Figure 15:
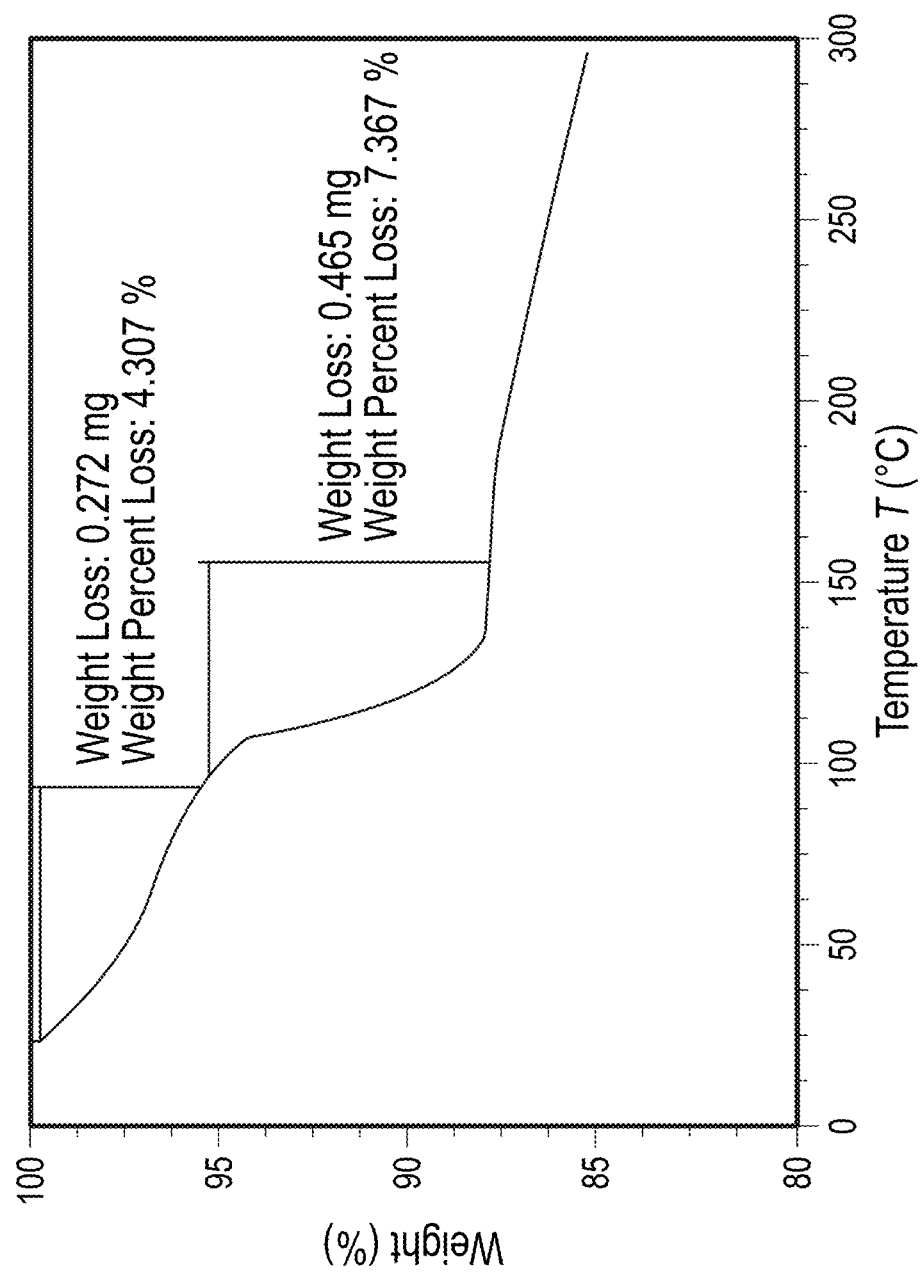
FIG. 15 shows a TGA thermogram of crystalline Form V of Compound 1.

In some embodiments, the form has an XRPD pattern as substantially shown in FIG. 13. In some embodiments, the crystalline form has a first endothermic peak with an onset temperature (±3° C.) at 23° C. and a maximum at 48° C. and a second endothermic peak with an onset temperature (±3° C.) at 113° C. and a maximum at 117° C. in a DSC thermogram. In some embodiments, the form has a DSC thermogram substantially as depicted in FIG. 14. In some embodiments, the form has a TGA thermogram substantially as depicted in FIG. 15.

In some embodiments, a pharmaceutical composition comprising a crystalline form as described herein, and a pharmaceutically acceptable carrier or excipient. In some embodiments, a solid oral dosage form comprising the pharmaceutical composition.

Provided herein is also a process of preparing a crystalline form of Compound 1:

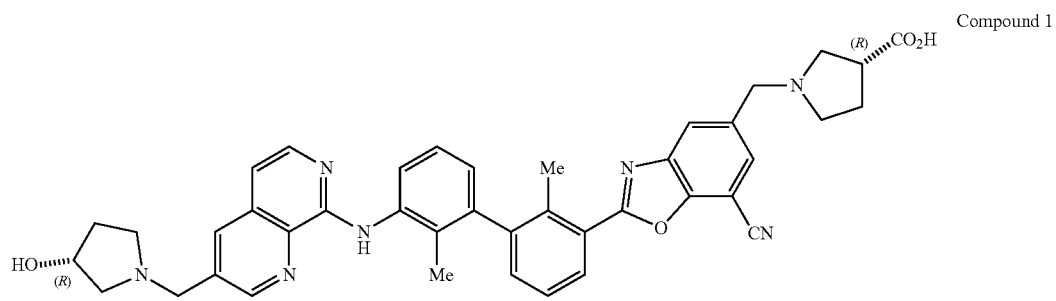

Compound 1 which is Form I, comprising converting a tetrahydrofuran solvate of Compound 1 to said Form I.

In some embodiments, the tetrahydrofuran solvate is Form II of Compound 1. In some embodiments, the converting comprises slurrying the Form II in a solvent component to form the Form I. In some embodiments, the slurrying comprises preparing a suspension comprising the Form II and a solvent component. In some embodiments, the slurrying comprises preparing a suspension comprising the Form II and a solvent component; heating the suspension; and after said heating, cooling the suspension to form the Form I as a solid. In some embodiments, the slurrying comprises preparing a suspension comprising the Form II and a solvent component; heating the suspension; and after said heating, cooling the suspension to form the Form I as a solid; wherein the solvent component comprises acetone and water. In some embodiments, the slurrying comprises preparing a suspension comprising the Form II and a solvent component; heating the suspension to a temperature of about 35° C. to about 70° C.; and after said heating, cooling the suspension to a temperature of about 15° C. to about 25° C. to form the Form I as a solid; wherein the solvent component comprises acetone and water.

In some embodiments, the converting further comprises collecting solids from the cooled suspension. The collected solids can be washed with a polar aprotic solvent; and after said washing, drying the washed solids under vacuum at about 35° C. to about 55° C. under an inert atmosphere to provide crystalline Form I of Compound 1. The drying of the washed solids under vacuum can be at about 45° C. under an inert atmosphere. In some embodiments, the polar aprotic solvent comprises acetone.

In some embodiments, the converting comprises drying the Form II to form the Form I. In some embodiments, the converting optionally further comprising preparing a suspension of a dried Form II in a solvent component. In some embodiments, the converting optionally further comprising preparing a suspension of a dried Form II in a solvent component; and heating the suspension to a temperature of about 35° C. to about 70° C. to provide a heated suspension.

In some embodiments, the converting optionally further comprising preparing a suspension of a dried Form II in a solvent component; heating the suspension to a temperature of about 35° C. to about 70° C.; and after said heating, collecting crystalline Form I of Compound 1. In some embodiments, the heating of the suspension comprising a dried Form II in a solvent component is to a temperature of about 45° C. to about 55° C. In some embodiments, the solvent component comprises an aqueous aprotic polar solvent. In some embodiments, the solvent component comprises an aqueous acetone.

In some embodiments, the converting comprises:

(ia) preparing a first suspension of Form II in a solvent component;

(iia) heating the first suspension of the Form II of the compound to a temperature of about 35° C. to about 70° C. (or, alternatively, to a temperature of about 45° C. to about 55° C.) to produce a second suspension;

(iiia) agitating the second suspension for a period of time to produce a third suspension; and (iva) cooling the third suspension of the compound to a temperature of about 15° C. to about 25° C. to produce a fourth suspension. the solvent component comprises polar aprotic solvent and water.

In some embodiments, the solvent component comprises polar aprotic solvent and water. In some embodiments, the solvent component comprises acetone and water.

In some embodiments, the process further comprises:

(ib) collecting solids from the fourth suspension;

(iib) washing the collected solids with a polar aprotic solvent component; and (iiib) drying the washed solids under vacuum at about 35° C. to about 55° C. (or, alternatively, about 45° C.) under an inert atmosphere to provide Form I.

In some embodiments, polar aprotic solvent component comprises acetone.

In some embodiments, a process of preparing a crystalline, tetrahydrofuran solvate of Compound 1:

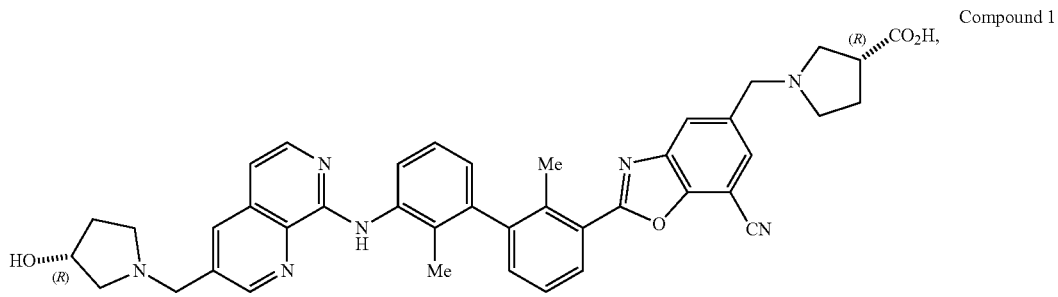

Compound 1 which is Form II, comprising converting Form I of the compound to Form II in the presence of tetrahydrofuran. In some embodiments, the converting comprises preparing a suspension of Form I in tetrahydrofuran. In some embodiments, the converting comprises preparing a suspension of Form I in tetrahydrofuran; and heating the suspension to a temperature of about 40° C. to about 70° C. to provide a heated suspension. In some embodiments, the heating of the suspension is to a temperature of about 55° C. In some embodiments, the converting comprises preparing a suspension of Form I in tetrahydrofuran; heating the suspension to a temperature of about 40° C. to about 70° C.; and after said heating, collecting the crystalline Form II of Compound 1.

In some embodiments, a process of preparing a crystalline, tetrahydrofuran solvate of Compound 1:

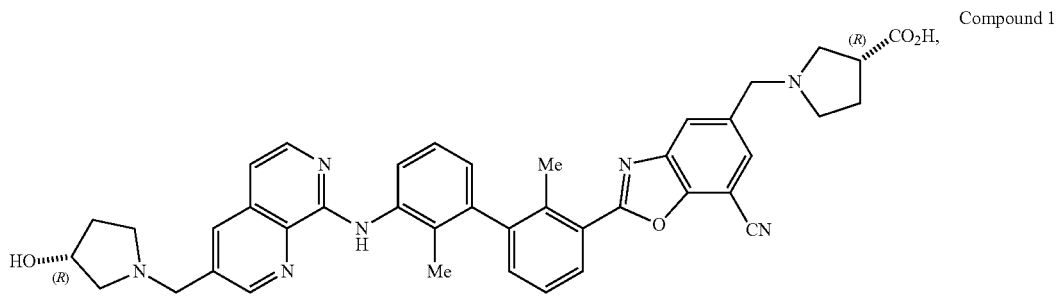

Compound 1 which is Form II, comprising: treating a solution comprising tetrahydrofuran and Compound 1 potassium salt:

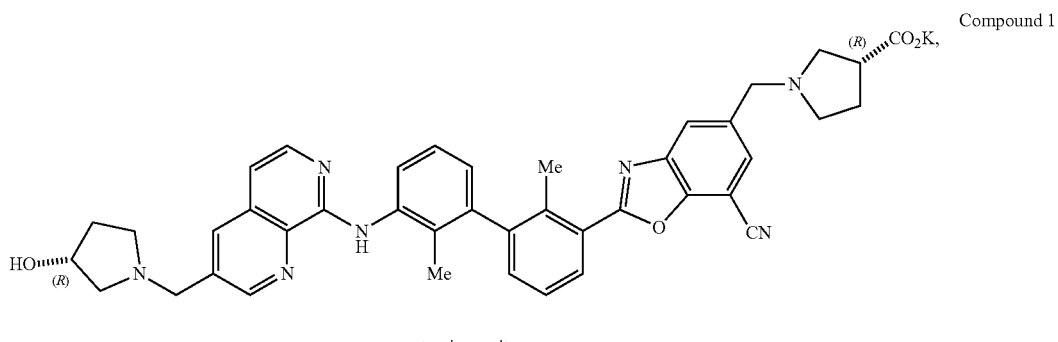

Compound 1
potassium salt with a metal scavenger or an ion exchange resin; and precipitating Form II of Compound 1. In some embodiments, the treating comprises treating with the metal scavenger and the ion exchange resin. In some embodiments, the solution further comprises a $C_{1-6}$ alcohol. In some embodiments, the $C_{1-6}$ alcohol comprises methanol. In some embodiments, the treating comprises heating the solution; and after said heating, cooling the solution. In some embodiments, the treating comprises heating the solution; after said heating, cooling the solution; and after said cooling, filtering the solution and concentrating filtrate. In some embodiments, the treating comprises heating the solution; after said heating, cooling the solution; after said cooling, filtering the solution and concentrating filtrate; and after concentrating said filtrate, adding seed crystals of Form I to said concentrated filtrate. In some embodiments, the treating comprises heating the solution to a temperature of about 60° C. to about 70° C.; and after said heating, cooling the solution to a temperature of about 45° C. to about 55° C.; after said cooling, filtering the solution and concentrating filtrate; and after concentrating said filtrate, adding seed crystals of Form I to said concentrated filtrate to provide a suspension. In some embodiments, the process further comprises adding a solvent component to the suspension. In some embodiments, the process further comprises adding a solvent component to the suspension, wherein the solvent component is isopropyl acetate. In some embodiments, the heating of the solution is to a temperature of about 55° C. to about 65° C. In some embodiments, the cooling of solution is to a temperature of about 45° C. to about 55° C. In some embodiments, the cooling of the solution is to a temperature of about 50° C. In some embodiments, adding seed crystals of Form I to the concentrated filtrate is carried out at a temperature of about 5° C. to about 35. In some embodiments, adding seed crystals of Form I to the concentrated filtrate is carried out at a temperature of about 15° C. to about 25° C.

In some embodiments, provided herein is a process of preparing a crystalline, tetrahydrofuran solvate of Compound 1:

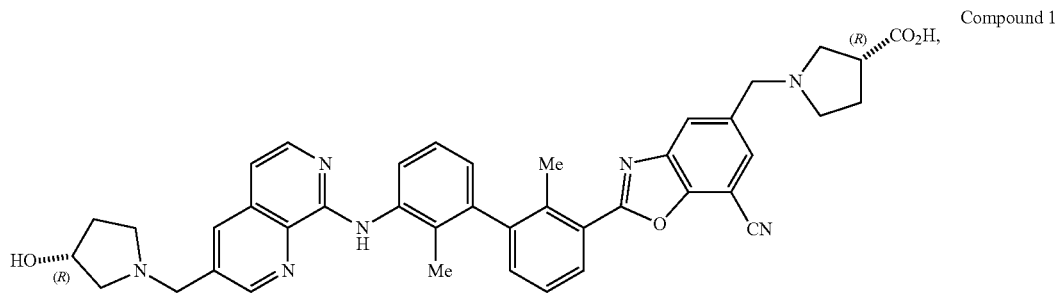

which is Form II, comprising converting Form III, Form IV, or Form V of the compound to Form II in the presence of a solvent component comprising tetrahydrofuran. In some embodiments, the converting comprises preparing a suspension of Form III, Form IV, or Form V in the solvent component. In some embodiments, the converting comprises preparing a suspension of Form III, Form IV, or Form V in the solvent component; heating the suspension to provide a solution; and cooling the solution. In some embodiments, the converting comprises preparing a suspension of Form III, Form IV, or Form V in the solvent component; heating the suspension to provide a solution; after said heating, cooling the solution; and after said cooling, adding seed crystals of Form I to the solution. In some embodiments, the converting comprises preparing a suspension of Form III, Form IV, or Form V in the solvent component; heating the suspension to provide a solution; after said heating, cooling the solution; after said cooling, adding seed crystals of Form I to the cooled solution to provide a seeded suspension; and adding an anti-solvent to the seeded suspension. In some embodiments, the converting comprises preparing a suspension of Form III, Form IV, or Form V in the solvent component; heating the suspension to a temperature of about 35° C. to about 70° C. to provide a solution; after said heating, cooling the solution to about ambient temperature; after said cooling, adding seed crystals of Form I to the cooled solution to provide a seeded suspension; and adding an anti-solvent component to the seeded suspension. In some embodiments, the anti-solvent component comprises isopropyl acetate. In some embodiments, the solvent component comprises tetrahydrofuran, $C_{1-6}$ alcohol, or a mixture thereof. In some embodiments, the solvent component comprises tetrahydrofuran or a mixture of tetrahydrofuran and methanol.

In some embodiments, provided herein is a process of preparing a crystalline Form III of Compound 1:

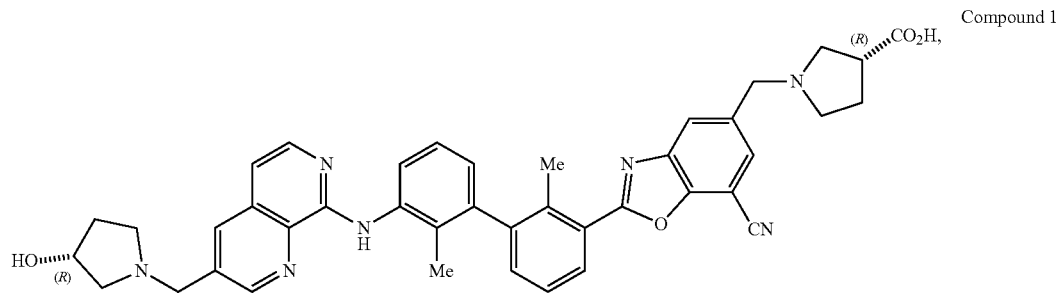

Compound 1 which is a tetrahydrofuran solvate, comprising: treating a solution of Compound 1 potassium salt:

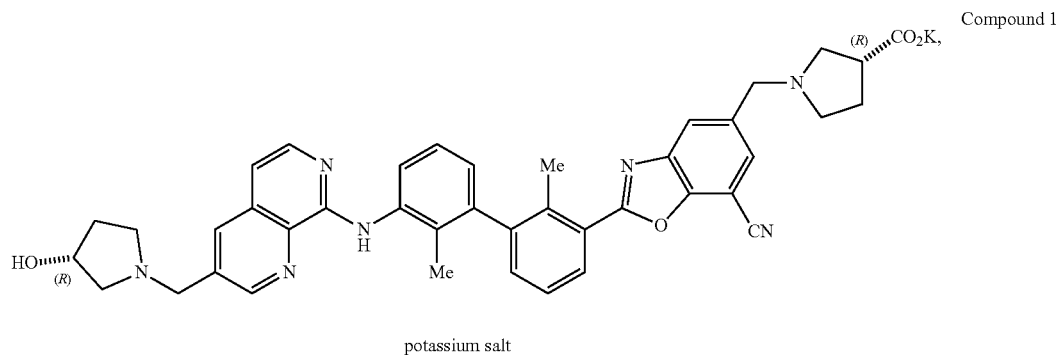

Compound 1 potassium salt and tetrahydrofuran with a metal scavenger and an ion exchange resin; and precipitating Form III of Compound 1. In some embodiments, the solution of Compound 1 potassium salt and tetrahydrofuran with a metal scavenger and an ion exchange resin further comprises a $C_{1-6}$ alcohol. In some embodiments, $C_{1-6}$ alcohol comprises methanol. In some embodiments, the solution of Compound 1 potassium salt and tetrahydrofuran with a metal scavenger and an ion exchange resin further comprises a $C_{1-6}$ alcohol. In some embodiments, $C_{1-6}$ alcohol comprises methanol. In some embodiments, the treating comprises heating the solution to a temperature of about 40° C. to about 65° C. to provide a heated solution. In some embodiments, the treating comprises heating the first solution to a temperature of about 50° C. to about 55° C. to provide a heated solution. In some embodiments, the treating comprises cooling the heated solution to room temperature; and after said cooling, filtering solution. In some embodiments, the treating comprises cooling the heated solution to room temperature; after said cooling, filtering solution; after said filtering, concentrating the solution; and cooling the concentrated solution to a temperature of about −30° C. to about −10° C. In some embodiments, the concentrated solution is cooled to a temperature of about −20° C. In some embodiments, the treating comprises cooling the heated solution to room temperature; after said cooling, filtering solution; after said filtering, concentrating the solution; cooling the concentrated solution to a temperature of about −30° C. to about −10° C.; and after said cooling, isolating solids. In some embodiments, the precipitating of Form III of Compound 1 comprises dissolving isolated solids in a solvent component to provide a solution; agitating the solution at room temperature for a period of time to provide a suspension; and collecting crystalline Form III of Compound 1 from the suspension.

In some embodiments, provided herein is a process of preparing a crystalline Form III of Compound 1:

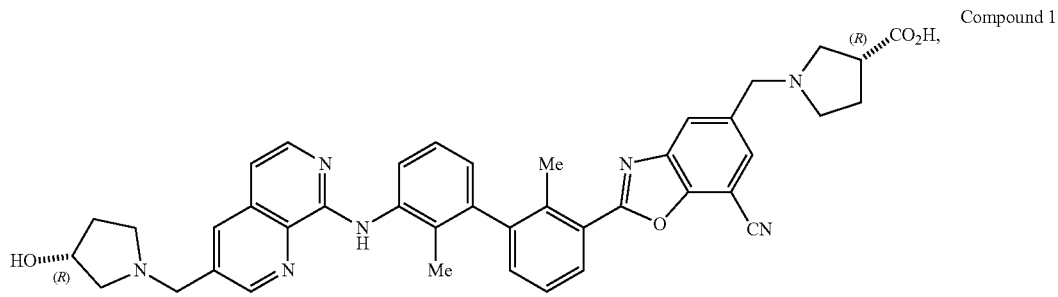

Compound 1 which is a tetrahydrofuran solvate, comprising preparing a first suspension of an amorphous Compound 1 in tetrahydrofuran. In some embodiments, the solvent component comprises an aprotic solvent and C$_{1-6}$ alcohol. In some embodiments, the solvent component comprises tetrahydrofuran and methanol. In some embodiments, the process comprises heating the first suspension to a temperature of about 50° C. to about 70° C. to provide a first solution. In some embodiments, the process comprises heating the first suspension to a temperature of about 60° C. to provide a first solution. In some embodiments, the process comprises cooling the first solution to a temperature of about 20° C. to about 40° C. to a second solution. In some embodiments, the process comprises cooling the first solution to a temperature of about 30° C. to a second solution. In some embodiments, the process comprises adding seed crystals of Form III to the second solution to provide a second suspension. In some embodiments, the process comprises cooling the second suspension to room temperature and agitating for a period of time to provide a third suspension; and collecting crystalline Form III of Compound 1 from the third suspension.

In some embodiments, provided herein is a process of preparing a crystalline Form IV of Compound 1:

which is a tetrahydrofuran solvate, comprising preparing a suspension of an amorphous Compound 1 in tetrahydrofuran. In some embodiments, the suspension of an amorphous Compound 1 in tetrahydrofuran further comprises a C$_{1-6}$ alcohol. In some embodiments, the C$_{1-6}$ alcohol comprises methanol. In some embodiments, the process comprises heating the suspension to a temperature of about 25° C. to about 50° C. to provide a solution. For example, the suspension is heated to a temperature of about 35° C. In some embodiments, the process comprises heating the suspension to a temperature of about 25° C. to about 50° C. to provide a solution; and concentrating the solution under reduced pressure. In some embodiments, the process comprises heating the suspension to a temperature of about 25° C. to about 50° C. to provide a solution; concentrating the solution under reduced pressure; and after said concentrating, adding tetrahydrofuran. In some embodiments, the process comprises heating the suspension to a temperature

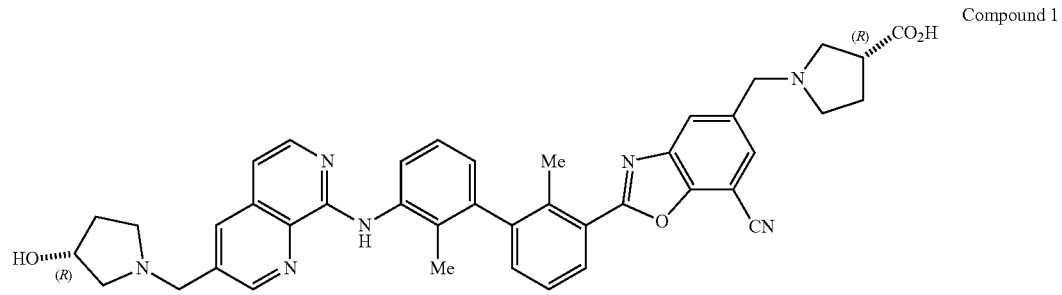

Compound 1 which is a non-solvate, comprising drying Form III for a period of time to reduce a tetrahydrofuran content of Form III to at least about 0.5 wt % to provide Form IV. In some embodiments, Form III is dried on a collection filter at ambient temperature for a period of time. In some embodiments, the period of time is about 12 hours to about 24 hours. In some embodiments, the period of time is about 2 days to about 8 days. In some embodiments, the period of time is about 3 days to about 6 days. In some embodiments, the form is dried at ambient temperature. In some embodiments, the process comprising drying Form III at room temperature for a period of time to reduce a tetrahydrofuran content of Form III to at least about 0.1 wt %.

In some embodiments, provided herein is a process of preparing a crystalline Form V of Compound 1:

of about 25° C. to about 50° C. to provide a solution; concentrating the solution under reduced pressure; after said concentrating, adding tetrahydrofuran; and after said adding, concentrating and cooling the solution to room temperature. In some embodiments, the process comprises heating the suspension to a temperature of about 25° C. to about 50° C. to provide a solution; concentrating the solution under reduced pressure; after said concentrating, adding tetrahydrofuran; after said adding, concentrating and cooling the solution to room temperature; and after said cooling, collecting crystalline Form V of Compound 1.

In some embodiments, provided herein a process of preparing an amorphous form of Compound 1:

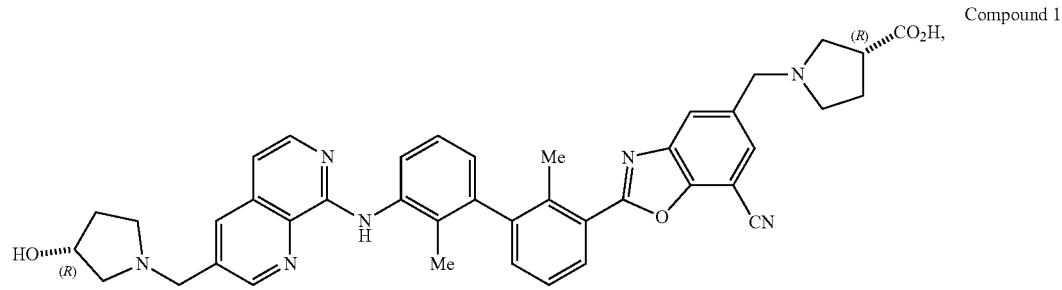

Compound 1

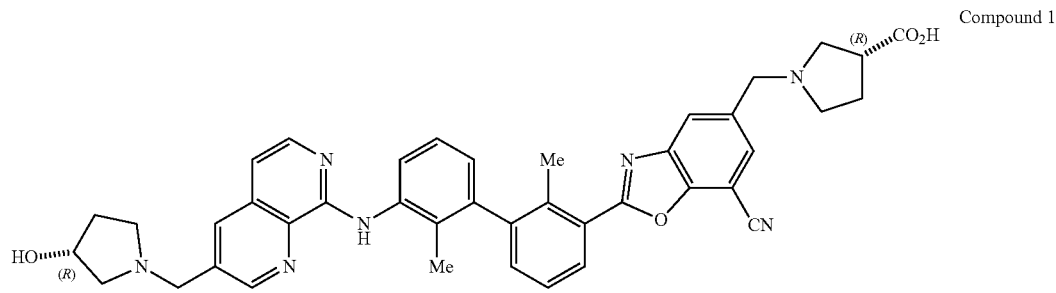

Compound 1 comprising converting Form I of Compound 1 to said amorphous form of Compound 1. In some embodiments, the converting comprises preparing a suspension of the Form I of Compound 1 in a solvent component. In some embodiments, the converting comprises preparing a suspension of the Form I of Compound 1 in a solvent component; heating the suspension to form a solution; after said heating, concentrating the heated solution. In some embodiments, the converting comprises preparing a suspension of the Form I of Compound 1 in a solvent component; heating the suspension to form a solution; after said heating, concentrating the solution; after said concentrating, adding the solution to a cold anti-solvent component to form a suspension of the amorphous form of Compound 1. In some embodiments, the converting comprises preparing a suspension of the Form I of Compound 1 in a solvent component; heating the suspension to a temperature of about 40° C. to about 80° C. to form a solution; after said heating, concentrating the solution; after said concentrating, adding the solution to a cold anti-solvent component at a temperature of about −10° C. to about 15° C. to form a suspension of the amorphous form of Compound 1. For example, the suspension is heated to a temperature of about 50° C. to about 60° C. or about 60° C. In some embodiments, the solution is added to a cold anti-solvent component at a temperature of about 0° C. to about 5° C. In some embodiments, the solvent component comprises an aprotic solvent and a $C_{1-6}$ alcohol. In some embodiments, the solvent component comprises tetrahydrofuran and methanol. In some embodiments, the cold anti-solvent component comprises a polar aprotic solvent. In some embodiments, the cold anti-solvent component comprises isopropyl acetate.

In some embodiments, provided herein is a process of preparing an amorphous form of Compound 1:

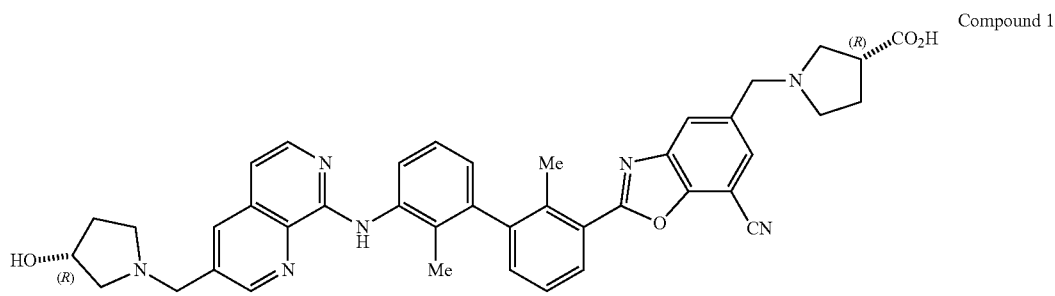

Compound 1 comprising converting Form III of Compound 1 to the amorphous form of Compound 1. In some embodiments, the converting comprises drying Form III at ambient temperature for about 12 hours to about 36 hours to provide dried Form IV with a tetrahydrofuran content of about 0.5 wt %. In some embodiments, the converting comprises drying Form III at ambient temperature for about 22 hours to provide dried Form IV with a tetrahydrofuran content of about 0.5 wt %. In some embodiments, the converting comprises adding water under reduced pressure to the dried Form IV. In some embodiments, the converting further comprises drying Form IV under reduced pressure at ambient temperature for about 6 to about 36 hours to provide amorphous form of Compound 1. In some embodiments, the converting comprises drying Form IV under reduced pressure at ambient temperature for about 12 to about 24 hours to provide amorphous form of Compound 1.

In some embodiments, provided herein is a process of preparing an amorphous form of Compound 1:

they have increased water solubility, translating to increased drug bioavailability. Forms that are weakly hygroscopic are desirable for their stability to heat and humidity and are resistant to degradation during long storage.

In some embodiments, a Compound 1 salt provided herein is crystalline. As used herein, "crystalline" or "crystalline form" is meant to refer to a certain lattice configuration of a crystalline substance. Different crystalline forms of the same substance typically have different crystalline lattices (e.g., unit cells) which are attributed to different physical properties that are characteristic of each of the crystalline forms. In some instances, different lattice configurations have different water or solvent content.

As used herein, "slurrying" is meant to refer to forming a mixture of insoluble matter in a liquid.

The different salt forms can be identified by solid state characterization methods such as by X-ray powder diffraction (XRPD). Other characterization methods such as differential scanning calorimetry (DSC), thermogravimetric

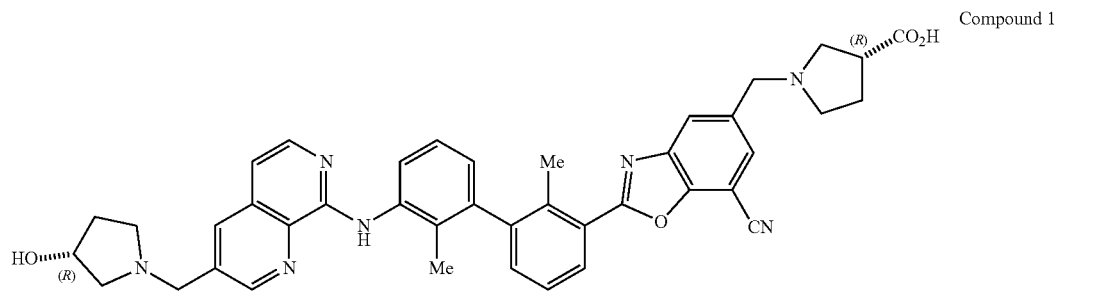

Compound 1 comprising converting Form V of Compound 1 to the amorphous form of Compound 1. In some embodiments, the converting comprises drying Form V of Compound 1 under reduced pressure and an inert atmosphere at elevated temperature. In some embodiments, the converting comprises drying Form V of Compound 1, comprising drying at atmospheric pressure and ambient temperature. In some embodiments, the converting comprises drying at reduced pressure and sweeping with an inert atmosphere at a temperature of about 50° C. to about 80° C. In some embodiments, the converting comprises drying at reduced pressure and sweeping with an inert atmosphere at a temperature of about 65° C.

In some embodiments, a method of inhibiting PD-1/PD-L1 interaction, said method comprising administering to a patient a crystalline form as described herein.

In some embodiments, a method of treating a disease or disorder associated with inhibition of PD-1/PD-L1 interaction, said method comprising administering to a patient in need thereof a therapeutically effective amount of a crystalline form as described herein.

In some embodiments, a method of enhancing, stimulating and/or increasing the immune response in a patient, said method comprising administering to the patient in need thereof a therapeutically effective amount of a crystalline form as described herein.

Different forms of the same substance have different bulk properties relating to, for example, hygroscopicity, solubility, stability, and the like. Forms with high melting points often have good thermodynamic stability which is advantageous in prolonging shelf-life drug formulations containing the solid form. Forms with lower melting points often are less thermodynamically stable, but are advantageous in that analysis (TGA), dynamic vapor sorption (DVS), solid state NMR, and the like further help identify the form as well as help determine stability and solvent/water content.

An XRPD pattern of reflections (peaks) is typically considered a fingerprint of a particular crystalline form. It is well known that the relative intensities of the XRPD peaks can widely vary depending on, inter alia, the sample preparation technique, crystal size distribution, various filters used, the sample mounting procedure, and the particular instrument employed. In some instances, new peaks may be observed or existing peaks may disappear, depending on the type of the instrument or the settings. As used herein, the term "peak" refers to a reflection having a relative height/intensity of at least about 4% of the maximum peak height/intensity. Moreover, instrument variation and other factors can affect the 2-theta values. Thus, peak assignments, such as those reported herein, can vary by plus or minus about 0.2° (2-theta), and the term "substantially" and "about" as used in the context of XRPD herein is meant to encompass the above-mentioned variations.

In the same way, temperature readings in connection with DSC, TGA, or other thermal experiments can vary about ±3° C. depending on the instrument, particular settings, sample preparation, etc. Accordingly, a crystalline form reported herein having a DSC thermogram "substantially" as shown in any of the Figures or the term "about" is understood to accommodate such variation.

In some embodiments, the term "about" means±10%. In some embodiments, the term "about" means±5%.

In some embodiments, the crystalline forms described herein are substantially isolated. By "substantially isolated" is meant that the crystalline forms is at least partially or substantially separated from the environment in which it was formed or detected. Partial separation can include, for example, a composition enriched in the crystalline forms described herein. Substantial separation can include compositions containing at least about 50%, at least about 60%, at least about 70%, at least about 80%, at least about 90%, at least about 95%, at least about 97%, or at least about 99% by weight of the crystalline forms described herein.

Crystalline forms of the invention can also include all isotopes of atoms occurring in the final crystalline forms of Compound 1. Isotopes include those atoms having the same atomic number but different mass numbers. For example, isotopes of hydrogen include tritium and deuterium.

In some embodiments, the crystalline forms can be found together with other substances such as water and solvents (e.g., hydrates and solvates) or can be isolated.

The phrase "pharmaceutically acceptable" is employed herein to refer to those crystalline forms, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Solid forms described herein also include pharmaceutically acceptable salts of the solid forms. As used herein, the term "pharmaceutically acceptable salt" refers to a salt formed by the addition of a pharmaceutically acceptable acid or base to a compound disclosed herein. As used herein, the phrase "pharmaceutically acceptable" refers to a substance that is acceptable for use in pharmaceutical applications from a toxicological perspective and does not adversely interact with the active ingredient. Pharmaceutically acceptable salts, including mono- and bi-salts, include, but are not limited to, those derived from organic and inorganic acids such as, but not limited to, acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in their entireties.

The crystalline form forming reactions described herein can be carried out at appropriate temperatures which can be readily determined by the skilled artisan. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures).

The expressions, "ambient temperature" and "room temperature" or "rt" as used herein, are understood in the art, and refer generally to a temperature, e.g., a reaction temperature, that is about the temperature of the room in which the salt forming reaction is carried out, for example, a temperature from about 20° C. to about 30° C.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. In some embodiments, reactions can be carried out in the absence of solvent, such as when at least one of the reagents is a liquid or gas.

Suitable solvents can include halogenated solvents such as carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, α,α,α-trifluorotoluene, 1,2-dichloroethane, 1,2-dibromoethane, hexafluorobenzene, 1,2,4-trichlorobenzene, 1,2-dichlorobenzene, chlorobenzene, fluorobenzene, mixtures thereof and the like.

Suitable solvents can include ether solvents such as: dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, t-butyl methyl ether, mixtures thereof and the like.

Suitable hydrocarbon solvents include benzene, cyclohexane, pentane, hexane, toluene, cycloheptane, methylcyclohexane, heptane (e.g., n-heptane), ethylbenzene, m-, o-, or p-xylene, octane, indane, nonane, naphthalene, mixtures thereof, and the like.

The term "$C_{1-6}$ alcohol" as used herein, refers to an alkyl group having 1 to 6 carbon atoms including one or more hydroxyl (OH) substituents. Examples of $C_{1-6}$ alcohol include, but are not limited to, methanol, ethanol, n-propanol, isopropanol, n-butanol and the like.

Suitable aprotic solvents can include, by way of example and without limitation, tetrahydrofuran (THF), N,N-dimethylformamide (DMF), N,N-dimethylacetamide (DMA), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, hexamethylphosphoramide, mixtures thereof, and the like.

The term "anti-solvent" as used herein, refers to solvents in which a chemical compound is sparingly soluble. Anti-solvents may be used to achieve supersaturation and solidification by exposing a solution of a product to another solvent(s) in which the product is sparingly soluble.

The crystalline form forming reactions described herein can be carried out in air or under an inert atmosphere. Typically, reactions containing reagents or products that are substantially reactive with air can be carried out using air-sensitive synthetic techniques that are well known to the skilled artisan.

Methods of Use

Crystalline forms of the present disclosure can inhibit the activity of PD-1/PD-L1 protein/protein interaction and, thus, are useful in treating diseases and disorders associated with activity of PD-1 and the diseases and disorders associated with PD-L1 including its interaction with other proteins such as PD-1 and B7-1 (CD80). In certain embodiments, the crystalline forms of the present disclosure are useful for therapeutic administration to enhance, stimulate and/or increase immunity in cancer, chronic infection or sepsis, including enhancement of response to vaccination. In some embodiments, the present disclosure provides a method for inhibiting the PD-1/PD-L1 protein/protein interaction. The method includes administering to an individual or a patient a crystalline forms of Compound 1 or a pharmaceutically acceptable salt or a stereoisomer thereof. The crystalline forms of the present disclosure can be used alone, in combination with other agents or therapies or as an adjuvant or neoadjuvant for the treatment of diseases or disorders, including cancer or infection diseases. For the uses described herein, any of the crystalline forms of the disclosure, including any of the embodiments thereof, may be used.

The crystalline forms of the present disclosure inhibit the PD-1/PD-L1 protein/protein interaction, resulting in a PD-1 pathway blockade. The blockade of PD-1 can enhance the immune response to cancerous cells and infectious diseases in mammals, including humans. In some embodiments, the present disclosure provides treatment of an individual or a patient in vivo using a crystalline form of Compound 1 such that growth of cancerous tumors is inhibited. A crystalline form of Compound 1 can be used to inhibit the growth of cancerous tumors. Alternatively, a crystalline form of Compound 1 can be used in conjunction with other agents or standard cancer treatments, as described below. In one embodiment, the present disclosure provides a method for inhibiting growth of tumor cells in vitro. The method includes contacting the tumor cells in vitro with a crystalline form of Compound 1. In another embodiment, the present disclosure provides a method for inhibiting growth of tumor cells in an individual or a patient. The method includes administering to the individual or patient in need thereof a therapeutically effective amount of a crystalline form of Compound 1.

In some embodiments, provided herein is a method for treating cancer. The method includes administering to a patient in need thereof, a therapeutically effective amount of a crystalline form of Compound 1. Examples of cancers include those whose growth may be inhibited using crystalline forms of the disclosure and cancers typically responsive to immunotherapy.

In some embodiments, the present disclosure provides a method of enhancing, stimulating and/or increasing the immune response in a patient. The method includes administering to the patient in need thereof a therapeutically effective amount of a crystalline form of Compound 1.

Examples of cancers that are treatable using the crystalline forms of the present disclosure include, but are not limited to, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, endometrial cancer, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The crystalline forms of the present disclosure are also useful for the treatment of metastatic cancers, especially metastatic cancers that express PD-L1.

In some embodiments, cancers treatable with crystalline forms of the present disclosure include melanoma (e.g., metastatic malignant melanoma, cutaneous melanoma), renal cancer (e.g., clear cell carcinoma), prostate cancer (e.g., hormone refractory prostate adenocarcinoma), breast cancer (e.g., breast invasive carcinoma), colon cancer, lung cancer (e.g., non-small cell lung cancer and small cell lung cancer), squamous cell head and neck cancer (e.g., squamous cell carcinoma of the head and neck), urothelial cancer (e.g., bladder cancer, nonmuscle invasive bladder cancer (NMIBC)) and cancers with high microsatellite instability ($MSI^{high}$). Additionally, the disclosure includes refractory or recurrent malignancies whose growth may be inhibited using the crystalline forms of the disclosure.

In some embodiments, cancers that are treatable using the crystalline forms of the present disclosure include, but are not limited to, solid tumors (e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head and neck, thyroid cancer, glioblastoma, sarcoma, bladder cancer, etc.), hematological cancers (e.g., lymphoma, leukemia such as acute lymphoblastic leukemia (ALL), acute myelogenous leukemia (AML), chronic lymphocytic leukemia (CLL), chronic myelogenous leukemia (CML), DLBCL, mantle cell lymphoma, Non-Hodgkin lymphoma (including relapsed or refractory NHL and recurrent follicular), Hodgkin lymphoma or multiple myeloma) and combinations of said cancers.

In some embodiments, cancers that are treatable using the crystalline forms of the present disclosure include, but are not limited to, cholangiocarcinoma, bile duct cancer, biliary tract cancer, triple negative breast cancer, rhabdomyosarcoma, small cell lung cancer, leiomyosarcoma, hepatocellular carcinoma, Ewing's sarcoma, brain cancer, brain tumor, astrocytoma, neuroblastoma, neurofibroma, basal cell carcinoma, chondrosarcoma, epithelioid sarcoma, eye cancer, Fallopian tube cancer, gastrointestinal cancer, gastrointestinal stromal tumors, hairy cell leukemia, intestinal cancer, islet cell cancer, oral cancer, mouth cancer, throat cancer, laryngeal cancer, lip cancer, mesothelioma, neck cancer, nasal cavity cancer, ocular cancer, ocular melanoma, pelvic cancer, rectal cancer, renal cell carcinoma, salivary gland cancer, sinus cancer, spinal cancer, tongue cancer, tubular carcinoma, urethral cancer, and ureteral cancer.

In some embodiments, the crystalline forms of the present disclosure can be used to treat sickle cell disease and sickle cell anemia.

In some embodiments, diseases and indications that are treatable using the crystalline forms of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), and essential thrombocytosis (ET)), myelodysplasia syndrome (MDS), T-cell acute lymphoblastic lymphoma (T-ALL) and multiple myeloma (MM).

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, and teratoma.

Exemplary lung cancers include non-small cell lung cancer (NSCLC) (e.g., squamous cell NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, and mesothelioma.

Exemplary gastrointestinal cancers include cancers of the esophagus (carcinoma, squamous cell carcinoma, adenocarcinoma, leiomyosarcoma, lymphoma), stomach (carcinoma, lymphoma, leiomyosarcoma, adenocarcinoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer (e.g., colorectal adenocarcinoma).

Exemplary genitourinary tract cancers include cancers of the kidney (adenocarcinoma, Wilm's tumor [nephroblastoma]), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma). In some embodiments, the cancer is a urological cancer (e.g., papillary kidney carcinoma, testicular germ cell cancer, chromophobe renal cell carcinoma, clear cell renal carcinoma, or prostate adenocarcinoma).

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors.

Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors), and spinal cord (neurofibroma, meningioma, glioma, sarcoma), as well as neuroblastoma and Lhermitte-Duclos disease.

Exemplary gynecological cancers include cancers of the uterus (endometrial carcinoma), cervix (cervical carcinoma, pre-tumor cervical dysplasia), ovaries (ovarian carcinoma (serous cystadenocarcinoma, serous adenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma (e.g., cutaneous squamous cell carcinoma), Kaposi's sarcoma, moles dysplastic nevi, lipoma, angioma, dermatofibroma, and keloids. In some embodiments, diseases and indications that are treatable using the crystalline forms of the present disclosure include, but are not limited to, sickle cell disease (e.g., sickle cell anemia), triple-negative breast cancer (TNBC), myelodysplastic syndromes, testicular cancer, bile duct cancer, esophageal cancer, and urothelial carcinoma.

PD-1 pathway blockade with crystalline forms of the present disclosure can also be used for treating infections such as viral, bacteria, fungus and parasite infections. The present disclosure provides a method for treating infections such as viral infections. The method includes administering to a patient in need thereof, a therapeutically effective amount of a crystalline form of Compound 1. Examples of viruses causing infections treatable by methods of the present disclosure include, but are not limited to, human immunodeficiency virus, human papillomavirus, influenza, hepatitis A, B, C or D viruses, adenovirus, poxvirus, herpes simplex viruses, human cytomegalovirus, severe acute respiratory syndrome virus, ebola virus, and measles virus. In some embodiments, viruses causing infections treatable by methods of the present disclosure include, but are not limited to, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus, tuberculosis and arboviral encephalitis virus.

The present disclosure provides a method for treating bacterial infections. The method includes administering to a patient in need thereof, a therapeutically effective amount of a crystalline form of Compound 1. Non-limiting examples of pathogenic bacteria causing infections treatable by methods of the disclosure include chlamydia, rickettsial bacteria, mycobacteria, staphylococci, streptococci, pneumococci, meningococci and conococci, klebsiella, proteus, serratia, pseudomonas, legionella, diphtheria, salmonella, bacilli, cholera, tetanus, botulism, anthrax, plague, leptospirosis, and Lyme's disease bacteria.

The present disclosure provides a method for treating fungus infections. The method includes administering to a patient in need thereof, a therapeutically effective amount of a crystalline form of Compound 1. Non-limiting examples of pathogenic fungi causing infections treatable by methods of the disclosure include *Candida* (*albicans, krusei, glabrata, tropicalis,* etc.), *Cryptococcus neoformans, Aspergillus* (*fumigatus, niger,* etc.), Genus Mucorales (*mucor, absidia,* rhizophus), *Sporothrix schenkii, Blastomyces dermatitidis, Paracoccidioides brasiliensis, Coccidioides immitis* and *Histoplasma capsulatum.*

The present disclosure provides a method for treating parasite infections. The method includes administering to a patient in need thereof, a therapeutically effective amount of a crystalline form of Compound 1. Non-limiting examples of pathogenic parasites causing infections treatable by methods of the disclosure include *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Try-*

*panosoma cruzi, Leishmania donovani, Toxoplasma gondi,* and *Nippostrongylus brasiliensis.*

The present disclosure provides a method for treating neurodegenerative diseases or disorders. The method includes administering to a patient in need thereof, a therapeutically effective amount of a crystalline form of Compound 1. Non-limiting examples of neurodegenerative diseases or disorders include Alzheimer's disease, Parkinson's disease, Huntington's disease, prion disease, Motor neurone diseases, Spinocerebellar ataxia and Spinal muscular atrophy.

It is believed that crystalline forms of Compound 1, or any of the embodiments thereof, may possess satisfactory pharmacological profile and promising biopharmaceutical properties, such as toxicological profile, metabolism and pharmacokinetic properties, solubility, and permeability. It will be understood that determination of appropriate biopharmaceutical properties is within the knowledge of a person skilled in the art, e.g., determination of cytotoxicity in cells or inhibition of certain targets or channels to determine potential toxicity.

The terms "individual" or "patient," used interchangeably, refer to any animal, including mammals, preferably mice, rats, other rodents, rabbits, dogs, cats, swine, cattle, sheep, horses, or primates, and most preferably humans.

The phrase "therapeutically effective amount" refers to the amount of active crystalline form that elicits the biological or medicinal response in a tissue, system, animal, individual or human that is being sought by a researcher, veterinarian, medical doctor or other clinician.

As used herein, the term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the crystalline forms of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

Combination Therapies

Immune-Checkpoint Therapies

Crystalline forms of the present disclosure can be used in combination with one or more immune checkpoint inhibitors for the treatment of diseases, such as cancer or infections. Exemplary immune checkpoint inhibitors include inhibitors against immune checkpoint molecules such as CBL-B, CD20, CD122, CD96, CD73, CD47, CSF1R, JAK, PI3K delta, PI3K gamma, TAM, arginase, HPK1, A2AR, B7-H3, B7-H4, BTLA, CTLA-4, LAG3, TIM3, TIGIT, CD112R, VISTA, PD-1, PD-L1 and PD-L2. In some embodiments, the immune checkpoint molecule is a stimulatory checkpoint molecule selected from CD27, CD28, CD40, ICOS, OX40, GITR and CD137 (4-1BB). In some embodiments, the immune checkpoint molecule is an inhibitory checkpoint molecule selected from A2AR, B7-H3, B7-H4, BTLA, CTLA-4, IDO, KIR, LAG3, PD-1, TIM3, TIGIT, and VISTA. In some embodiments, the crystalline forms provided herein can be used in combination with one or more agents selected from KIR inhibitors, TIGIT inhibitors, LAIR1 inhibitors, CD160 inhibitors, 2B4 inhibitors and TGF beta inhibitors.

In some embodiments, the crystalline forms provided herein can be used in combination with one or more agonists of immune checkpoint molecules, e.g., OX40, CD27, GITR, and CD137 (also known as 4-1BB).

In some embodiments, the agonist of an immune checkpoint molecule is an agonist of OX40, CD27, CD28, GITR, ICOS, CD40, TLR7/8, and CD137 (also known as 4-1BB).

In some embodiments, the agonist of CD137 is urelumab. In some embodiments, the agonist of CD137 is utomilumab.

In some embodiments, the agonist of an immune checkpoint molecule is an agonist of CD40. In some embodiments, the agonist of CD40 is CP-870893, ADC-1013, CDX-1140, SEA-CD40, RO7009789, JNJ-64457107, APX-005M, or Chi Lob 7/4.

In some embodiments, the agonist of an immune checkpoint molecule is an agonist of ICOS. In some embodiments, the agonist of ICOS is GSK-3359609, JTX-2011, or MEDI-570.

In some embodiments, the agonist of an immune checkpoint molecule is an agonist of CD28. In some embodiments, the agonist of CD28 is theralizumab.

In some embodiments, the agonist of an immune checkpoint molecule is an agonist of CD27. In some embodiments, the agonist of CD27 is varlilumab.

In some embodiments, the agonist of an immune checkpoint molecule is an agonist of TLR7/8. In some embodiments, the agonist of TLR7/8 is MEDI9197.

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, cemiplimab, spartalizumab, camrelizumab, cetrelimab, toripalimab, sintilimab, SHR-1210, PDR001, MGA012, PDR001, AB122, AMP-224, JTX-4014, BGB-108, BCD-100, BAT1306, LZM009, AK105, HLX10, or TSR-042. In some embodiments, the anti-PD-1 monoclonal antibody is nivolumab or pembrolizumab. In some embodiments, the anti-PD1 antibody is pembrolizumab. In some embodiments, the anti-PD-1 monoclonal antibody is MGA012. In some embodiments, the anti-PD1 antibody is SHR-1210. Other anti-cancer agent (s) include antibody therapeutics such as 4-1BB (e.g. urelumab, utomilumab).

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), durvalumab (Imfinzi®), atezolizumab (Tecentriq®), Avelumab (Bavencio®), MSB0010718C, tislelizumab, FAZ053, KN035, CS1001, SHR-1316, CBT-502, A167, STI-A101, CK-301, BGB-A333, MSB-2311, HLX20, or LY3300054. In some embodiments, the anti-PD-L1 monoclonal antibody is MPDL3280A or MEDI4736.

In some embodiments, the inhibitor of an immune checkpoint molecule is an inhibitor of PD-1 and PD-L1, e.g., an anti-PD-1/PD-L1 bispecific antibody. In some embodiments, the anti-PD-1/PD-L1 bispecific antibody is MCLA-136.

In some embodiments, the inhibitor is MCLA-145.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of PD-1 and CTLA-4, e.g., an anti-PD-1/CTLA-4 bispecific antibody. In some embodiments, the anti-PD-1/CTLA-4 antibody is AK104.

In some embodiments, the inhibitor of an immune checkpoint molecule is an inhibitor of LAG3, e.g., an anti-LAG3 antibody. In some embodiments, the anti-LAG3 antibody is BMS-986016, LAG525, INCAGN2385, or eftilagimod alpha (IMP321).

In some embodiments, the inhibitor of an immune checkpoint molecule is an inhibitor of CD73. In some embodiments, the inhibitor of CD73 is oleclumab. In some embodiments, the inhibitor of CD73 is MEDI9447.

In some embodiments, the inhibitor of an immune checkpoint molecule is an inhibitor of TIGIT. In some embodiments, the inhibitor of TIGIT is OMP-31M32.

In some embodiments, the inhibitor of an immune checkpoint molecule is an inhibitor of VISTA. In some embodiments, the inhibitor of VISTA is JNJ-61610588 or CA-170.

In some embodiments, the inhibitor of an immune checkpoint molecule is an inhibitor of B7-H3. In some embodiments, the inhibitor of B7-H3 is enoblituzumab, MGD009, or 8H9.

In some embodiments, the inhibitor of an immune checkpoint molecule is an inhibitor of KIR. In some embodiments, the inhibitor of KIR is lirilumab or IPH4102.

In some embodiments, the inhibitor of an immune checkpoint molecule is an inhibitor of A2aR. In some embodiments, the inhibitor of A2aR is CPI-444.

In some embodiments, the inhibitor of an immune checkpoint molecule is an inhibitor of TGF-beta. In some embodiments, the inhibitor of TGF-beta is trabedersen, galusertinib, or M7824.

In some embodiments, the inhibitor of an immune checkpoint molecule is an inhibitor of PI3K-gamma. In some embodiments, the inhibitor of PI3K-gamma is IPI-549.

In some embodiments, the inhibitor of an immune checkpoint molecule is an inhibitor of CD47. In some embodiments, the inhibitor of CD47 is Hu5F9-G4 or TTI-621.

In some embodiments, the inhibitor of an immune checkpoint molecule is an inhibitor of CD70. In some embodiments, the inhibitor of CD70 is cusatuzumab or BMS-936561.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the agonist of an immune checkpoint molecule is an agonist of GITR, e.g., an anti-GITR antibody. In some embodiments, the agonist is TRX518, MK-4166, INCAGN1876, MK-1248, AMG228, BMS-986156, GWN323, MEDI1873, or MEDI6469.

In some embodiments, the agonist of an immune checkpoint molecule is an agonist of OX40, e.g., OX40 agonist antibody or OX40L fusion protein. In some embodiments, the anti-OX40 antibody is MEDI0562, MOXR-0916, PF-04518600, GSK3174998, BMS-986178, or 9B12. In some embodiments, the OX40L fusion protein is MEDI6383.

In some embodiments, the inhibitor of an immune checkpoint molecule is an inhibitor of CD20, e.g., an anti-CD20 antibody. In some embodiments, the anti-CD20 antibody is obinutuzumab or rituximab.

The crystalline forms of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor. In some embodiments, the bispecific antibody binds to PD-1 and PD-L1. In some embodiments, the bispecific antibody that binds to PD-1 and PD-L1 is MCLA-136. In some embodiments, the bispecific antibody binds to PD-L1 and CTLA-4. In some embodiments, the bispecific antibody that binds to PD-L1 and CTLA-4 is AK104.

In some embodiments, the crystalline forms of the disclosure can be used in combination with one or more metabolic enzyme inhibitors. In some embodiments, the metabolic enzyme inhibitor is an inhibitor of IDOL TDO, or arginase. Examples of IDO1 inhibitors include epacadostat, NLG919, BMS-986205, PF-06840003, IOM2983, RG-70099 and LY338196.

As provided throughout, the additional compounds, inhibitors, agents, etc. can be combined with the present crystalline form in a single or continuous dosage form, or they can be administered simultaneously or sequentially as separate dosage forms.

Cancer Therapies

Cancer cell growth and survival can be impacted by dysfunction in multiple biological pathways. Thus, it may be useful to combine inhibitors of different mechanisms, such as enzyme inhibitors, signal transduction inhibitors, inhibitors of chromatin dynamics or modulators of immune responses, to treat such conditions. Targeting more than one signaling pathway (or more than one biological molecule involved in a given signaling pathway) may reduce the likelihood of drug-resistance arising in a cell population, or reduce the toxicity of treatment.

The crystalline forms of the present disclosure can be used in combination with one or more other therapies for the treatment of diseases, such as cancer or infections. Examples of diseases and indications treatable with combination therapies include those as described herein. Examples of cancers include solid tumors and non-solid tumors, such as liquid tumors, blood cancers. Examples of infections include viral infections, bacterial infections, fungus infections or parasite infections. For example, the crystalline forms of the present disclosure can be combined with one or more inhibitors of the following kinases for the treatment of cancer: Akt1, Akt2, Akt3, BCL2, CDK, TGF-βR, PKA, PKG, PKC, CaM-kinase, phosphorylase kinase, MEKK, ERK, MAPK, mTOR, EGFR, HER2, HER3, HER4, INS-R, IDH2, IGF-1R, IR-R, PDGFαR, PDGFβR, PI3K (alpha, beta, gamma, delta, and multiple or selective), CSF1R, KIT, FLK-II, KDR/FLK-1, FLK-4, flt-1, FGFR1, FGFR2, FGFR3, FGFR4, c-Met, PARP, Ron, Sea, TRKA, TRKB, TRKC, TAM kinases (Axl, Mer, Tyro3), FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf.

In some embodiments, the crystalline forms of the present disclosure can be combined with one or more of the following inhibitors for the treatment of cancer or infections. Non-limiting examples of inhibitors that can be combined with the crystalline forms of the present disclosure for treatment of cancer and infections include an FGFR inhibitor (FGFR1, FGFR2, FGFR3 or FGFR4, e.g., pemigatinib (INCB054828), INCB62079), an EGFR (also known as ErB-1 or HER-1) inhibitor (e.g., erlotinib, gefitinib, vandetanib, orsimertinib, cetuximab, necitumumab, or panitumumab), a VEGFR inhibitor or pathway blocker (e.g., bevacizumab, pazopanib, sunitinib, sorafenib, axitinib, regorafenib, ponatinib, cabozantinib, vandetanib, ramucirumab, lenvatinib, ziv-aflibercept), a PARP inhibitor (e.g., olaparib, rucaparib, veliparib or niraparib), a JAK inhibitor (JAK1 and/or JAK2, e.g., ruxolitinib, baricitinib or itacitinib (INCB39110)), an IDO inhibitor (e.g., epacadostat, NLG919, or BMS-986205, MK7162), an LSD1 inhibitor (e.g., INCB59872 and INCB60003), a TDO inhibitor, a PI3K-delta inhibitor (e.g., Parsaclisib (INCB50465) and INCB50797), a PI3K-gamma inhibitor such as PI3K-gamma selective inhibitor, a Pim inhibitor (e.g., INCB53914), an EGFR inhibitor (also known as ErB-1 or HER-1; e.g., erlotinib, gefitinib, vandetanib, orsimertinib, cetuximab, necitumumab, or panitumumab), a VEGFR inhibitor or pathway blocker (e.g., bevacizumab, pazopanib, sunitinib, sorafenib, axitinib, regorafenib, ponatinib, cabozantinib, vandetanib, ramucirumab, lenvatinib, ziv-aflibercept), a PARP inhibitor (e.g., olaparib, rucaparib, veliparib, talazoparib, or niraparib), a CSF1R inhibitor, a TAM receptor tyrosine kinase (Tyro-3, Axl, and Mer), an adenosine receptor antagonist (e.g., A2a/A2b receptor antagonist), an HPK1 inhibitor, a chemokine receptor inhibitor (e.g., CCR2 or CCR5 inhibitor), a SHP1/2 phosphatase inhibitor, a histone deacetylase inhibitor (HDAC) such as an HDAC8 inhibitor, an angiogenesis inhibitor, an interleukin receptor inhibitor, bromo and extra terminal family members inhibitors (for example, bromodomain inhibitors or BET inhibitors such as INCB54329 and INCB57643), an arginase inhibitor (INCB001158), a PARP inhibitor (such as rucaparib or olaparib), sitravatinib, a B-Raf inhibitor-MEK inhibitor combination (such as encorafenib plus binimetinib, dabrafenib plus trametinib, or cobimetinib plus vemurafenib), and an adenosine receptor antagonist or combinations thereof.

In some embodiments, the v of the present disclosure can be combined with a TLR7 agonist (e.g., imiquimod).

The crystalline forms of the present disclosure can further be used in combination with other methods of treating cancers, for example by chemotherapy, irradiation therapy, tumor-targeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, bispecific or multi-specific antibody, antibody drug conjugate, adoptive T cell transfer, Toll receptor agonists, STING agonists, RIG-I agonists, oncolytic virotherapy and immunomodulating small molecules, including thalidomide or JAK1/2 inhibitor, PI3Kδ inhibitor and the like. The crystalline forms can be administered in combination with one or more anti-cancer drugs, such as a chemotherapeutic agent. Examples of chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, baricitinib, bleomycin, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat and zoledronate.

Other anti-cancer agent(s) include antibody therapeutics such as trastuzumab (Herceptin), antibodies to costimulatory molecules such as CTLA-4 (e.g., ipilimumab), 4-1BB (e.g., urelumab, utomilumab), antibodies to PD-1 and PD-L1, or antibodies to cytokines (IL-10, TGF-β, etc.). Examples of antibodies to PD-1 and/or PD-L1 that can be combined with crystalline forms of the present disclosure for the treatment of cancer or infections such as viral, bacteria, fungus and parasite infections include, but are not limited to nivolumab, pembrolizumab, atezolizumab, durvalumab, avelumab and SHR-1210.

The crystalline forms of the present disclosure can further be used in combination with one or more anti-inflammatory agents, steroids, immunosuppressants or therapeutic antibodies.

The crystalline forms of Compound 1 can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The crystalline forms of Compound 1 can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the crystalline forms of the present disclosure can be used in combination with tumor specific antigen such as heat shock proteins isolated from tumor tissue itself. In some embodiments, the crystalline forms of Compound 1 can be combined with dendritic cells immunization to activate potent anti-tumor responses.

The crystalline forms of the present disclosure can be used in combination with bispecific macrocyclic peptides that target Fe alpha or Fe gamma receptor-expressing effectors cells to tumor cells. The v of the present disclosure can also be combined with macrocyclic peptides that activate host immune responsiveness.

The crystalline forms of the present disclosure can be used in combination with bone marrow transplant for the treatment of a variety of tumors of hematopoietic origin.

The crystalline forms of Compound 1 can be used in combination with vaccines, to stimulate the immune response to pathogens, toxins, and self antigens. Examples of pathogens for which this therapeutic approach may be particularly useful, include pathogens for which there is currently no effective vaccine, or pathogens for which conventional vaccines are less than completely effective. These include, but are not limited to, HIV, Hepatitis (A, B, & C), Influenza, Herpes, *Giardia*, Malaria, *Leishmania, Staphylococcus aureus, Pseudomonas Aeruginosa*.

Viruses causing infections treatable by methods of the present disclosure include, but are not limited to human papillomavirus, influenza, hepatitis A, B, C or D viruses, adenovirus, poxvirus, herpes simplex viruses, human cytomegalovirus, severe acute respiratory syndrome virus, ebola virus, measles virus, herpes virus (e.g., VZV, HSV-1, HAV-6, HSV-II, and CMV, Epstein Barr virus), flaviviruses, echovirus, rhinovirus, coxsackie virus, coronavirus, respiratory syncytial virus, mumpsvirus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Pathogenic bacteria causing infections treatable by methods of the disclosure include, but are not limited to, *chlamydia*, rickettsial bacteria, mycobacteria, staphylococci, streptococci, pneumococci, meningococci and conococci, *klebsiella, proteus, serratia, pseudomonas, legionella*, diphtheria, *salmonella*, bacilli, cholera, tetanus, botulism, anthrax, plague, leptospirosis, and Lyme's disease bacteria.

Pathogenic fungi causing infections treatable by methods of the disclosure include, but are not limited to, *Candida* (*albicans, krusei, glabrata, tropicalis*, etc.), *Cryptococcus neoformans, Aspergillus* (*fumigatus, niger*, etc.), Genus Mucorales (*mucor, absidia*, rhizophus), *Sporothrix schenkii, Blastomyces dermatitidis, Paracoccidioides brasiliensis, Coccidioides immitis* and *Histoplasma capsulatum*.

Pathogenic parasites causing infections treatable by methods of the disclosure include, but are not limited to, *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*.

When more than one pharmaceutical agent is administered to a patient, they can be administered simultaneously, separately, sequentially, or in combination (e.g., for more than two agents).

Formulation, Dosage Forms and Administration

When employed as pharmaceuticals, the crystalline forms of the present disclosure can be administered in the form of pharmaceutical compositions. Thus the present disclosure provides a composition comprising a crystalline forms of Compound 1 or any of the embodiments thereof, and at least one pharmaceutically acceptable carrier or excipient. These compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the crystalline form of the present disclosure, in combination with one or more pharmaceutically acceptable carriers or excipients. In some embodiments, the composition is suitable for topical administration. In making the compositions of the invention, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active crystalline form, soft and hard gelatin capsules, suppositories, sterile injectable solutions and sterile packaged powders.

In preparing a formulation, the active crystalline form can be milled to provide the appropriate particle size prior to combining with the other ingredients. If the active crystalline form is substantially insoluble, it can be milled to a particle size of less than 200 mesh. If the active crystalline form is substantially water soluble, the particle size can be adjusted by milling to provide a substantially uniform distribution in the formulation, e.g., about 40 mesh.

The crystalline forms of the invention may be milled using known milling procedures such as wet milling to obtain a particle size appropriate for tablet formation and for other formulation types. Finely divided (nanoparticulate) preparations of the crystalline forms of the invention can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one crystalline form described herein. In some embodiments, the silicified microcrystalline cellulose comprises about 98% microcrystalline cellulose and about 2% silicon dioxide w/w.

In some embodiments, the composition is a sustained release composition comprising at least one crystalline form described herein, and at least one pharmaceutically acceptable carrier or excipient. In some embodiments, the composition comprises at least one crystalline form described herein, and at least one component selected from microcrystalline cellulose, lactose monohydrate, hydroxypropyl methylcellulose and polyethylene oxide. In some embodiments, the composition comprises at least one crystalline form described herein, and microcrystalline cellulose, lactose monohydrate and hydroxypropyl methylcellulose. In some embodiments, the composition comprises at least one crystalline forms described herein, and microcrystalline cellulose, lactose monohydrate and polyethylene oxide. In some embodiments, the composition further comprises magnesium stearate or silicon dioxide. In some embodiments, the microcrystalline cellulose is Avicel PH102™ In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel K00LV™). In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The crystalline form may be effective over a wide dosage range and is generally administered in a therapeutically effective amount. It will be understood, however, that the amount of the crystalline form actually administered will usually be determined by a physician, according to the relevant circumstances, including the condition to be treated, the chosen route of administration, the actual crystalline form administered, the age, weight, and response of the individual patient, the severity of the patient's symptoms and the like.

The therapeutic dosage of a crystalline form of the present invention can vary according to, e.g., the particular use for which the treatment is made, the manner of administration of the crystalline form, the health and condition of the patient, and the judgment of the prescribing physician. The proportion or concentration of a crystalline form of the invention in a pharmaceutical composition can vary depending upon a number of factors including dosage, chemical characteristics (e.g., hydrophobicity), and the route of administration. For example, the crystalline forms of the invention can be provided in an aqueous physiological buffer solution containing about 0.1 to about 10% w/v of the crystalline form for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the crystalline form selected, formulation of the excipient, and its route of administration. Effective doses can be extrapolated from dose-response curves derived from in vitro or animal model test systems.

For preparing solid compositions such as tablets, the principal active ingredient is mixed with a pharmaceutical excipient to form a solid preformulation composition containing a homogeneous mixture of a crystalline form of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, e.g., about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the crystalline forms and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose, and the like. In some embodiments, topical formulations contain at least about 0.1, at least about 0.25, at least about 0.5, at least about 1, at least about 2 or at least about 5 wt % of the crystalline form of the invention. The topical formulations can be suitably packaged in tubes of, e.g., 100 g which are optionally associated with instructions for the treatment of the select indication, e.g., psoriasis or other skin condition.

The amount of crystalline form or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the preparations typically will be between 3 and 11, more preferably from 5 to 9 and most preferably from 7 to 8.

The therapeutic dosage of a crystalline form of the present invention can vary according to, e.g., the particular use for which the treatment is made, the manner of administration of the crystalline form, the health and condition of the patient, and the judgment of the prescribing physician. The proportion or concentration of a crystalline form of the invention in a pharmaceutical composition can vary depending upon a number of factors including dosage, chemical characteristics (e.g., hydrophobicity), and the route of administration. For example, the crystalline forms of the invention can be provided in an aqueous physiological buffer solution containing about 0.1 to about 10% w/v of the crystalline form for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the crystalline form selected, formulation of the excipient, and its route of administration. Effective doses can be extrapolated from dose-response curves derived from in vitro or animal model test systems.

Labeled Compounds and Assay Methods

The crystalline forms of the present disclosure can further be useful in investigations of biological processes in normal and abnormal tissues. Thus, another aspect of the present invention relates to labeled crystalline forms of the invention (radio-labeled, fluorescent-labeled, etc.) that would be useful not only in imaging techniques but also in assays, both in vitro and in vivo, for localizing and quantitating PD-1 or PD-L1 protein in tissue samples, including human, and for identifying PD-L1 ligands by inhibition binding of a labeled compound. Accordingly, the present invention includes PD-1/PD-L1 binding assays that contain such labeled crystalline forms.

The present invention further includes isotopically-substituted crystalline forms of the disclosure. An "isotopically-substituted" crystalline form is a crystalline form of the invention where one or more atoms are replaced or substituted by an atom having the same atomic number but a different atomic mass or mass number, e.g., a different atomic mass or mass number from the atomic mass or mass number typically found in nature (i.e., naturally occurring). It is to be understood that a "radio-labeled" crystalline form is a crystalline form that has incorporated at least one isotope that is radioactive (e.g., radionuclide). Suitable radionuclides that may be incorporated in crystalline forms of the present invention include but are not limited to $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled crystalline forms will depend on the specific application of that radio-labeled crystalline form. For example, for in vitro PD-L1 protein labeling and competition assays, crystalline forms that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

In some embodiments the radionuclide is selected from the group consisting of $^3$H, $^{14}$C, $^{125}$I, $^{35}$S and $^{82}$Br. Synthetic methods for incorporating radio-isotopes into organic compounds and crystalline forms are known in the art.

Specifically, a labeled crystalline form of the invention can be used in a screening assay to identify and/or evaluate compounds. For example, a newly synthesized or identified crystalline form (i.e., test crystalline form) which is labeled can be evaluated for its ability to bind a PD-L1 protein by monitoring its concentration variation when contacting with the PD-L1 protein, through tracking of the labeling. For example, a test crystalline form (labeled) can be evaluated for its ability to reduce binding of another compound which is known to bind to a PD-L1 protein (i.e., standard compound). Accordingly, the ability of a test crystalline form to compete with the standard compound for binding to the PD-L1 protein directly correlates to its binding affinity. Conversely, in some other screening assays, the standard crystalline form is labeled and test compounds are unlabeled. Accordingly, the concentration of the labeled standard compound is monitored in order to evaluate the competition between the standard compound and the test crystalline form, and the relative binding affinity of the test crystalline form is thus ascertained.

Kits

The present disclosure also includes pharmaceutical kits useful, e.g., in the treatment or prevention of diseases or disorders associated with the activity of PD-L1 including its interaction with other proteins such as PD-1 and B7-1 (CD80), such as cancer or infections, which include one or more containers containing a pharmaceutical composition comprising a therapeutically effective amount of a crystalline form of Compound 1, or any of the embodiments thereof. Such kits can further include one or more of various conventional pharmaceutical kit components, such as, e.g., containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The following abbreviations may be used herein: aq. (aqueous); br (broad); d (doublet); dd (doublet of doublets); DCM (dichloromethane); DMF (N, N-dimethylformamide); Et (ethyl); EtOAc (ethyl acetate); g (gram(s)); h (hour(s)); HPLC (high performance liquid chromatography); Hz (hertz); J (coupling constant); LCMS (liquid chromatography-mass spectrometry); m (multiplet); M (molar); MS (Mass spectrometry); Me (methyl); MeCN (acetonitrile);

MeOH (methanol); mg (milligram(s)); min. (minutes(s)); mL (milliliter(s)); mmol (millimole(s)); nM (nanomolar); NMR (nuclear magnetic resonance spectroscopy); Ph (phenyl); r.t. (room temperature), s (singlet); t (triplet or tertiary); TBS (tert-butyldimethylsilyl); tert (tertiary); tt (triplet of triplets); TFA (trifluoroacetic acid); THF (tetrahydrofuran); µg (microgram(s)); µL (microliter(s)); µM (micromolar); wt % (weight percent).

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The crystalline forms of the Examples have been found to inhibit the activity of PD-1/PD-L1 protein/protein interaction according to at least one assay described herein.

EMBODIMENTS

1. A crystalline form of Compound 1:

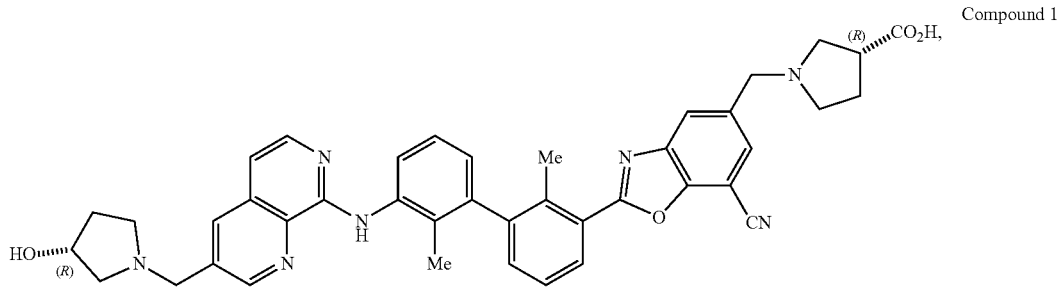

or a solvate thereof.

2. The crystalline form of embodiment 1, wherein the form is non-solvated.

3. The crystalline form of embodiment 2, which is Form I.

4. The crystalline form of embodiment 3, wherein the form has at least one XRPD peaks, in terms of 2-theta (±0.2 degrees), selected from 4.5, 7.9, 10.8, 13.1, 15.0, 17.3, 18.0, 20.8, 21.7, and 25.3 degrees.

5. The crystalline form of embodiment 3, wherein the form has at least two XRPD peaks, in terms of 2-theta (±0.2 degrees), selected from 4.5, 7.9, 10.8, 13.1, 15.0, 17.3, 18.0, 20.8, 21.7, and 25.3 degrees.

6. The crystalline form of embodiment 3, wherein the form has at least three XRPD peaks, in terms of 2-theta (±0.2 degrees), selected from 4.5, 7.9, 10.8, 13.1, 15.0, 17.3, 18.0, 20.8, 21.7, and 25.3 degrees.

7. The crystalline form of embodiment 3, wherein the form has at least four XRPD peaks, in terms of 2-theta (±0.2 degrees), selected from 4.5, 7.9, 10.8, 13.1, 15.0, 17.3, 18.0, 20.8, 21.7, and 25.3 degrees.

8. The crystalline form of embodiment 3, wherein the form has at least five XRPD peaks, in terms of 2-theta (±0.2 degrees), selected from 4.5, 7.9, 10.8, 13.1, 15.0, 17.3, 18.0, 20.8, 21.7, and 25.3 degrees.

9. The crystalline form of embodiment 3, wherein the form has characteristic XRPD peaks, in terms of 2-theta (±0.2 degrees), at 4.5, 7.9, 10.8, 13.1, 15.0, 17.3, 18.0, 20.8, 21.7, and 25.3 degrees.

10. The crystalline form of embodiment 3, wherein the form has at least one XRPD peaks, in terms of 2-theta (±0.2 degrees), selected from 4.5, 7.9, 10.8, 13.1, 15.0, 17.3, and 20.8 degrees.

11. The crystalline form of embodiment 3, wherein the form has at least two XRPD peaks, in terms of 2-theta (±0.2 degrees), selected from 4.5, 7.9, 10.8, 13.1, 15.0, 17.3, and 20.8 degrees.

12. The crystalline form of embodiment 3, wherein the form has at least three XRPD peaks, in terms of 2-theta (±0.2 degrees), selected from 4.5, 7.9, 10.8, 13.1, 15.0, 17.3, and 20.8 degrees.

13. The crystalline form of embodiment 3, wherein the form has at least four XRPD peaks, in terms of 2-theta (±0.2 degrees), selected from 4.5, 7.9, 10.8, 13.1, 15.0, 17.3, and 20.8 degrees.

14. The crystalline form of embodiment 3, wherein the form has at least five XRPD peaks, in terms of 2-theta (±0.2 degrees), selected from 4.5, 7.9, 10.8, 13.1, 15.0, 17.3, and 20.8 degrees.

15. The crystalline form of embodiment 3, wherein the form has characteristic XRPD peaks, in terms of 2-theta (±0.2 degrees), at 4.5, 7.9, 10.8, 13.1, 15.0, 17.3, and 20.8 degrees.

16. The crystalline form of any one of embodiments 3-15, wherein the form has an XRPD pattern as substantially shown in FIG. 1.

17. The crystalline form of any one of embodiments 3-16, having a first endothermic peak with an onset temperature (±3° C.) at 23° C. and a maximum at 98° C. and a second endothermic peak with an onset temperature (±3° C.) at 147° C. and a maximum at 159° C. in a DSC thermogram.

18. The crystalline form of any one of embodiments 3-17, wherein the form has a DSC thermogram substantially as shown in FIG. 2.

19. The crystalline form of any one of embodiments 3-18, wherein the form has a TGA thermogram substantially as shown in FIG. 3.

20. The crystalline form of embodiment 2, which is Form IV.

21. The crystalline form of embodiment 20, wherein the form has at least one XRPD peaks, in terms of 2-theta (±0.2 degrees), selected from 6.5, 7.4, 12.3, 14.8, 17.4, 18.9, 19.8, and 24.2 degrees.

22. The crystalline form of embodiment 20, wherein the form has at least two XRPD peaks, in terms of 2-theta (±0.2 degrees), selected from 6.5, 7.4, 12.3, 14.8, 17.4, 18.9, 19.8, and 24.2 degrees.

23. The crystalline form of embodiment 20, wherein the form has at least three XRPD peaks, in terms of 2-theta (±0.2 degrees), selected from 6.5, 7.4, 12.3, 14.8, 17.4, 18.9, 19.8, and 24.2 degrees.

24. The crystalline form of embodiment 20, wherein the form has at least four XRPD peaks, in terms of 2-theta (±0.2 degrees), selected from 6.5, 7.4, 12.3, 14.8, 17.4, 18.9, 19.8, and 24.2 degrees.

25. The crystalline form of embodiment 20, wherein the form has at least five XRPD peaks, in terms of 2-theta (±0.2 degrees), selected from 6.5, 7.4, 12.3, 14.8, 17.4, 18.9, 19.8, and 24.2 degrees.

26. The crystalline form of embodiment 20, wherein the form has characteristic XRPD peaks, in terms of 2-theta (±0.2 degrees), at 6.5, 7.4, 12.3, 14.8, 17.4, 18.9, 19.8, and 24.2 degrees.

27. The crystalline form of any one of embodiments 20-26, wherein the form has an XRPD pattern as substantially shown in FIG. 10.

28. The crystalline form of any one of embodiments 20-27, having a first endothermic peak with an onset temperature (±3° C.) at 31° C. and a maximum at 62° C. and a second endothermic peak with an onset temperature (±3° C.) at 135° C. and a maximum at 145° C. in a DSC thermogram.

29. The crystalline form of any one of embodiments 20-28, wherein the form has a DSC thermogram substantially as depicted in FIG. 11.

30. The crystalline form of any one of embodiments 20-29, wherein the form has a TGA thermogram substantially as depicted in FIG. 12.

31. The crystalline form of embodiment 1, wherein the form is a solvate.

32. The crystalline form of embodiment 31, wherein the form is a tetrahydrofuran solvate.

33. The crystalline form of embodiment 32, which is Form II.

34. The crystalline form of embodiment 33, wherein the form has at least one XRPD peak, in terms of 2-theta (±0.2 degrees), selected from 7.5, 9.9, 12.8, 13.4, 14.4, 15.0, 17.1, 19.8, and 23.3 degrees.

35. The crystalline form of embodiment 33, wherein the form has at least two XRPD peaks, in terms of 2-theta (±0.2 degrees), selected from 7.5, 9.9, 12.8, 13.4, 14.4, 15.0, 17.1, 19.8, and 23.3 degrees.

36. The crystalline form of embodiment 33, wherein the form has at least three XRPD peaks, in terms of 2-theta (±0.2 degrees), selected from 7.5, 9.9, 12.8, 13.4, 14.4, 15.0, 17.1, 19.8, and 23.3 degrees.

37. The crystalline form of embodiment 33, wherein the form has at least four XRPD peaks, in terms of 2-theta (±0.2 degrees), selected from 7.5, 9.9, 12.8, 13.4, 14.4, 15.0, 17.1, 19.8, and 23.3 degrees.

38. The crystalline form of embodiment 33, wherein the form has at least five XRPD peaks, in terms of 2-theta (±0.2 degrees), selected from 7.5, 9.9, 12.8, 13.4, 14.4, 15.0, 17.1, 19.8, and 23.3 degrees.

39. The crystalline form of embodiment 33, wherein the form has characteristic XRPD peaks, in terms of 2-theta (±0.2 degrees), at 7.5, 9.9, 12.8, 13.4, 14.4, 15.0, 17.1, 19.8, and 23.3 degrees.

40. The crystalline form of any one of embodiments 33-39, wherein the form has an XRPD pattern as substantially shown in FIG. 4.

41. The crystalline form of any one of embodiments 33-40, having a first endothermic peak with an onset temperature (±3° C.) at 68° C. and a maximum at 95° C. and a second endothermic peak with an onset temperature (±3° C.) at 153° C. and a maximum at 165° C. in a DSC thermogram.

42. The crystalline form of any one of embodiments 33-41, wherein the form has a DSC thermogram substantially as depicted in FIG. 5.

43. The crystalline form of any one of embodiments 33-42, wherein the form has a TGA thermogram substantially as depicted in FIG. 6.

44. The crystalline form of embodiment 32, which is Form III.

45. The crystalline form of embodiment 44, wherein the form has at least one XRPD peak, in terms of 2-theta (±0.2 degrees), selected from 5.9, 8.0, 12.6, 15.1, 17.0, 18.4, and 18.9 degrees.

46. The crystalline form of embodiment 44, wherein the form has at least two XRPD peaks, in terms of 2-theta (±0.2 degrees), selected from 5.9, 8.0, 12.6, 15.1, 17.0, 18.4, and 18.9 degrees.

47. The crystalline form of embodiment 44, wherein the form has at least three XRPD peaks, in terms of 2-theta (±0.2 degrees), selected from 5.9, 8.0, 12.6, 15.1, 17.0, 18.4, and 18.9 degrees.

48. The crystalline form of embodiment 44, wherein the form has at least four XRPD peaks, in terms of 2-theta (±0.2 degrees), selected from 5.9, 8.0, 12.6, 15.1, 17.0, 18.4, and 18.9 degrees.

49. The crystalline form of embodiment 44, wherein the form has at least five XRPD peaks, in terms of 2-theta (±0.2 degrees), selected from 5.9, 8.0, 12.6, 15.1, 17.0, 18.4, and 18.9 degrees.

50. The crystalline form of embodiment 44, wherein the form has characteristic XRPD peaks, in terms of 2-theta (±0.2 degrees), at 5.9, 8.0, 12.6, 15.1, 17.0, 18.4, and 18.9 degrees.

51. The crystalline form of any one of embodiments 44-50, wherein the form has an XRPD pattern as substantially shown in FIG. 7.

52. The crystalline form of any one of embodiments 44-51, having a first endothermic peak with an onset temperature (±3° C.) at 23° C. and a maximum at 56° C. and a second endothermic peak with an onset temperature (±3° C.) at 106° C. and a maximum at 122° C. in a DSC thermogram.

53. The crystalline form of any one of embodiments 44-52, wherein the form has a DSC thermogram substantially as depicted in FIG. 8.

54. The crystalline form of any one of embodiments 44-53, wherein the form has a TGA thermogram substantially as depicted in FIG. 9.

55. The crystalline form of embodiment 32, which is Form V.

56. The crystalline form of embodiment 55, wherein the form has at least one XRPD peak, in terms of 2-theta (±0.2 degrees), selected from 5.8, 8.0, 12.5, 15.1, 16.3, 17.0, 18.3, 18.9, 20.7, and 21.7 degrees.

57. The crystalline form of embodiment 55, wherein the form has at least two XRPD peaks, in terms of 2-theta (±0.2 degrees), selected from 5.8, 8.0, 12.5, 15.1, 16.3, 17.0, 18.3, 18.9, 20.7, and 21.7 degrees.

58. The crystalline form of embodiment 55, wherein the form has at least three XRPD peaks, in terms of 2-theta (±0.2 degrees), selected from 5.8, 8.0, 12.5, 15.1, 16.3, 17.0, 18.3, 18.9, 20.7, and 21.7 degrees.

59. The crystalline form of embodiment 55, wherein the form has at least four XRPD peaks, in terms of 2-theta (±0.2 degrees), selected from 5.8, 8.0, 12.5, 15.1, 16.3, 17.0, 18.3, 18.9, 20.7, and 21.7 degrees.

60. The crystalline form of embodiment 55, wherein the form has at least five XRPD peaks, in terms of 2-theta (±0.2 degrees), selected from 5.8, 8.0, 12.5, 15.1, 16.3, 17.0, 18.3, 18.9, 20.7, and 21.7 degrees.

61. The crystalline form of embodiment 55, wherein the form has characteristic XRPD peaks, in terms of 2-theta (±0.2 degrees), at 5.8, 8.0, 12.5, 15.1, 16.3, 17.0, 18.3, 18.9, 20.7, and 21.7 degrees.

62. The crystalline form of any one of embodiments 55-61, wherein the form has an XRPD pattern as substantially shown in FIG. 13.

63. The crystalline form of any one of embodiments 55-62, having a first endothermic peak with an onset temperature (±3° C.) at 23° C. and a maximum at 48° C. and a second endothermic peak with an onset temperature (±3° C.) at 113° C. and a maximum at 117° C. in a DSC thermogram.

64. The crystalline form of any one of embodiments 55-63, wherein the form has a DSC thermogram substantially as depicted in FIG. 14.

65. The crystalline form of any one of embodiments 55-64, wherein the form has a TGA thermogram substantially as depicted in FIG. 15.

66. A pharmaceutical composition comprising a crystalline form of any one of claims 1-65, and a pharmaceutically acceptable carrier or excipient.

67. A solid oral dosage form comprising the pharmaceutical composition of claim 66.

68. A process of preparing a crystalline form of Compound 1:

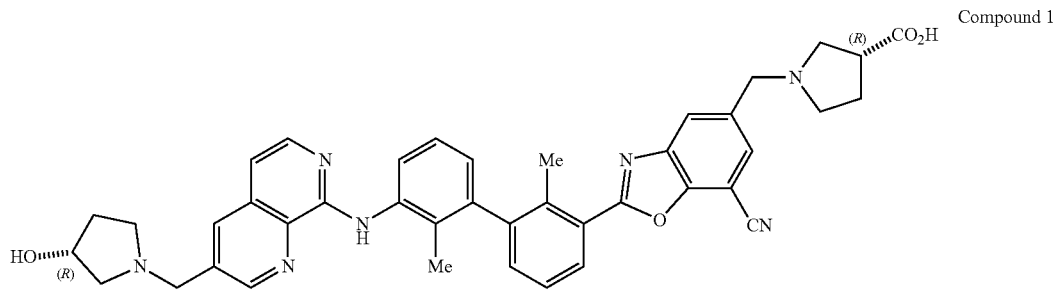

which is Form I, comprising converting a tetrahydrofuran solvate of Compound 1 to said Form I.

69. The process of embodiment 68, wherein the tetrahydrofuran solvate is Form II of Compound 1.

70. The process of embodiment 68 or 69, wherein the converting comprises slurrying the Form II in a solvent component to form the Form I.

71. The process of embodiment 70, wherein the slurrying comprises preparing a suspension comprising the Form II and a solvent component.

72. The process of embodiment 70, wherein the slurrying comprises preparing a suspension comprising the Form II and a solvent component; heating the suspension; and after said heating, cooling the suspension to form the Form I as a solid.

73. The process of embodiment 70, wherein the slurrying comprises preparing a suspension comprising the Form II and a solvent component; heating the suspension; and after said heating, cooling the suspension to form the Form I as a solid; wherein the solvent component comprises acetone and water.

74. The process of embodiment 70, wherein the slurrying comprises preparing a suspension comprising the Form II and a solvent component; heating the suspension to a temperature of about 35° C. to about 70° C.; and after said heating, cooling the suspension to a temperature of about 15° C. to about 25° C. to form the Form I as a solid; wherein the solvent component comprises acetone and water.

75. The process of embodiment 68, wherein the converting comprises drying the Form II to form the Form I.

76. A process of preparing a crystalline, tetrahydrofuran solvate of Compound 1:

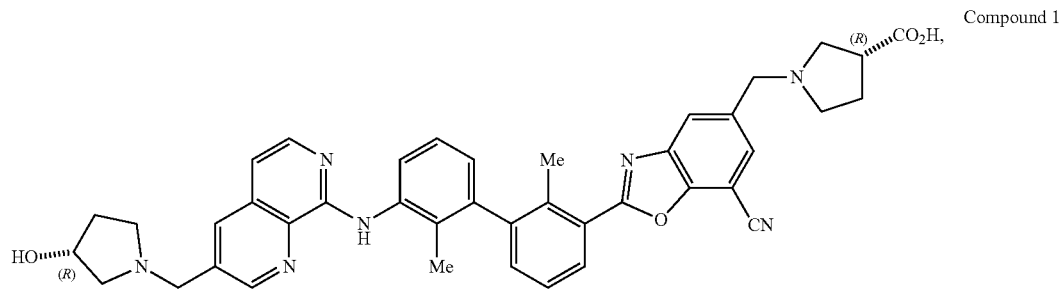

Compound 1 which is Form II,
comprising:
treating a solution comprising tetrahydrofuran and Compound 1 potassium salt:

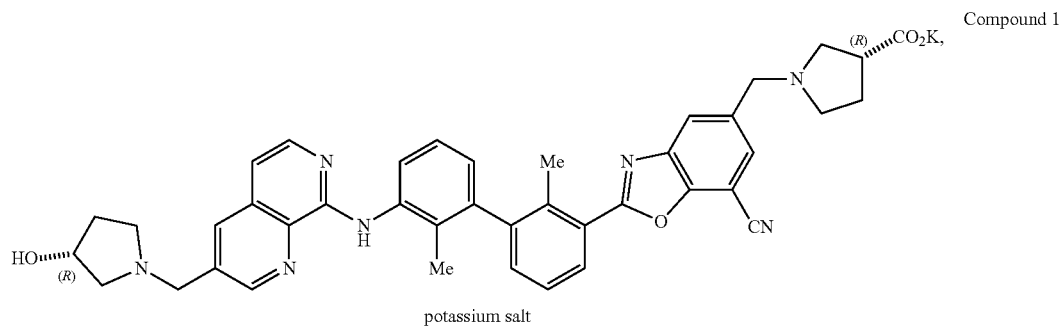

Compound 1 potassium salt with a metal scavenger or an ion exchange resin; and precipitating Form II of Compound 1.

77. The process of embodiment 76, wherein the treating comprises treating with the metal scavenger and the ion exchange resin.

78. The process of embodiment 76, wherein the solution further comprises a $C_{1-6}$ alcohol.

79. The process of embodiment 78, wherein the $C_{1-6}$ alcohol comprises methanol.

80. The process of embodiment 76, wherein the treating comprises heating the solution; and after said heating, cooling the solution.

81. The process of embodiment 76, wherein the treating comprises heating the solution; after said heating, cooling the solution; and after said cooling, filtering the solution and concentrating filtrate.

82. The process of embodiment 76, wherein the treating comprises heating the solution; after said heating, cooling the solution; after said cooling, filtering the solution and concentrating filtrate; and after concentrating said filtrate, adding seed crystals of Form I to said concentrated filtrate.

83. The process of embodiment 76, wherein the treating comprises heating the solution to a temperature of about 60° C. to about 70° C.; and after said heating, cooling the solution to a temperature of about 45° C. to about 55° C.; after said cooling, filtering the solution and concentrating filtrate; and after concentrating said filtrate, adding seed crystals of Form I to said concentrated filtrate to provide a suspension.

84. The process of embodiment 83, further comprising adding a solvent component to the suspension.

85. The process of embodiment 83, further comprising adding a solvent component to the suspension, wherein the solvent component is isopropyl acetate.

86. A process of preparing a crystalline, tetrahydrofuran solvate of Compound 1:

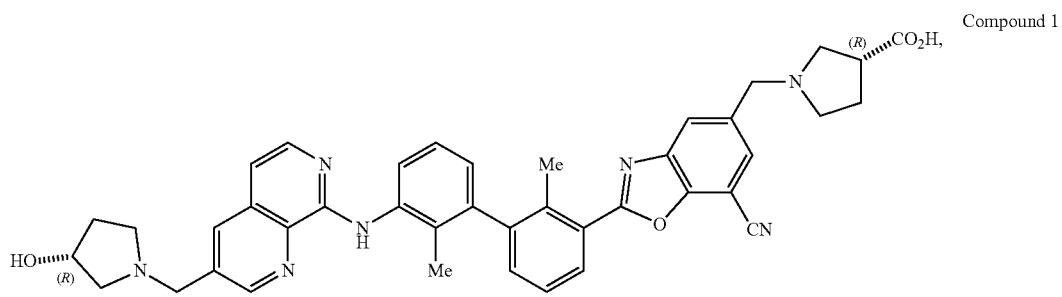

Compound 1 which is Form II, comprising converting Form III, Form IV, or Form V of the compound to Form II in the presence of a solvent component comprising tetrahydrofuran.

87. The process of embodiment 86, wherein the converting comprises preparing a suspension of Form III, Form IV, or Form V in the solvent component.

88. The process of embodiment 86, wherein the converting comprises preparing a suspension of Form III, Form IV, or Form V in the solvent component; heating the suspension to provide a solution; and cooling the solution.

89. The process of embodiment 86, wherein the converting comprises preparing a suspension of Form III, Form IV, or Form V in the solvent component; heating the suspension to provide a solution; after said heating, cooling the solution; and after said cooling, adding seed crystals of Form I to the solution.

90. The process of embodiment 86, wherein the converting comprises preparing a suspension of Form III, Form IV, or Form V in the solvent component; heating the suspension to provide a solution; after said heating, cooling the solution; after said cooling, adding seed crystals of Form I to the cooled solution to provide a seeded suspension; and adding an anti-solvent to the seeded suspension.

91. The process of embodiment 86, wherein the converting comprises preparing a suspension of Form III, Form IV, or Form V in the solvent component; heating the suspension to a temperature of about 35° C. to about 70° C. to provide a solution; after said heating, cooling the solution to about ambient temperature; after said cooling, adding seed crystals of Form I to the cooled solution to provide a seeded suspension; and adding an anti-solvent component to the seeded suspension.

92. The process of embodiment 90 or 91, wherein the anti-solvent component comprises isopropyl acetate.

93. The process of any one of embodiments 86-92, wherein the solvent component comprises tetrahydrofuran, $C_{1-6}$ alcohol, or a mixture thereof.

94. The process of any one of embodiments 86-92, wherein the solvent component comprises tetrahydrofuran or a mixture of tetrahydrofuran and methanol.

95. A process of preparing an amorphous form of Compound 1:

98. The process of embodiment 95, wherein the converting comprises preparing a suspension of the Form I of Compound 1 in a solvent component; heating the suspension to form a solution; after said heating, concentrating the solution; after said concentrating, adding the solution to a cold anti-solvent component to form a suspension of the amorphous form of Compound 1.

99. The process of embodiment 95, wherein the converting comprises preparing a suspension of the Form I of Compound 1 in a solvent component; heating the suspension to a temperature of about 40° C. to about 80° C. to form a solution; after said heating, concentrating the solution; after said concentrating, adding the solution to a cold anti-solvent component at a temperature of about −10° C. to about 15° C. to form a suspension of the amorphous form of Compound 1.

100. The process of any one of embodiments 96-99, wherein the solvent component comprises an aprotic solvent and a $C_{1-6}$ alcohol.

101. The process of any one of embodiments 96-99, wherein the solvent component comprises tetrahydrofuran and methanol.

102. The process of any one of embodiments 98-101, wherein the cold anti-solvent component comprises a polar aprotic solvent.

103. The process of any one of embodiments 98-101, wherein the cold anti-solvent component comprises isopropyl acetate.

104. A method of inhibiting PD-1/PD-L1 interaction, said method comprising administering to a patient a crystalline form of any one of embodiments 1-65.

105. A method of treating a disease or disorder associated with inhibition of PD-1/PD-L1 interaction, said method comprising administering to a patient in need thereof a therapeutically effective amount of a crystalline form of any one of embodiments 1-65.

106. A method of enhancing, stimulating and/or increasing the immune response in a patient, said method comprising administering to the patient in need thereof a therapeutically effective amount of a crystalline form of any one of embodiments 1-65.

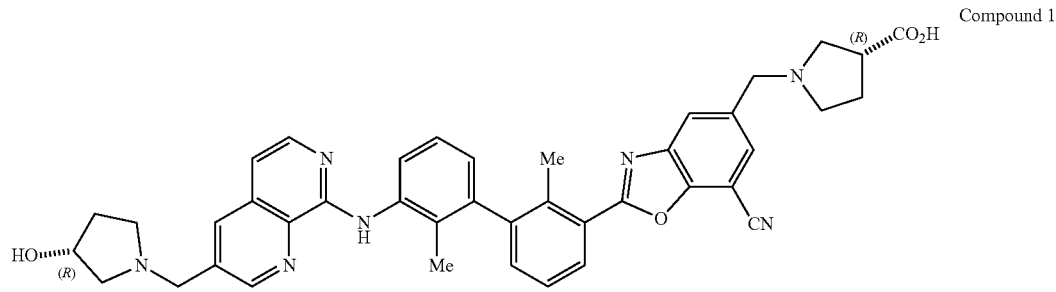

Compound 1 comprising converting Form I of Compound 1 to said amorphous form of Compound 1.

96. The process of embodiment 95, wherein the converting comprises preparing a suspension of the Form I of Compound 1 in a solvent component.

97. The process of embodiment 95, wherein the converting comprises preparing a suspension of the Form I of Compound 1 in a solvent component; heating the suspension to form a solution; after said heating, concentrating the heated solution.

EXAMPLES

Experimental Methods

The crystalline forms of Compound 1 drug substance have been characterized by the X-Ray Powder Diffraction (XRPD), Differential Scanning calorimetry (DSC), and Thermogravimetric Analysis (TGA). Information on instruments and conditions utilized for these studies is described below. The XRPD pattern and thermograms of DSC and TGA analysis for each of these five crystalline forms are also provided.

X-Ray Powder Diffraction (XRPD): Compound 1 crystalline forms were characterized by XRPD. The X-Ray Powder Diffraction (XRPD) was obtained from Bruker D8 Advance ECO X-ray Powder Diffractometer (XRPD) instrument. The general experimental procedures for XRPD were: (1) X-ray radiation from copper at 1.5418 Å and LYNXEYE™ detector; (2) X-ray power at 40 kV, 25 mA; and (3) the sample powder was dispersed on a zero-background sample holder. The general measurement conditions for XRPD were: Start Angle 3 degrees; Stop Angle 30 degrees; Sampling 0.015 degrees; and Scan speed 2 degree/min.

Differential Scanning calorimetry (DSC): Compound 1 crystalline forms were characterized by DSC. The DSC was obtained from TA Instruments Differential Scanning calorimetry, Discovery DSC2500 with auto sampler. The DSC instrument conditions were as follows: 20-300° C. at 10° C./min; Tzero aluminum sample pan and lid; and nitrogen gas flow at 50 mL/min.

Thermogravimetric Analysis (TGA): Compound 1 crystalline forms were also characterized by TGA. The TGA was obtained from TA Instruments Thermogravimetric Analyzer, Discovery TGA5500 with auto sampler. The general experimental conditions for TGA were: ramp from 25° C. to 300° C. at 10° C./min; nitrogen purge gas flow at 25 mL/min; platinum sample holder.

Example 1A. Preparation of Amorphous Compound 1

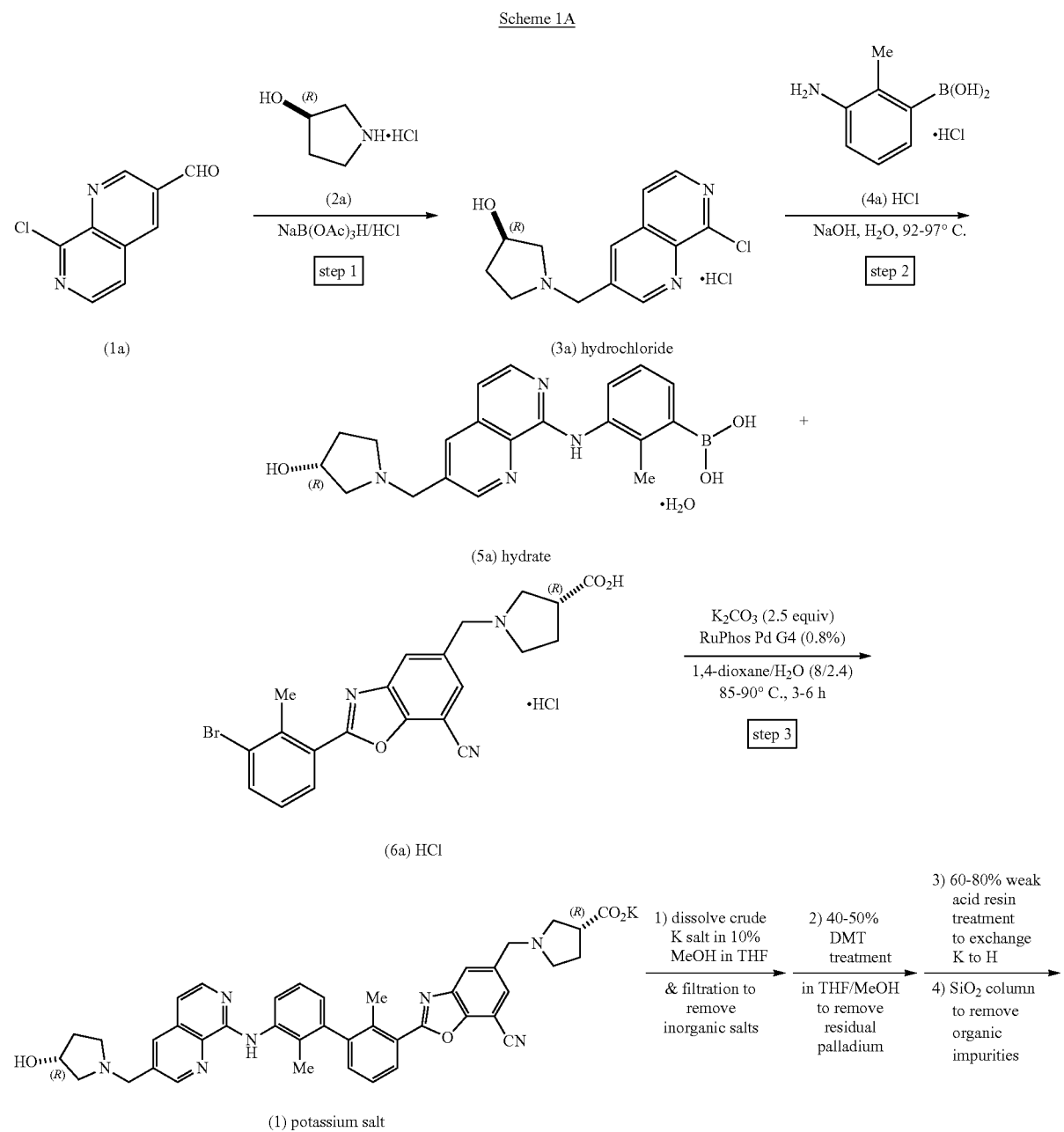

Scheme 1A

-continued

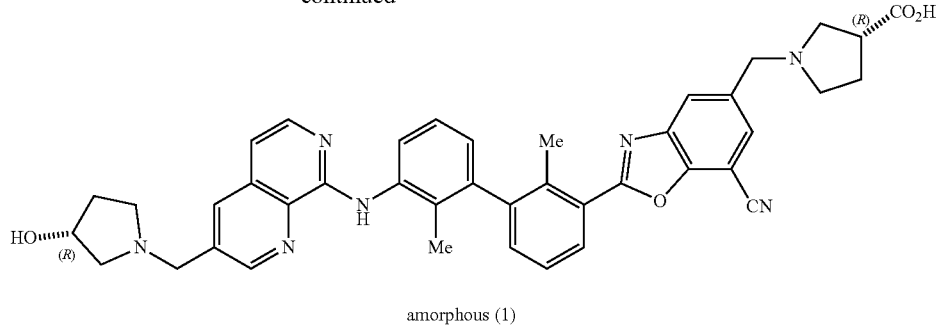

amorphous (1)

Step 1. (R)-1-((8-Chloro-1,7-naphthyridin-3-yl) methyl)pyrrolidin-3-ol Hydrochloride ((3a) Hydrochloride). Method A A suspension of (R)-pyrrolidin-3-ol hydrochloride ((2a) Hydrochloride, 7.7 g, 62.3 mmol, 1.2 equiv) in MeOH (35 mL) and DCM (35 mL) was agitated at ambient temperature. Sodium hydroxide (NaOH, 2.49 g, 62.3 mmol, 1.2 equiv) was added to the suspension at ambient temperature and the resulting mixture was agitated at ambient temperature for no less than (NLT) 1 hour before DCM (35 mL) was charged to the mixture. The mixture was continued to agitate at ambient temperature for 10 minutes. The solids (NaCl) were removed by filtration and the wet cake was washed with DCM (2×20 mL). The combined filtrates and wash solution was concentrated under the reduced pressure to remove most of the solvents. During concentration, DCM was charged to the concentrated residue for a total three times (3×50 mL) to remove most of the MeOH in the mixture. The concentrated residue, which contained MeOH in a range of 2.3-3.2% by weight, was then dissolved in DCM (100 mL) before 8-chloro-1,7-naphthyridine-3-carb aldehyde ((1a), 10.0 g, 51.9 mmol) was charged at ambient temperature. The resulting mixture was cooled to 10-20° C. and sodium triacetoxyborohydride (NaB(OAc)$_3$H, STAB, 12.97 g, 62.3 mmol, 1.2 equiv) was added to the cooled mixture portion wise at 10-20° C. The resulting reaction mixture was then agitated at 10-20° C. until the completion of the reductive amination reaction was confirmed by the HPLC analysis. An aqueous NaOH solution (2 N, 31.2 mL, 62.4 mmol, 1.2 equiv) was charged to the reaction mixture with agitation at 10-20° C. to quench the reductive amination reaction before an aqueous hydrochloric acid solution (4 N HCl, 40 mL, 160 mmol, 3.08 equiv) was charged at 10-20° C. to adjust pH to 3-4. The resulting mixture was stirred at 10-20° C. for NLT 30 minutes. Two phases were separated, and aqueous phase was extracted with DCM (2×50 mL). The organic phase, which contained the undesired process impurities, was discarded and the aqueous phase, which contained the desired product (3a) was kept for the subsequent process steps. The aqueous phase was added MeOH (10 mL) and DCM (90 mL) and the resulting mixture was then treated with an aqueous NaOH solution (2 N, 93.5 mL, 187 mmol, 3.6 equiv) at 10-25° C. to adjust the pH to 8.5-9.5. The resulting mixture was agitated at 10-25° C. for NLT 20 minutes before two phases were separated. The aqueous phase was extracted with a mixture of MeOH and DCM (1 to 9 by volume) twice (2×100 mL). The combined organic phase was then concentrated under the reduced pressure to remove the organic solvents. During concentration, additional amount of DCM (100 mL) was charged to the residue to remove most of methanol (MeOH). The residue was then dissolved in DCM (70 mL) and the methanol (MeOH) content in the solution was adjusted to 4-6%. If MeOH is below 4% by volume, charge more MeOH and if MeOH is over 6% by volume, continue the concentration under the reduced pressure with addition of DCM until the criterion set for the methanol content was met. A solution of 5-6 N HCl in IPA (9.44 mL, 1.0 equiv) was slowly charged to the solution at 15-30° C. and the resulting mixture was charged MTBE (150 mL) at 15-30° C. The resulting mixture was agitated at 15-30° C. for NLT 2 hours. The solids were collected by filtration, washed with MTBE (3×25 mL), and dried under vacuum at 40-45° C. to constant weight (weight loss≤1.0% within two hours) to afford the desired product, (R)-1-((8-chloro-1,7-naphthyridin-3-yl)methyl)pyrrolidin-3-ol hydrochloride ((3a) Hydrochloride, 13.7 g, 15.58 g theoretical, 87.9%; 99.5% pure by HPLC), as a white to off-white powder, which was used for the subsequent reaction without further purification. For (3a) Hydrochloride: $^1$H NMR (500 MHz, DMSO-d$_6$) δ 12.03 & 11.43 (s, 1H), 9.41 & 9.35 (s, 1H), 8.84 & 8.79 (s, 1H), 8.47 (d, J=5.5 Hz, 1H), 7.98 (m, 1H), 5.63 & 5.47 (s, 1H), 4.72 (m, 2H), 4.47 & 4.42 (s, 1H), 3.58, 3.36, 3.33 & 3.08 (m, 2H), 3.58, 3.47, 3.33 & 3.29 (m, 2H), and 2.32, 2.03, 1.96 & 1.87 (m, 2H); $^{13}$C NMR (125 MHz, DMSO-d$_6$) δ 155.2, 152.5, 143.3, 139.6, 138.7, 138.6, 132.7, 130.6 & 130.5, 121.9, 68.7, 61.1 & 60.4, 55.6 & 54.6, 52.4, and 33.7 & 33.0 ppm; $C_{13}H_{15}Cl_2N_3O$ (MW 300.18; $C_{13}H_{14}ClN_3O$ for (3a), MW 263.73), LCMS m/z 264.1 and 266.0 (M$^+$+H).

Step 2. (R)-(3-((3-((3-Hydroxypyrrolidin-1-yl) methyl)-1,7-naphthyridin-8-yl)amino)-2-methylphenyl)boronic Acid Hydrate ((5a) Hydrate)

To a 2000 mL four-neck round bottom flask equipped with a mechanic stirrer, a thermocouple, and a nitrogen inlet was charged ((R)-1-((8-chloro-1,7-naphthyridin-3-yl)methyl) pyrrolidin-3-ol hydrochloride ((3a) Hydrochloride, 100 g, 90% by weight, 300 mmol), 3-amino-2-methylphenylboronic acid hydrochloride ((4a) Hydrochloride, 57.7 g, 97.4% by weight, 300 mmol, 1.0 equiv), and water (200 mL). The mixture was then treated with a 1 N aqueous NaOH solution (300 mL, 300 mmol, 1.0 equiv) at ambient temperature before being heated to 92-97° C. The reaction mixture was then stirred at 92–97° C. for 4-6 hours until the nucleophilic substitution reaction completion was indicated by HPLC analysis. The reaction mixture was cooled to 35-45° C. before being polish filtered through a 3-5 cm thick of Celite pad. The Celite bed was washed with water (3×100 mL) and the combined filtrate and wash solution was charged THF (200 mL). The resulting mixture was then treated with 70% of a total 2 equivalents of 6 N aqueous NaOH solution (70 mL, 420 mmol, 1.4 equiv) at 35-45° C. until the clear solution becomes cloudy. The crystalline (5a) Hydrate seed (100 mg, 0.1 wt %) was then added to the cloudy mixture at 35-45° C. and solids was gradually formed within 20-40 minutes. The resulting suspension was stirred at 35-45° C. for NLT 1 hour before the remaining 30% of a total 2 equivalents of 6 N aqueous NaOH solution (30 mL, 180 mmol, 0.6 equiv) was added to the suspension at 35-45° C. The mixture was agitated at 35-45° C. for NLT 15 minutes before being cooled to ambient temperature. The pH value of the suspension was adjusted to 7.5-8.5 by addition of 1 N aqueous NaOH solution or 1 N aqueous HCl solution at ambient temperature. Water (200 mL) was charged into the suspension at ambient temperature and the mixture was agitated at ambient temperature for NLT 2 hours. The solids were collected by filtration, washed with a mixture of THF and water (10%, 3×300 mL) and MTBE (2×300 mL), and dried under vacuum at 40-45° C. to constant weight (weight loss≤1.0% within two hours) to afford the desired product, (R)-(3-((3-((3-hydroxypyrrolidin-1-yl)methyl)-1,7-naphthyridin-8-yl)amino)-2-methylphenyl)boronic acid hydrate ((5a) Hydrate, 118 g, 129.68 g theoretical, 91.0%; 99.6% pure by HPLC), as a white to off-white crystalline powder. For (5a) Hydrate: $^1$H NMR (500 MHz, DMSO-d$_6$) δ 9.20 (s, 1H), 8.88 (s, 1H), 8.31 (d, J=7.8 Hz, 1H), 8.18 (s, 1H), 8.12 (s, 2H), 8.01 (d, J=5.9 Hz, 1H), 7.20 (dd, J=7.7, 7.4 Hz, 1H), 7.15 (d, J=7.4 Hz, 1H), 7.13 (d, J=5.7 Hz, 1H), 4.77 (s, 1H), 4.25 (m, 1H), 3.86 (s, 2H), 2.79 & 2.54 (m, 2H), 2.71 & 2.54 (m, 2H), 2.44 (s, 3H), and 2.04 & 1.61 (M, 2 h); $^{13}$C NMR (125 MHz, DMSO-d$_6$) δ 153.3, 150.7, 142.5, 138.6, 138.2, 137.4, 134.5, 133.0, 131.7, 131.5, 127.9, 125.6, 122.4, 110.5, 62.9, 57.2, 52.8, 34.9, 17.8, and 6.98 ppm; $C_{20}H_{25}BN_4O_4$ (MW 396.25; $C_{20}H_{23}BN_4O_3$ for anhydrous (5a), MW 378.24), LCMS m/z 379.1 (M$^+$+H).

Step 3. (R)-1-((7-Cyano-2-(3'-((3-(((R)-3-hydroxy-pyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic Acid Potassium Salt ((1) Potassium Salt)

In a 3 L three-neck round bottom flask equipped with a reflux condenser, a mechanical stirrer, a thermal couple and a nitrogen inlet and nitrogen outlet was charged (R)-1-((2-(3-bromo-2-methylphenyl)-7-cyanobenzo[d]oxazol-5-yl)methyl)pyrrolidine-3-carboxylic acid hydrochloride ((6a) Hydrochloride, 136.5 g, 285 mmol, 1.014 equiv), (R)-3-((3-((3-hydroxypyrrolidin-1-yl)methyl)-1,7-naphthyridin-8-yl)amino)-2-methylphenyl)boronic acid ((5a) Hydrate, 87 wt %, 122.0 g, 281 mmol), potassium carbonate (K$_2$CO$_3$, 98 g, 712 mmol, 2.53 equiv), 1,4-dioxane (1200 mL), and water (360 mL) at room temperature. Nitrogen was bubbled through the mixture for 30 minutes at room temperature before the catalyst (RuPhos Pd G4, 1.939 g, 2.28 mmol, 0.008 equiv) was added to at room temperature under nitrogen atmosphere. The resulting reaction mixture was then heated to 88° C. and stirred at 87-89° C. for 4-6 hours. When HPLC analysis showed the coupling reaction was complete, the reaction mixture was cooled to 50° C. The bottom aqueous phase was separated and discarded. The top organic phase was added to a cold solution of acetonitrile (3400 mL) and water (200 mL) at 0-5° C. in 30 minutes. After stirred at 0-5° C. for 30 minutes, the solids were collected by filtration. The wet cake was washed with acetonitrile (1460 mL) and dried on the filter funnel for 16 hours at room temperature under house vacuum to provide the crude desired product, (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid potassium salt ((1) Potassium Salt, 237.1 g, 205.66 g theoretical, 115.2%), as a yellow to brown amorphous powder, which contained inorganic salts and water and was used for the subsequent step without further purification. For (1) Potassium Salt: $^1$H NMR (400 MHz, DMSO-d$_6$) δ 9.30 (s, 1H), 8.83 (d, J=2.0 Hz, 1H), 8.49 (dd, J=8.3, 1.3 Hz, 1H), 8.20-8.10 (m, 2H), 8.06 (s, 1H), 8.04 (d, J=5.7 Hz, 1H), 7.82 (d, J=1.4 Hz, 1H), 7.53 (t, J=7.7 Hz, 1H), 7.43 (dd, J=7.6, 1.5 Hz, 1H), 7.34 (t, J=7.9 Hz, 1H), 7.16 (d, J=5.8 Hz, 1H), 6.91 (dd, J=7.6, 1.3 Hz, 1H), 4.98 (br.s., 1H), 4.22 (dp, J=9.7, 3.5 Hz, 1H), 3.88-3.73 (m, 2H), 3.73-3.59 (m, 2H), 3.41 (br.s., 2H), 2.73 (dd, J=9.6, 6.1 Hz, 1H), 2.66 (t, J=7.9 Hz, 2H), 2.60-2.53 (m, 3H), 2.45 (s, 3H), 2.38 (dd, J=9.7, 3.5 Hz, 2H), 2.09 (s, 3H), 2.06-1.94 (m, 2H), 1.75 (ddt, J=12.3, 9.8, 7.2 Hz, 1H), and 1.58 (dddd, J=13.1, 8.1, 5.4, 3.3 Hz, 1H) ppm; $^{13}$C NMR (101 MHz, DMSO-d$_6$) δ 177.44, 164.30, 153.19, 150.70, 149.32, 143.95, 142.73, 142.37, 141.54, 138.98, 138.38, 137.68, 137.08, 134.26, 133.46, 132.94, 131.34, 129.85, 129.75, 126.73, 126.67, 126.38, 125.83, 125.55, 124.16, 120.97, 115.02, 111.04, 94.41, 69.85, 63.02, 59.25, 58.66, 57.35, 54.49, 52.88, 46.08, 34.95, 29.14, 18.60, and 14.91 ppm; $C_{41}H_{38}KN_7O_4$ (MW 731.90; $C_{41}H_{39}N_7O_4$ for free carboxylic acid, MW 693.79), LCMS (EI) m/z 694.6 (M$^+$+H).

Step (R)-1-((7-Cyano-2-(3'-((3-(((R)-3-hydroxypyr-rolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic Acid (Amorphous (1))

In a 5 L three-neck round bottom flask equipped with a reflux condenser, a mechanical stirrer, a thermal couple and a nitrogen inlet and nitrogen outlet was charged crude (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid potassium salt ((1) Potassium Salt, 254.0 g, 347 mmol), THF (2300 mL), and MeOH (254 mL) at room temperature. The resulting suspension was then charged Celite (50 g) before being stirred at room temperature for 2 hours. The mixture was filtered and the filter cake was washed with a mixture of THF (225 mL) and MeOH (25 mL). The filtrate was treated with SiliaMetS® DMT (125 g) and the resulting mixture was heated to 55-60° C. and stirred at 55-60° C. for 24 hours. After cooling to room temperature, the mixture was filtered and the filter cake was washed with a mixture of THF (450 mL) and MeOH (50 mL). Ion exchange resin (Dowex MAC-3 hydrogen form, 200 g) was then added to the filtrate and the resulting mixture was stirred at ambient temperature for 24 hours. The mixture was filtered and the filter cake was washed with a mixture of THF (225 mL) and MeOH (25 mL). Most of the solvents were removed by concentration under the reduced pressure and the residue was dissolved in THF (2000 mL) at room temperature to generate a solution. The solution was concentrated under the reduced pressure to about 700 grams and the resulting concentrated solution was then charged to methyl tert-butyl ether (MTBE, 5000 mL) at 0-5° C. to induce the precipitation of the crude desired product (1). After stirred at 0-5° C. for 1 hour, the solids were collected by filtration, washed with MTBE (1000 mL), and dried on the filter under house vacuum to afford the crude desired product (crude (1)). The crude product was purified by the silica gel (SiO$_2$) column chromatography eluting with 10-25% of MeOH in DCM to provide the desired product, (R)-1-((7-cyano-2-(3'-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid ((1), 202 g, 240.5 g theoretical, 84.0%; 96.6% pure by HPLC), as a light yellow amorphous powder. For Amorphous (1): $^1$H NMR (500 MHz, DMSO-d$_6$) δ 9.31 (s, 1H), 8.84 (d, J=2.0 Hz, 1H), 8.46 (dd, J=8.2, 1.0 Hz, 1H), 8.17 (d, J=2.0 Hz, 1H), 8.14 (dd, J=7.9, 1.3 Hz, 1H), 8.09 (d, J=1.4 Hz, 1H), 8.05 (d, J=5.8 Hz, 1H), 7.86 (d, J=1.3 Hz, 1H), 7.54 (dd, J=7.7, 7.7 Hz, 1H), 7.43 (dd, J=7.5, 1.3 Hz, 1H), 7.34 (dd, J=7.8, 7.9 Hz, 1H), 7.17 (d, J=5.8 Hz, 1H), 6.91 (dd, J=7.5, 1.1 Hz, 1H), 4.21 (m, 1H), 3.82 & 3.77 (d & d, J=13.9 & 13.8 Hz, 2H), 3.75 & 3.71 (d & d, J=13.5 & 13.5 Hz, 2H), 2.92 (m, 1H), 2.73 & 2.64 (m, 2H), 2.72 & 2.37 (m & dd, J=9.8, 3.7 Hz, 2H), 2.64 & 2.46 (m & m, 2H), 2.53 (m, 2H), 2.45 (s, 3H), 2.08 (s, 3H), 2.00 & 1.56 (m & m, 2H), and 1.96 (m, 2H) ppm; $^{13}$C NMR (125 MHz, DMSO-d$_6$) δ 175.9, 163.9, 152.8, 150.3, 149.0, 143.5, 142.3, 141.9, 141.1, 138.5, 137.2 (two carbons), 136.6, 133.8, 133.0, 132.5, 130.9, 129.4, 129.3, 126.3 (two carbons), 125.9, 125.3, 125.1, 123.8, 120.7, 114.5, 110.6, 94.1, 69.4, 62.5, 57.9, 56.8, 56.0, 53.1, 52.4, 41.7, 34.5, 27.2, 18.1, and 14.5 ppm; C$_{41}$H$_{39}$N$_7$O$_4$ (MW 693.79), LCMS m/z 694.2 (M$^+$+H); C$_{41}$H$_{39}$N$_7$O$_4$, cald C, 70.98, H, 5.67, and N, 14.13, found C, 70.59, H, 5.49, and N, 14.16.

Example 1B. Preparation of Crystalline Compound 1

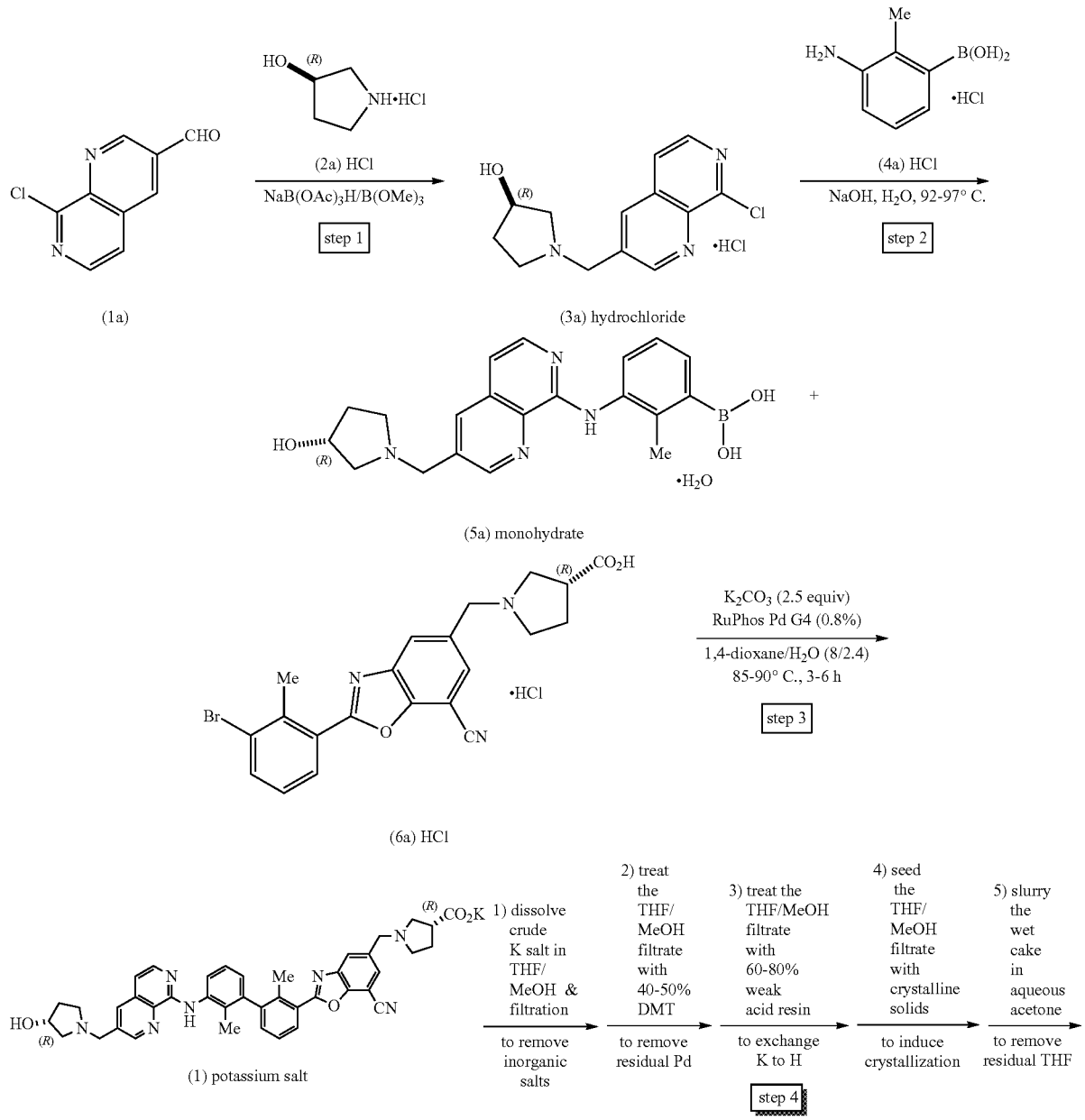

Scheme 1B

-continued

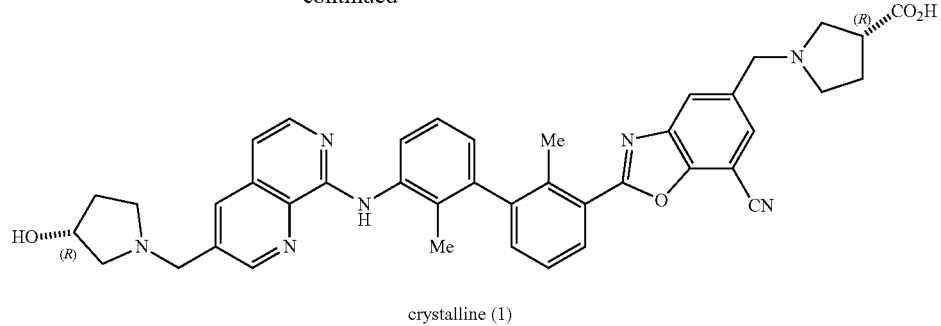

crystalline (1)

Step 1. (R)-1-((8-Chloro-1,7-naphthyridin-3-yl)methyl)pyrrolidin-3-ol Hydrochloride ((3a) Hydrochloride). Method B A suspension of 8-chloro-1,7-naphthyridine-3-carbaldehyde ((1a), 10.0 g, 98.2% pure, 51.9 mmol) and (R)-pyrrolidin-3-ol hydrochloride ((2a) Hydrochloride, 6.98 g, 99.36% pure, 56.1 mmol, 1.1 equiv) in a mixture of DCM (50 mL) and acetonitrile (10 mL) was treated with diisopropylethylamine (Hunig's base, DIEA, 56.1 mmol, 1.1 equiv) at ambient temperature. The resulting mixture was stirred at ambient temperature for 0.5-1 hour until it became a clear solution. Trimethyl borate (B(OMe)$_3$, 5.3 g, 51 mmol, 1.0 equiv) was added and the resulting solution (Solution A) was stirred at ambient temperature for 0.5-1 hour before being used for the subsequent reductive amination reaction. In another flask, sodium triacetoxyborohydride (NaB(OAc)$_3$H, STAB, 12.97 g, 61.2 mmol, 1.2 equiv) was suspended in DCM (50 mL) and the resulting suspension (Solution B) was cooled to 0-10° C. in an ice-bath. Solution A was then slowly added (dropwise) into Solution B while the internal temperature was kept at 0-10° C. After completion of adding Solution A, the additional funnel and flask were rinsed with DCM three times (3×20 mL) to make sure all Solution A was rinsed down to the reaction mixture. The ice-bath was removed, the reaction temperature was gradually warmed to 10-25° C., and the resulting reaction mixture was agitated at ambient temperature for 0.5 to 1 hour. When HPLC analysis showed the reductive amination reaction was complete, a 1 N aqueous NaOH solution (153 mmol, 153 mL, 3.0 equiv) was charged to quench the reaction at 10-25° C. followed by addition of MeOH (10 mL). Two phases were separated and the aqueous phase was extracted with a solution of 10% MeOH in DCM (3×50 mL). The combined organic extracts was then treated with the activated carbon (charcoal, 3 g) and Celite (3 g) and the resulting mixture was stirred at ambient temperature for NLT 2 hours. The mixture was filtered through a Celite pad (5 g) and the Celite bed was washed with a solution of 10% MeOH in DCM (3×30 mL). The combined filtrate and wash solution was concentrated under the reduced pressure to remove the organic solvents. The oily residue (crude (3a)) was dissolved in DCM (60 mL) to afford a solution. A solution of the first half of 5-6 N HCl in IPA (12.16/2 mL, 66.3/2 mmol, 1.3/2 equiv) was slowly charged to the solution of the crude (3a) in a mixture of MeOH and DCM at 15-30° C. with agitation. The solution became cloudy, solid formed, and the HCl vapor subsided. The resulting suspension was then charged MTBE (80 mL) to help induce the precipitation of (3a) Hydrochloride salt. The second half of a solution of 5-6 N HCl in IPA (12.16/2 mL, 66.3/2 mmol, 1.3/2 equiv) was then added to the suspension at ambient temperature with agitation before additional amount of MTBE (80 mL) was charged into the mixture. The resulting mixture was stirred at 15-30° C. for NLT 2 hours. The solids were collected by filtration, washed with MTBE (3×25 mL), and dried under vacuum at 40-45° C. to the constant weight (weight loss≤1.0% within two hours) to afford the desired product, (R)-1-((8-chloro-1,7-naphthyridin-3-yl)methyl)pyrrolidin-3-ol hydrochloride ((3a) Hydrochloride, 13.94 g, 15.31 g theoretical, 91%; 99.5% pure by HPLC), as a white to off-white crystalline powder, which is identical in every comparable aspect to the compound obtained by Method A and was used for the subsequent reaction without further purification.

Step 2. (R)-(3-((3-((3-Hydroxypyrrolidin-1-yl)methyl)-1,7-naphthyridin-8-yl)amino)-2-methylphenyl)boronic Acid Hydrate ((5a) Hydrate)

To a 2000 mL four-neck round bottom flask equipped with a mechanic stirrer, a thermocouple, and a nitrogen inlet was charged ((R)-1-((8-chloro-1,7-naphthyridin-3-yl)methyl)pyrrolidin-3-ol hydrochloride ((3a) Hydrochloride, 100 g, 90% by weight, 300 mmol), 3-amino-2-methylphenylboronic acid hydrochloride ((4a) Hydrochloride, 57.7 g, 97.4% by weight, 300 mmol, 1.0 equiv), and water (200 mL). The mixture was then treated with a 1 N aqueous NaOH solution (300 mL, 300 mmol, 1.0 equiv) at ambient temperature before being heated to 92-97° C. The reaction mixture was then stirred at 92-97° C. for 4-6 hours until the nucleophilic substitution reaction completion was indicated by HPLC analysis. The reaction mixture was cooled to 35-45° C. before being polish filtered through a 3-5 cm thick of Celite pad. The Celite bed was washed with water (3×100 mL) and the combined filtrate and wash solution was charged THF (200 mL). The resulting mixture was then treated with 70% of a total 2 equivalents of 6 N aqueous NaOH solution (70 mL, 420 mmol, 1.4 equiv) at 35-45° C. until the clear solution becomes cloudy. The crystalline (5a) Hydrate seed (100 mg, 0.1 wt %) was then added to the cloudy mixture at 35-45° C. and solids was gradually formed within 20-40 minutes. The resulting suspension was stirred at 35-45° C. for NLT 1 hour before the remaining 30% of a total 2 equivalents of 6 N aqueous NaOH solution (30 mL, 180 mmol, 0.6 equiv) was added to the suspension at 35-45° C. The mixture was agitated at 35-45° C. for NLT 15 minutes before being cooled to ambient temperature. The pH value of the suspension was adjusted to 7.5-8.5 by addition of 1 N aqueous NaOH solution or 1 N aqueous HCl solution at ambient temperature. Water (200 mL) was charged into the suspension at ambient temperature and the mixture was agitated at ambient temperature for NLT 2 hours. The solids were collected by filtration, washed with a mixture of THF and water (10%, 3×300 mL) and MTBE (2×300 mL), and dried under vacuum at 40-45° C. to constant weight (weight loss≤1.0% within two hours) to afford the desired product, (R)-(3-((3-((3-hydroxypyrrolidin-1-yl)methyl)-1,7-naph-thyridin-8-yl)amino)-2-methylphenyl)boronic acid hydrate ((5a) Hydrate, 118 g, 129.68 g theoretical, 91.0%; 99.6% pure by HPLC), as a white to off-white crystalline powder. For (5a) Hydrate: $^1$H NMR (500 MHz, DMSO-$d_6$) δ 9.20 (s, 1H), 8.88 (s, 1H), 8.31 (d, J=7.8 Hz, 1H), 8.18 (s, 1H), 8.12 (s, 2H), 8.01 (d, J=5.9 Hz, 1H), 7.20 (dd, J=7.7, 7.4 Hz, 1H), 7.15 (d, J=7.4 Hz, 1H), 7.13 (d, J=5.7 Hz, 1H), 4.77 (s, 1H), 4.25 (m, 1H), 3.86 (s, 2H), 2.79 & 2.54 (m, 2H), 2.71 & 2.54 (m, 2H), 2.44 (s, 3H), and 2.04 & 1.61 (M, 2 h); $^{13}$C NMR (125 MHz, DMSO-$d_6$) δ 153.3, 150.7, 142.5, 138.6, 138.2, 137.4, 134.5, 133.0, 131.7, 131.5, 127.9, 125.6, 122.4, 110.5, 62.9, 57.2, 52.8, 34.9, 17.8, and 6.98 ppm; $C_{20}H_{25}BN_4O_4$ (MW 396.25; $C_{20}H_{23}BN_4O_3$ for anhydrous (5a), MW 378.24), LCMS m/z 379.1 (M$^+$+H).

Step 3. (R)-1-((7-Cyano-2-(3'-((3-(((R)-3-hydroxy-pyrrolidin-1-yl)methyl)-1,7-naphthyridin-8-yl) amino)-2,2'-dimethyl-[1,1'-biphenyl]-3-yl)benzo[d] oxazol-5-yl)methyl)pyrrolidine-3-carboxylic Acid Potassium Salt (Compound 1 Potassium Salt)

In a 22 L three-neck round bottom flask equipped with a reflux condenser, a mechanical stirrer, a thermal couple and a nitrogen inlet and nitrogen outlet was charged (R)-1-((2-(3-bromo-2-methylphenyl)-7-cyanobenzo[d]oxazol-5-yl) methyl)pyrrolidine-3-carboxylic acid hydrochloride ((6a) Hydrochloride, 500.0 g, 1044 mmol, 1.000 equiv), (R)-(3-((3-((3-hydroxypyrrolidin-1-yl)methyl)-1,7-naphthyridin-8-yl)amino)-2-methylphenyl)boronic acid ((5a) Hydrate, calculated as 87 wt %, 447.0 g, 1028 mmol, 0.985 eq.), potassium carbonate ($K_2CO_3$, 361 g, 2609 mmol, 2.5 equiv), 1,4-dioxane (4500 mL), and water (1350 mL) at room temperature. Nitrogen was bubbled through the mixture for 30 minutes at room temperature before the catalyst (RuPhos Pd G4, 4.44 g, 5.22 mmol, 0.005 equiv) was added to at room temperature under nitrogen atmosphere. The resulting reaction mixture was then heated to 88° C. and stirred at 87-89° C. for 6 hours. When HPLC analysis showed the coupling reaction was complete, the reaction mixture was cooled to 50° C. The bottom aqueous phase was separated and discarded. The top organic phase was added to a cold solution of acetonitrile (12500 mL) and water (750 mL) at 0-5° C. in 30 minutes. After stirred at 0-5° C. for 30 minutes, the solids were collected by filtration. The wet cake was washed with acetonitrile (4000 mL) and put back into a reactor with acetonitrile (10000 mL) at room temperature. The mixture was heated to 55° C. and agitate at 55° C. for 1 hour before filtered at about 45° C. The cake was dried on the filter funnel for 16 hours, and was transferred to a vacuum oven at 55° C. under house vacuum with gentle nitrogen sweeping to provide the crude desired product, (R)-1-((7-cyano-2-(3'-((3-(((R)-3-hydroxypyrrolidin-1-yl) methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid potassium salt (Compound 1 Potassium Salt, 775 g, 764 g theoretical, 101.4%), as a yellow to brown amorphous powder, which contained inorganic salts and water and was used for the subsequent step without further purification. For Compound 1 Potassium Salt: $^1$H NMR (400 MHz, DMSO-$d_6$) δ 9.30 (s, 1H), 8.83 (d, J=2.0 Hz, 1H), 8.49 (dd, J=8.3, 1.3 Hz, 1H), 8.20-8.10 (m, 2H), 8.06 (s, 1H), 8.04 (d, J=5.7 Hz, 1H), 7.82 (d, J=1.4 Hz, 1H), 7.53 (t, J=7.7 Hz, 1H), 7.43 (dd, J=7.6, 1.5 Hz, 1H), 7.34 (t, J=7.9 Hz, 1H), 7.16 (d, J=5.8 Hz, 1H), 6.91 (dd, J=7.6, 1.3 Hz, 1H), 4.98 (br.s., 1H), 4.22 (dp, J=9.7, 3.5 Hz, 1H), 3.88-3.73 (m, 2H), 3.73-3.59 (m, 2H), 3.41 (br.s., 2H), 2.73 (dd, J=9.6, 6.1 Hz, 1H), 2.66 (t, J=7.9 Hz, 2H), 2.60-2.53 (m, 3H), 2.45 (s, 3H), 2.38 (dd, J=9.7, 3.5 Hz, 2H), 2.09 (s, 3H), 2.06-1.94 (m, 2H), 1.75 (ddt, J=12.3, 9.8, 7.2 Hz, 1H), and 1.58 (dddd, J=13.1, 8.1, 5.4, 3.3 Hz, 1H) ppm; $^{13}$C NMR (101 MHz, DMSO-$d_6$) δ 177.44, 164.30, 153.19, 150.70, 149.32, 143.95, 142.73, 142.37, 141.54, 138.98, 138.38, 137.68, 137.08, 134.26, 133.46, 132.94, 131.34, 129.85, 129.75, 126.73, 126.67, 126.38, 125.83, 125.55, 124.16, 120.97, 115.02, 111.04, 94.41, 69.85, 63.02, 59.25, 58.66, 57.35, 54.49, 52.88, 46.08, 34.95, 29.14, 18.60, and 14.91 ppm; $C_{41}H_{38}KN_7O_4$ (MW 731.90; $C_{41}H_{39}N_7O_4$ for free carboxylic acid, MW 693.79), LCMS (EI) m/z 694.6 (M$^+$+H).

Step 4. (R)-1-((7-Cyano-2-(3'-((3-(((R)-3-hydroxy-pyrrolidin-1-yl)methyl)-1,7-naphthyridin-8-yl) amino)-2,2'-dimethyl-[1,1'-biphenyl]-3-yl)benzo[d] oxazol-5-yl)methyl)pyrrolidine-3-carboxylic Acid (the Crystalline THF solvate Form (Form II) and the non-Solvate non-Hydrate Crystalline Form (Form I) of Compound 1)

In a 5 L three-neck round bottom flask equipped with a reflux condenser, a mechanical stirrer, a thermal couple and a nitrogen inlet and nitrogen outlet was charged crude (R)-1-((7-cyano-2-(3'-((3-(((R)-3-hydroxypyrrolidin-1-yl) methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid potassium salt (Compound 1 Potassium Salt, 160.0 g, 219 mmol), THF (1440 mL), and MeOH (160 mL) at room temperature. To the resulting suspension was then charged Celite (64 g) before being stirred at room temperature for 2 hours. The mixture was filtered and the filter cake was washed with a mixture of THF (288 mL) and MeOH (32 mL). To the combined filtrate was charged SiliaMetS® DMT (72 g) and ion exchange resin (Dowex MAC-3 hydrogen form, 120 g). The resulting mixture was heated to 58-63° C. and stirred at 58-63° C. for 24 hours. The mixture was filtered at about 50° C. and the filter cake was washed with a mixture of THF (576 mL) and MeOH (64 mL). The combined filtrate was polish filtered and rinsed with a mixture of THF (144 mL) and MeOH (16 mL). The combined solution was distilled under reduced pressure to about 1280 grams. The crystalline Compound 1 seeds (Form I, 0.30 g) were charged to the concentrated solution at 15-25° C. to induce crystallization. After agitated at 15-25° C. for 1 hour, the suspension was treated with isopropyl acetate (IPAc, 2560 mL) at 15-25° C. in 30 minutes. The resulting suspension was agitated at 15-25° C. for 1 hour before the solids were collected by filtration. The wet cake of the desired product, Compound 1, was confirmed to be a crystalline THF solvate by the X-ray powder diffraction (XRPD) analysis and this crystalline THF solvate has been designated as the Form II of Compound 1 drug substance. Form II of the crystalline Compound 1 drug substance is a stable THF solvate obtained from crystallization in the THF-containing solvent systems. On DSC, Form II first under goes de-solvation followed by possible melting at around 154-165° C. Further, DSC analysis of Compound 1 crystalline Form II revealed one endothermic peak with an onset temperature of 68.2° C. and a maximum at 95.5° C. and a second endothermic peak with an onset temperature of 153.5° C. and a maximum at 165.1° C. The DSC thermogram of Compound 1 crystalline Form II is provided in FIG. 5. On TGA, 7.6% weight loss at below 100° C. and 1.4% weight loss at around 100-170° C. are observed. Form II decomposes above 170° C. Further, TGA analysis of Compound 1 crystalline Form II revealed 7.6% weight loss below 100° C. due to loss of solvents and water and 1.4% weight loss between 100° C. and 170° C. due to potential loss of THF. It decomposes above 170° C. The TGA thermogram of Compound 1 crystalline Form II is provided in FIG. 6. Form II is readily converted to the thermodynamically most stable non-solvate non-hydrate crystalline form, Form I, by removal of THF through drying or slurry in solvent(s). Form I and Form II of Compound 1 drug substance have distinctive XRPD patterns. Specifically Form II solid was confirmed as a crystalline solid according to XRPD analysis. The XRPD pattern of Compound 1 crystalline Form II is shown in FIG. 4 and the peak data of Compound 1 crystalline Form II is provided in Table 2.

TABLE 2

XRPD Peak Data for Compound 1 Crystalline Form II

| 2-Theta (°) | Relative Intensity (%) |
|---|---|
| 5.8 | 0.7 |
| 6.1 | 0.6 |
| 7.5 | 80.9 |
| 9.7 | 6.6 |
| 9.9 | 25.6 |
| 10.7 | 5.1 |
| 11.3 | 6.9 |
| 11.6 | 6.9 |
| 12.8 | 32.0 |
| 12.9 | 28.4 |
| 13.4 | 25.8 |
| 14.4 | 62.9 |
| 14.8 | 28.3 |
| 15.0 | 100 |
| 15.3 | 6.7 |
| 15.8 | 18.0 |
| 16.1 | 20.0 |
| 16.7 | 25.2 |
| 17.1 | 38.7 |
| 18.0 | 14.7 |
| 18.2 | 35.4 |
| 18.9 | 30.4 |
| 19.6 | 19.0 |
| 19.8 | 77.5 |
| 20.0 | 34.0 |
| 20.5 | 16.0 |
| 20.6 | 16.8 |
| 20.8 | 28.3 |
| 21.2 | 11.0 |
| 21.7 | 5.0 |
| 22.2 | 5.3 |
| 22.3 | 5.8 |
| 22.7 | 9.1 |
| 22.9 | 37.0 |
| 23.3 | 61.4 |
| 23.6 | 18.0 |
| 24.1 | 7.9 |
| 24.6 | 1.7 |
| 24.8 | 0.5 |
| 25.3 | 6.8 |
| 25.7 | 9.2 |
| 26.0 | 9.7 |
| 26.2 | 26.1 |
| 26.6 | 2.8 |
| 27.1 | 8.1 |
| 27.5 | 11.0 |
| 28.4 | 3.2 |
| 28.7 | 2.8 |
| 29.0 | 3.6 |
| 29.4 | 17.1 |
| 29.7 | 6.1 |

The wet cake of the Form II crystals obtained was then washed with a mixture of THF (144 mL), MeOH (16 mL), and IPAc (320 mL) and dried on the filter under house vacuum at ambient temperature for 12 hours to provide the desired product, (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid (Compound 1, 137.8 g, 152 g theoretical, 91% yield; 94.9 wt % by HPLC, 86.4% yield after correction), as an off-white to light yellow crystalline solid, which contained approximately 2-3% of THF and 2-3% of water. This crystalline solid was confirmed to be a mixture of two crystalline forms, the non-solvate and non-hydrate crystalline form which has been designated as Form I and the stable THF solvate crystalline form which has been designated as Form II, with majority as Form I and minority as Form II based on XRPD analysis.

The crystalline solid, which contains about 2-3% of THF, was further dried in the vacuum oven at 55° C. under house vacuum with a gentle nitrogen sweeping for 2-3 hours to reduce the residual THF to less than 1.0%. The resulting crystalline solid (100 g, 97 wt % by HPLC, THF<1.0%) was then suspended in acetone (1960 mL) and water (40 mL) at room temperature. The resulting slurry was heated to 45-55° C. and agitated at 45-55° C. for 2-3 hours. After cooling to 15-25° C., the solid was collected by filtration, washed with acetone (100 mL), and dried in a vacuum oven at 45° C. under house vacuum with a gentle nitrogen sweeping for 8-12 hours to provide the dried desired product, (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid (Compound 1, 98.4 g, 98.4% yield), as an off-white to light yellow crystalline powder, which contained less than 200 ppm of THF and was confirmed to be the non-solvate and non-hydrate crystalline form (Form I) by XRPD analysis. For Crystalline Compound 1: $^1$H NMR (500 MHz, DMSO-$d_6$) δ 9.31 (s, 1H), 8.84 (d, J=2.0 Hz, 1H), 8.46 (dd, J=8.2, 1.0 Hz, 1H), 8.17 (d, J=2.0 Hz, 1H), 8.14 (dd, J=7.9, 1.3 Hz, 1H), 8.09 (d, J=1.4 Hz, 1H), 8.05 (d, J=5.8 Hz, 1H), 7.86 (d, J=1.3 Hz, 1H), 7.54 (dd, J=7.7, 7.7 Hz, 1H), 7.43 (dd, J=7.5, 1.3 Hz, 1H), 7.34 (dd, J=7.8, 7.9 Hz, 1H), 7.17 (d, J=5.8 Hz, 1H), 6.91 (dd, J=7.5, 1.1 Hz, 1H), 4.21 (m, 1H), 3.82 & 3.77 (d & d, J=13.9 & 13.8 Hz, 2H), 3.75 & 3.71 (d & d, J=13.5 & 13.5 Hz, 2H), 2.92 (m, 1H), 2.73 & 2.64 (m, 2H), 2.72 & 2.37 (m & dd, J=9.8, 3.7 Hz, 2H), 2.64 & 2.46 (m & m, 2H), 2.53 (m, 2H), 2.45 (s, 3H), 2.08 (s, 3H), 2.00 & 1.56 (m & m, 2H), and 1.96 (m, 2H) ppm; $^{13}$C NMR (125 MHz, DMSO-$d_6$) δ 175.9, 163.9, 152.8, 150.3, 149.0, 143.5, 142.3, 141.9, 141.1, 138.5, 137.2 (two carbons), 136.6, 133.8, 133.0, 132.5, 130.9, 129.4, 129.3, 126.3 (two carbons), 125.9, 125.3, 125.1, 123.8, 120.7, 114.5, 110.6, 94.1, 69.4, 62.5, 57.9, 56.8, 56.0, 53.1, 52.4, 41.7, 34.5, 27.2, 18.1, and 14.5 ppm; $C_{41}H_{39}N_7O_4$ (MW 693.79), LCMS m/z 694.2 (M$^+$+H).

Form I solid was confirmed as a crystalline solid according to XRPD analysis. The XRPD pattern of Compound 1 crystalline Form I is shown in FIG. 1 and the peak data of Compound 1 crystalline Form I is provided in Table 1.

TABLE 1

XRPD Peak Data for Compound 1 Crystalline Form I

| 2-Theta (°) | Relative Intensity (%) |
|---|---|
| 4.5 | 10.1 |
| 7.1 | 0.6 |
| 7.9 | 19.8 |

TABLE 1-continued

XRPD Peak Data for Compound 1 Crystalline Form I

| 2-Theta (°) | Relative Intensity (%) |
| --- | --- |
| 9.0 | 6.5 |
| 9.3 | 2.5 |
| 9.7 | 1.4 |
| 10.0 | 0.8 |
| 10.8 | 11.1 |
| 11.1 | 0.8 |
| 12.0 | 0.8 |
| 13.1 | 100 |
| 13.5 | 15.6 |
| 13.8 | 26.2 |
| 14.4 | 4.9 |
| 14.7 | 23.1 |
| 15.0 | 40.4 |
| 15.3 | 1.2 |
| 15.8 | 24.5 |
| 16.1 | 15.4 |
| 16.5 | 15.4 |
| 17.3 | 51.4 |
| 18.0 | 37.2 |
| 18.5 | 28.3 |
| 19.1 | 5.0 |
| 19.5 | 2.5 |
| 19.7 | 1.7 |
| 20.3 | 9.3 |
| 20.8 | 95.9 |
| 21.1 | 6.0 |
| 21.4 | 12.9 |
| 21.7 | 51.6 |
| 22.3 | 19.8 |
| 22.6 | 4.4 |
| 23.2 | 8.0 |
| 23.5 | 18.1 |
| 23.8 | 12.9 |
| 24.0 | 7.0 |
| 24.5 | 5.6 |
| 24.9 | 1.9 |
| 25.3 | 42.0 |
| 25.6 | 5.6 |
| 25.9 | 1.6 |
| 26.1 | 4.3 |
| 26.4 | 12.7 |
| 26.8 | 5.9 |
| 27.2 | 4.1 |
| 27.4 | 6.6 |
| 27.8 | 7.3 |
| 28.4 | 12.0 |
| 29.2 | 12.1 |
| 29.6 | 1.7 |

Form I is a non-solvate and non-hydrate crystalline form. On DSC, it first undergoes dehydration at below 125° C. followed by melting at around 148-160° C. Specifically DSC analysis of Compound 1 crystalline Form I revealed one endothermic peak with an onset temperature of 23.1° C. and a maximum at 98.3° C. and a second endothermic peak with an onset temperature of 147.6° C. and a maximum at 159.6° C. due to melting. The DSC thermogram of Compound 1 crystalline Form I is provided in FIG. 2. On TGA, approximately 2.4% weight loss is observed at below 120° C., which is mainly due to dehydration. The compound decomposes above 160° C. after melting. Like the amorphous powder of Compound 1 drug substance, this non-solvate and non-hydrate crystalline form (Form I) is hygroscopic. Further, TGA analysis of Compound 1 crystalline Form I revealed 2.4% weight loss below 125° C. mainly due to loss of water. It decomposes above 160° C. after melting. The TGA thermogram of Compound 1 crystalline Form I is provided in FIG. 3. During water dynamic vapor sorption (DVS) analysis of this non-solvate and non-hydrate crystalline form (Form I), approximately 6.5% of water was absorbed at 80% RH and 25° C. for this crystalline form and the sample was pre-dried at 50° C. under dried nitrogen ($N_2$) for 1 hour before the DVS analysis. For comparison, approximately 12% of water was absorbed at 80% RH and 25° C. for the amorphous powder. No crystalline form change was observed in the solid state after the DVS analysis. The crystalline Form I showed no change in solid state form and no corresponding hydrate was formed after stirring in water at ambient temperature for overnight, humidifying under 95% RH/25° C. for three days, cycling from 5% RH to 95% RH and back to 5% RH at 25° C. and 5% RH interval, or drying under dry nitrogen gas ($N_2$) at 25° C. for one day. These experimental data have confirmed that Form I is the thermodynamically most stable crystalline form under the current investigated process conditions.

In addition to the non-solvate and non-hydrate crystalline form (Form I) and the stable crystalline THF solvate form (Form II), several other meta-stable crystalline forms of Compound 1 drug substance have also been identified and characterized during process development. These crystalline forms include the meta-stable crystalline THF-solvate forms (Form III and Form V) and the meta-stable non-solvate crystalline form (Form IV). Five crystalline forms have distinctive XRPD patterns and can be readily differentiated by the XRPD analysis.

Example 2. Preparation of the Meta-Stable Compound 1 Crystalline THF Solvate Form (Form III) from the Amorphous Compound 1 Potassium Salt In a 22 L three-neck round bottom flask equipped with a reflux condenser, a mechanical stirrer, a thermal couple and a nitrogen inlet and nitrogen outlet was charged crude amorphous (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl) pyrrolidine-3-carboxylic acid potassium salt (amorphous Compound 1 Potassium Salt, 805 g, 1100 mmol), THF (8000 mL), and MeOH (800 mL) at ambient temperature. The resulting suspension was then charged Celite (160 g) before being stirred at room temperature for 2 hours. The mixture was filtered and the filter cake was washed with a mixture of THF (720 mL) and MeOH (80 mL). The Celite bed was discarded and the combined filtrate was treated with SiliaMetS® DMT (360 g) and the ion exchange resin (Dowex MAC-3 hydrogen form, 525 g) at ambient temperature. The resulting mixture was heated to 50-55° C. and stirred at 50-55° C. for 24 hours. The mixture was cooled to room temperature and filtered at about 20° C. The filter cake was washed with a mixture of THF (2160 mL) and MeOH (240 mL). The combined filtrate was concentrated under reduced pressure. Part of the concentrated residue (about 10 wt % of the total mass and approximately 76 g of Compound 1) was stored at −20° C. for 3 days. Solids were found to be gradually formed during the cold storage. The isolated solids (approximately 10 g) were dissolved in THF (30 mL) at room temperature. The clear solution became cloudy after 10 minutes at approximately 20° C. After agitation at room temperature for 30 minutes, the resulting solids were collected by filtration to provide (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid (Compound 1, 1.8 g, 18% yield) as an off-white to yellow cotton-like crystalline powder, which contained about 5.9 wt % of THF and was confirmed to be another crystalline THF solvate by XRPD analysis. This crystalline THF solvate form was designated as Form III and the solids collected were used as seeds for the large-scale operations. Form III solid was confirmed as a crystalline solid according to XRPD analysis. The XRPD pattern of Compound 1 crystalline Form III is shown in FIG. 7 and the peak data of Compound 1 crystalline Form III is provided in Table 3.

TABLE 3

XRPD Peak Data for Compound 1 Crystalline Form III

| 2-Theta (°) | Relative Intensity (%) |
| --- | --- |
| 5.9 | 100 |
| 6.4 | 1.2 |
| 6.8 | 7.1 |
| 7.4 | 3.8 |
| 8.0 | 12.8 |
| 11.1 | 8.9 |
| 11.2 | 10.7 |
| 11.4 | 4.2 |
| 11.7 | 3.6 |
| 12.4 | 5.7 |
| 12.6 | 14.0 |
| 12.9 | 1.4 |
| 13.7 | 4.0 |
| 14.4 | 0.3 |
| 14.9 | 12.1 |
| 15.1 | 29.1 |
| 15.3 | 9.8 |
| 15.6 | 3.6 |
| 16.1 | 4.9 |
| 16.4 | 23.5 |
| 16.7 | 11.3 |
| 17.0 | 43.7 |
| 17.4 | 10.2 |
| 17.6 | 9.1 |
| 18.0 | 9.6 |
| 18.4 | 32.1 |
| 18.9 | 60.4 |
| 19.4 | 10.0 |
| 19.8 | 10.1 |
| 20.1 | 8.9 |
| 20.7 | 11.2 |
| 21.2 | 4.1 |
| 21.7 | 18.0 |
| 22.2 | 4.1 |
| 22.6 | 3.9 |
| 22.9 | 10.3 |
| 23.1 | 6.9 |
| 23.8 | 0.5 |
| 24.2 | 12.2 |
| 24.8 | 4.8 |
| 25.0 | 4.4 |
| 25.6 | 7.7 |
| 26.1 | 2.3 |
| 26.3 | 1.9 |
| 26.9 | 1.3 |
| 27.2 | 2.0 |
| 27.8 | 0.9 |
| 28.5 | 6.1 |
| 28.9 | 2.3 |

Multiple endothermal events were observed on DSC for this crystalline THF solvate form (Form III) at below 150° C. and approximately 9.7% weight loss was observed on TGA at below 150° C. These events are most probably resulted from dehydration and de-solvation. Further, DSC analysis of Compound 1 crystalline Form III revealed one endothermic peak with an onset temperature of 23.3° C. and a maximum at 56.2° C. and a second endothermic peak with an onset temperature of 106.7° C. and a maximum at 122.4° C. The DSC thermogram of Compound 1 crystalline Form III is provided in FIG. 8. TGA analysis of Compound 1 crystalline Form III revealed 9.7% weight loss below 150° C. due to loss of solvents and water. It decomposes above 160° C. The TGA thermogram of Compound 1 crystalline Form III is provided in FIG. 9.

Example 3. Preparation of the Meta-Stable Compound 1 Crystalline THF Solvate Form (Form III) from Amorphous Compound 1

A suspension of amorphous Compound 1 drug substance (250 g) in THF (1500 mL) and MeOH (200 mL) was heated to 60° C. for 30 minutes, and the resulting solution was then gradually cooled to about 30° C. The Form III seeds (0.5 g) were then added into the solution at 30° C. to induce the crystallization. The resulting suspension was further cooled to ambient temperature and agitated at ambient temperature for 1-2 hours. Solids were gradually generated and precipitated out from the solution during agitation at ambient temperature. The solids were collected by filtration to provide (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid (Compound 1, 155 g, 62% yield) THF 5.9 wt %) as an off-white to yellow cotton-like crystalline powder, which contained about 5.9 wt % of THF and was confirmed to be Form III of the crystalline THF solvate by XRPD analysis. The same crystalline THF solvate form (Form III) could also be obtained from amorphous Compound 1 drug substance by crystallization and precipitation from approximately three volumes of THF solution or from slurry in approximately ten volumes of THF at ambient temperature.

Example 4. Preparation of the Non-Solvate Compound 1 Crystalline Form (Form IV) by Drying the Compound 1 Crystalline THF Solvate (Form III)

After drying the meta-stable crystalline THF solvate form (Form III) on the filter for 22 hours, the THF content was reduced from 5.9 wt % to approximately 0.5 wt % and the crystalline form was found to be changed. The dried solid was confirmed to be a meta-stable non-solvate crystalline form, which has been designated as Form IV.

Like the amorphous powder of Compound 1 drug substance, this meta-stable non-solvate crystalline form (Form IV) is hygroscopic. During water dynamic vapor sorption (DVS) analysis of this non-solvate crystalline form (Form IV), approximately 8.2% of water was absorbed at 80% RH and 25° C. for this crystalline form and the sample was pre-dried at 25° C. under dried nitrogen ($N_2$) for 1 hour before the DVS analysis. No crystalline form change was observed in the solid state after the DVS analysis. Further drying of this non-solvate crystalline form (Form IV) on the filter at ambient temperature for an extended period of time (3-6 days), the residual THF content was further reduced to approximately 0.1 wt %, but the crystalline form (Form IV) remained unchanged.

Form IV solid was confirmed as a crystalline solid according to XRPD analysis. The XRPD pattern of Compound 1 crystalline Form IV is shown in FIG. 10 and the peak data of Compound 1 crystalline Form IV is provided in Table 4.

TABLE 4

XRPD Peak Data for Compound 1 Crystalline Form IV

| 2-Theta (°) | Relative Intensity (%) |
| --- | --- |
| 4.0 | 9.1 |
| 5.8 | 2.0 |

TABLE 4-continued

XRPD Peak Data for Compound 1 Crystalline Form IV

| 2-Theta (°) | Relative Intensity (%) |
|---|---|
| 6.5 | 12.6 |
| 7.4 | 58.7 |
| 8.0 | 2.7 |
| 8.6 | 2.4 |
| 11.9 | 4.3 |
| 12.3 | 48.2 |
| 13.7 | 14.8 |
| 14.8 | 91.6 |
| 15.6 | 30.5 |
| 16.0 | 33.9 |
| 16.7 | 16.8 |
| 17.4 | 36.6 |
| 18.6 | 24.5 |
| 18.9 | 100 |
| 19.8 | 56.4 |
| 20.4 | 16.2 |
| 21.2 | 18.4 |
| 21.3 | 13.5 |
| 22.6 | 24.3 |
| 23.5 | 8.7 |
| 24.2 | 41.2 |
| 24.9 | 18.4 |
| 25.8 | 17.8 |
| 26.8 | 3.7 |
| 27.5 | 10.3 |
| 28.7 | 2.2 |
| 29.3 | 5.6 |

DSC analysis of Compound 1 crystalline Form IV revealed one endothermic peak with an onset temperature of 31.8° C. and a maximum at 62.4° C. and a second endothermic peak with an onset temperature of 135.3° C. and a maximum at 145.8° C. The DSC thermogram of Compound 1 crystalline Form IV is provided in FIG. 11.

TGA analysis of Compound 1 crystalline Form IV revealed 5.4% weight loss below 100° C. It decomposes above 140° C. The TGA thermogram of Compound 1 crystalline Form IV is provided in FIG. 12.

Example 5. Preparation of the Compound 1 Crystalline THF Solvate Form (Form V) from Amorphous Compound 1

In a 250 mL round bottom flask equipped with a magnetic stirring bar was placed amorphous (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid (amorphous Compound 1, 10.0 g, 14.41 mmol) in THF (90 mL) and MeOH (10 mL) at room temperature. The mixture was heated to 35° C. to provide a solution. After removal of most of the solvents under reduced pressure, THF (100 mL) was added to provide a solution. The resulting solution was distilled to 37 grams, and the concentrated solution was left at room temperature without agitation. Solids were gradually precipitated out, which were collected by filtration after 24 hours. THF (20 mL) was used to transfer and rinse the solids. The wet cake was dried on the filter for 5 minutes to provide the desired product, (R)-1-((7-cyano-2-(3'-((3-(((R)-3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)pyrrolidine-3-carboxylic acid (Compound 1, 9.79 g, 84.3% yield), as a yellow to light brown beads-like solid, which contained 13.9 wt % of THF and was confirmed to be another meta-stable crystalline THF solvate form. This meta-stable beads-like crystalline THF solvate form has been designated as Form V.

Form V solid was confirmed as a crystalline solid according to XRPD analysis. The XRPD pattern of Compound 1 crystalline Form V is shown in FIG. 13 and the peak data of Compound 1 crystalline Form V is provided in Table 5.

TABLE 5

XRPD Peak Data for Compound 1 Crystalline Form V

| 2-Theta (°) | Relative Intensity (%) |
|---|---|
| 5.8 | 100 |
| 6.8 | 9.1 |
| 8.0 | 14.0 |
| 10.2 | 0.7 |
| 11.1 | 11.6 |
| 11.7 | 3.6 |
| 12.5 | 11.5 |
| 13.6 | 3.7 |
| 14.3 | 1.2 |
| 15.1 | 31.0 |
| 15.3 | 23.1 |
| 16.3 | 28.7 |
| 17.0 | 43.5 |
| 17.4 | 16.1 |
| 18.0 | 24.0 |
| 18.3 | 46.2 |
| 18.9 | 53.5 |
| 19.4 | 13.0 |
| 19.7 | 16.9 |
| 20.0 | 18.9 |
| 20.7 | 31.6 |
| 21.7 | 44.6 |
| 22.2 | 11.3 |
| 22.9 | 23.3 |
| 24.2 | 12.8 |
| 24.7 | 7.2 |
| 24.9 | 5.5 |
| 25.6 | 16.0 |
| 26.0 | 5.2 |
| 26.3 | 3.8 |
| 27.2 | 5.5 |
| 28.5 | 13.6 |

DSC analysis of Compound 1 crystalline Form V revealed one endothermic peak with an onset temperature of 23.8° C. and a maximum at 48.5° C. and a second endothermic peak with an onset temperature of 114.0° C. and a maximum at 117.9° C. The DSC thermogram of Compound 1 crystalline Form V is provided in FIG. 14.

TGA analysis of Compound 1 crystalline Form V revealed 4.3% weight loss below 100° C. and 7.4% weight loss between 100° C. and 155° C. It decomposes above 160° C. The TGA thermogram of Compound 1 crystalline Form V is provided in FIG. 15.

Form I is a non-solvate and non-hydrate crystalline form and it is the thermodynamically most crystalline form under the conditions investigated to date. Form II is a stable THF solvate and it can be generated from Form I in the THF-containing solvent systems and is readily converted to Form I after removal THF by either drying or slurry in solvent(s). The other three meta-stable crystalline forms, including the meta-stable THF solvate forms, Form III and Form V, and the meta-stable non-solvate crystalline form (Form IV), are also readily converted into the most stable, non-solvate and non-hydrate crystalline form, Form I, through the formation of the stable crystalline THF solvate form (Form II) followed by de-solvation.

Example 6. Conversion of Form III, IV, and V to Form II

Conversion of these three crystalline forms (Form III, Form IV, and Form V) to Form II follows the similar process conditions discovered and developed for conversion of the amorphous powder to the stable crystalline THF solvate form (Form II). A suspension of amorphous Compound 1 powder, the meta-stable THF solvates of crystalline Compound 1 solid (Form III or Form V), or the meta-stable non-solvate of crystalline Compound 1 solid (Form IV) in THF or a mixture of THF and MeOH was heated to 45-55° C. to generate a clear solution. The volumes of the solvent(s) and/or ratio of the solvent composition utilized for dissolution were varied depending on the solid state (amorphous or crystalline form) and the solvent system utilized. The solution was polish filtered at 40-50° C. before being gradually cooled to ambient temperature. The Form I seeds (1-2 wt %) were then added into the solution at 20-35° C. to induce the crystallization. The mixture was then agitated at ambient temperature for 2-3 hours before an anti-solvent, such as isopropyl acetate (IPAc), was added. The resulting suspension was continued to agitate at ambient temperature for 1-24 hours. The solids were collected by filtration and the wet cake was confirmed to be Form II, a stable crystalline THF solvate, by the X-ray powder diffraction (XRPD) analysis.

In addition, a mixture of the meta-stable THF solvates of crystalline Compound 1 solid (Form V, 105.5 mg) and the non-solvate and non-hydrate crystalline form (Form I, 108.8 mg) slurry in a mixture of THF and MeOH (9:1 by volume, 2 mL) was stirred at ambient temperature for two days. The wet cake collected by filtration was confirmed to be Form II, a stable crystalline THF solvate, by the X-ray powder diffraction (XRPD) analysis.

Similarly, a mixture of the meta-stable non-solvate of crystalline Compound 1 solid (Form IV, 100.5 mg) and the non-solvate and non-hydrate crystalline form (Form I, 102.3 mg) slurry in a mixture of THF and MeOH (9:1 by volume, 2 mL) was stirred at ambient temperature for two days. The wet cake collected by filtration was confirmed to be Form II, a stable crystalline THF solvate, by the X-ray powder diffraction (XRPD) analysis.

Example 7. Conversion of Form II to Form I

Conversion of Form II, the stable crystalline THF solvate form, to Form I, the most stable non-solvate and non-hydrate crystalline form, is achieved by removal of THF through either drying or slurry in solvent(s). This de-solvation process can be done either at atmosphere or under reduced pressure. After drying either at ambient temperature or at the elevated temperature, the wet cake of Form II loses THF and the corresponding non-solvate non-hydrate crystalline form (Form I) is gradually generated.

The typical drying process can effectively remove THF to 0.5-1.0 wt %. At this level, almost no Form II patterns can be detected in the XRPD analysis. However, it does not meet the residual solvent requirement established for pharmaceutical use. Therefore, a slurry protocol was developed to remove the residual THF 1 wt %) from the remaining trace amount of Form II crystals.

A suspension of the pre-dried Form II cake, which typically contains less than 1.0 wt % of THE, in an aqueous acetone is heated to 45-55° C. and agitated at 45-55° C. for 1-5 hours. After cooling to 15-25° C., the solids are collected by filtration, washed with acetone, and dried in a vacuum oven at 45° C. under reduced pressure with a gentle nitrogen sweeping for 8-12 hours. The dried desired product is a pure crystalline Form I which typically contains less than 200 ppm of the residual THE.

Example 8. Conversion of Form I to Form II

Form II of Compound 1 crystalline solids can be readily obtained by re-slurrying the Form I crystals in a THF-containing solvent system. Thus, a suspension of Compound 1 Form I crystals (0.1 g) in THF (0.5 mL) and IPAc (2 mL) was heated to 55° C. and agitated at 55° C. for 1 hour. The solids were collected by filtration and the wet cake was determined to be exclusively the crystalline Form II, which contained 42% of THE.

Figure 16:
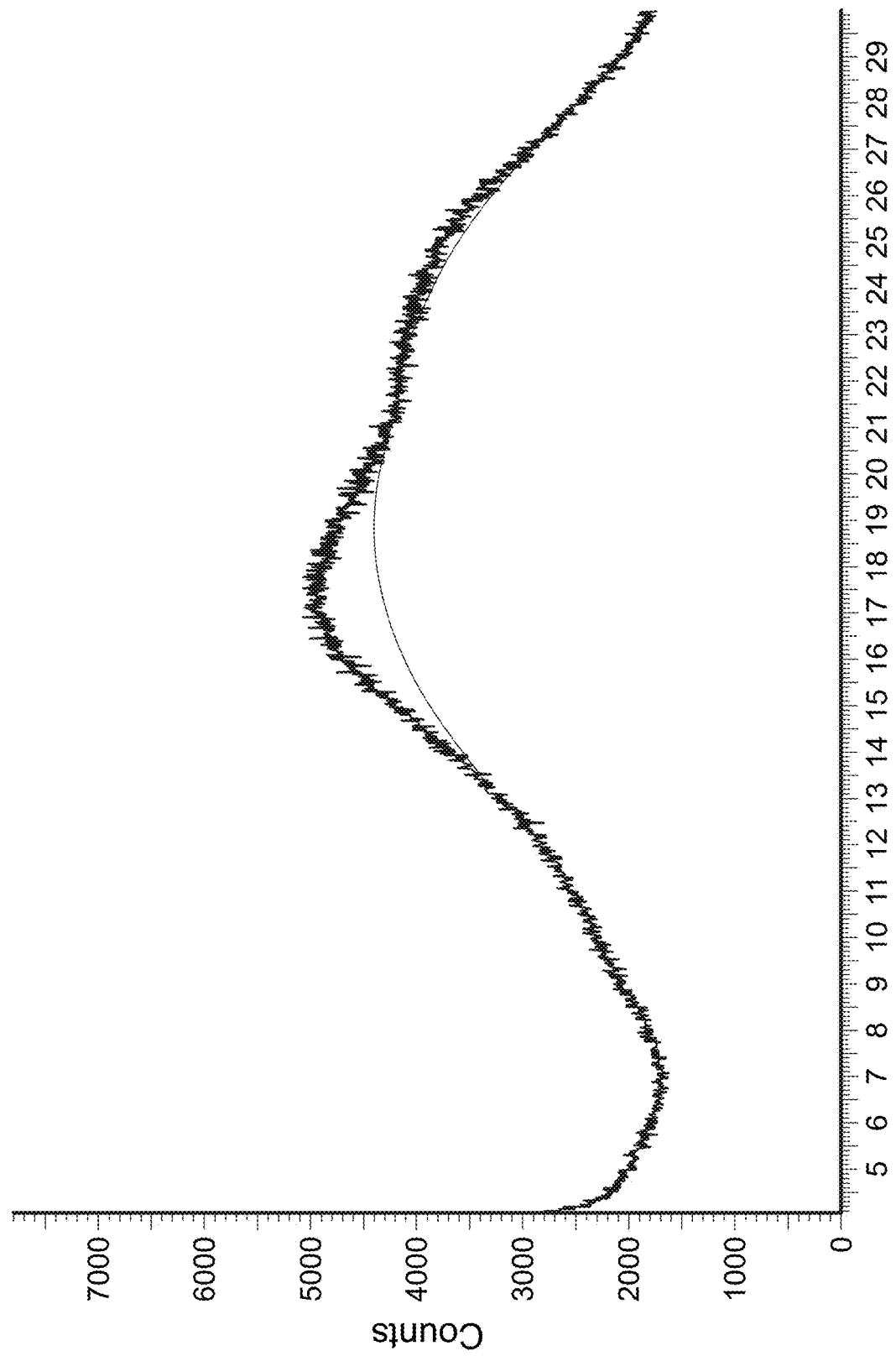
FIG. 16 shows an XRPD pattern of the amorphous powder of Compound 1.

Under the selected process conditions, all the crystalline forms (Form I, Form II, Form III, Form IV, and Form V) can be converted into the corresponding amorphous Compound 1. The amorphous powder was confirmed as an amorphous solid according to XRPD analysis. The XRPD pattern of Compound 1 amorphous powder is shown in FIG. 16. It is a signature amorphous halo and contains no crystalline powder pattern and no crystalline diffraction peaks.

Figure 17:
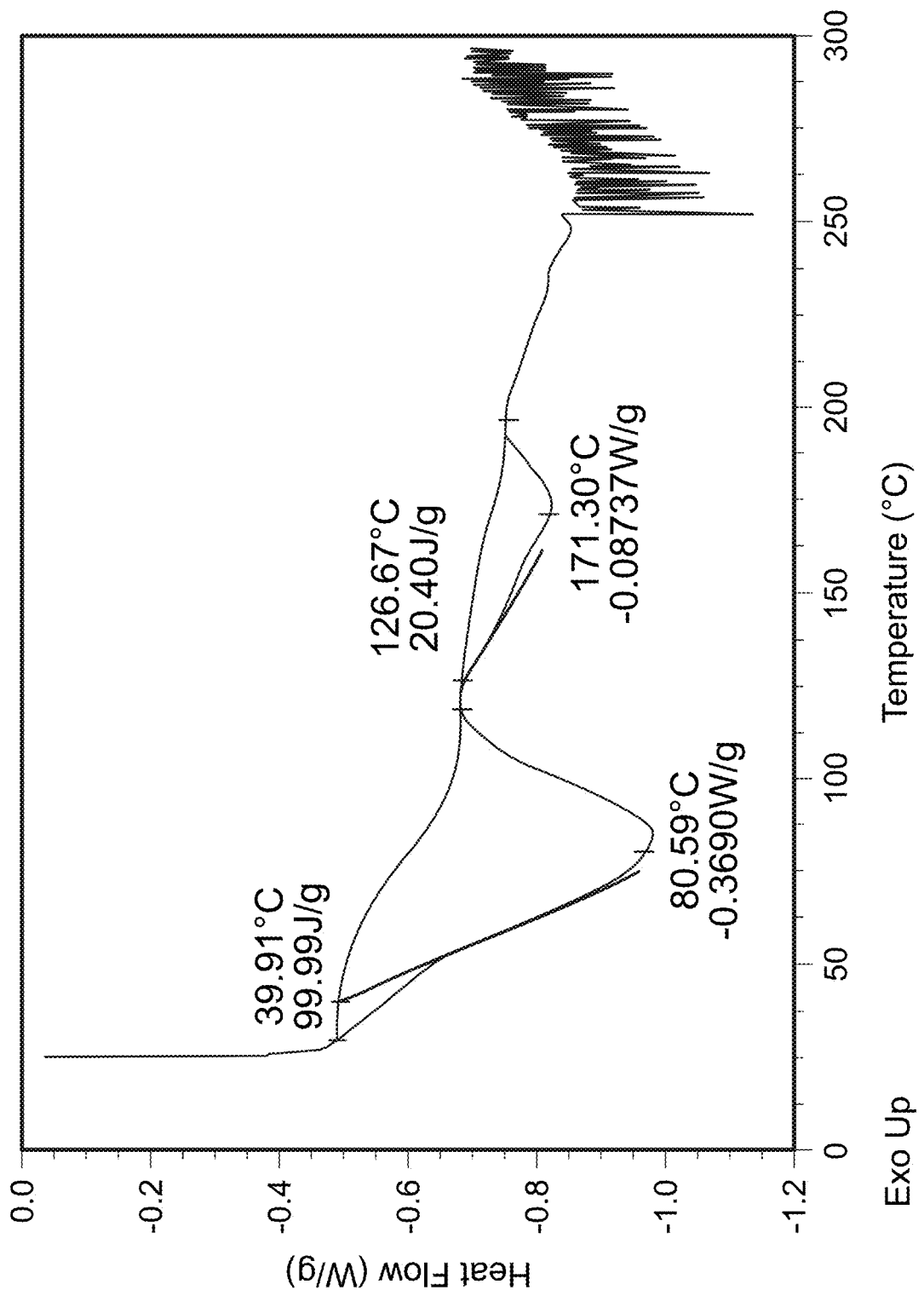
FIG. 17 shows a DSC thermogram of amorphous powder of Compound 1.

DSC analysis of Compound 1 amorphous powder revealed one endothermic peak with an onset temperature of 39.9° C. and a maximum at 80.6° C. and a second endothermic peak with an onset temperature of 126.7° C. and a maximum at 171.3° C. The DSC thermogram of Compound 1 amorphous powder is provided in FIG. 17.

Figure 18:
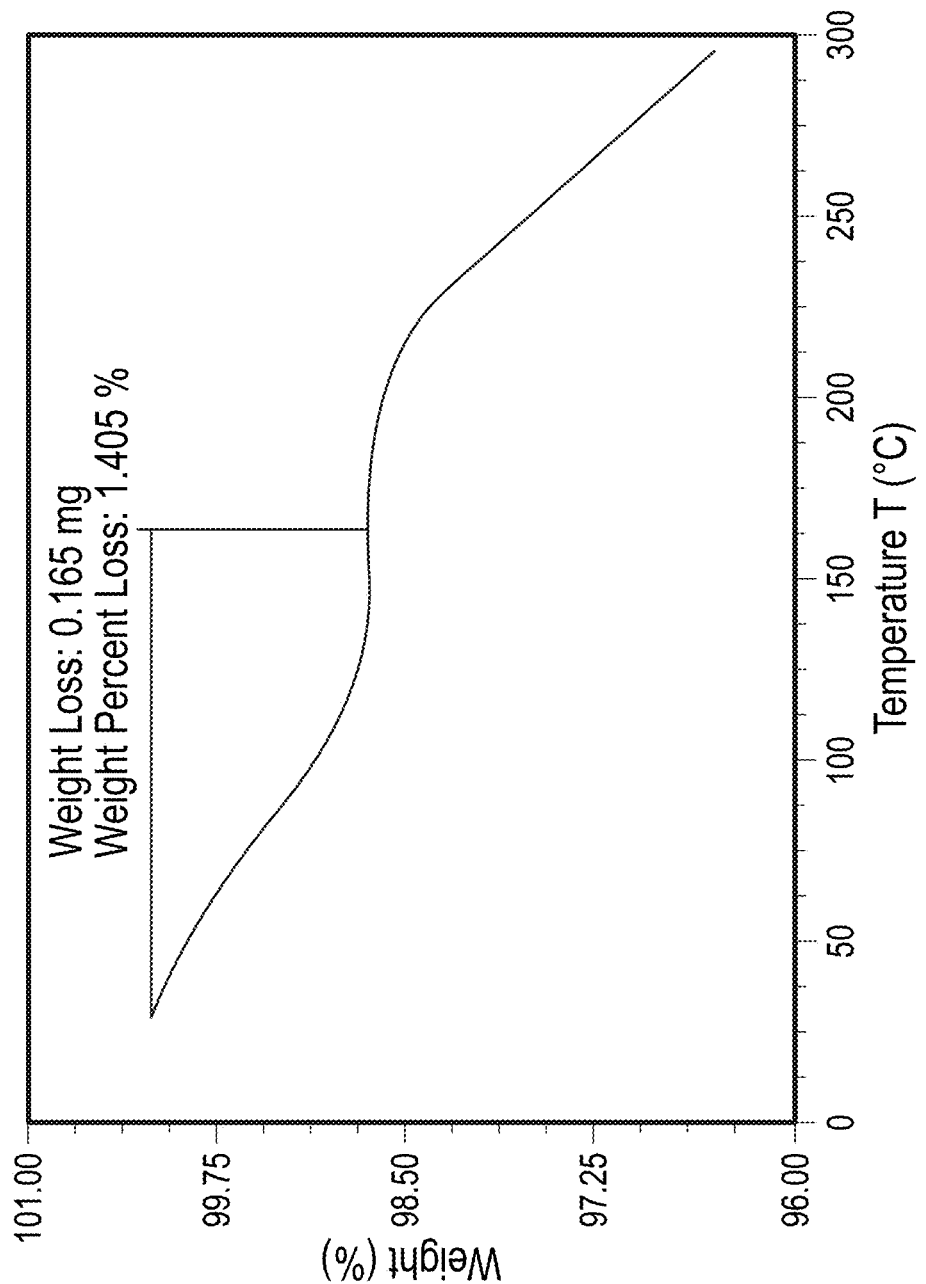
FIG. 18 shows a TGA thermogram of amorphous powder of Compound 1.
Figure 19:
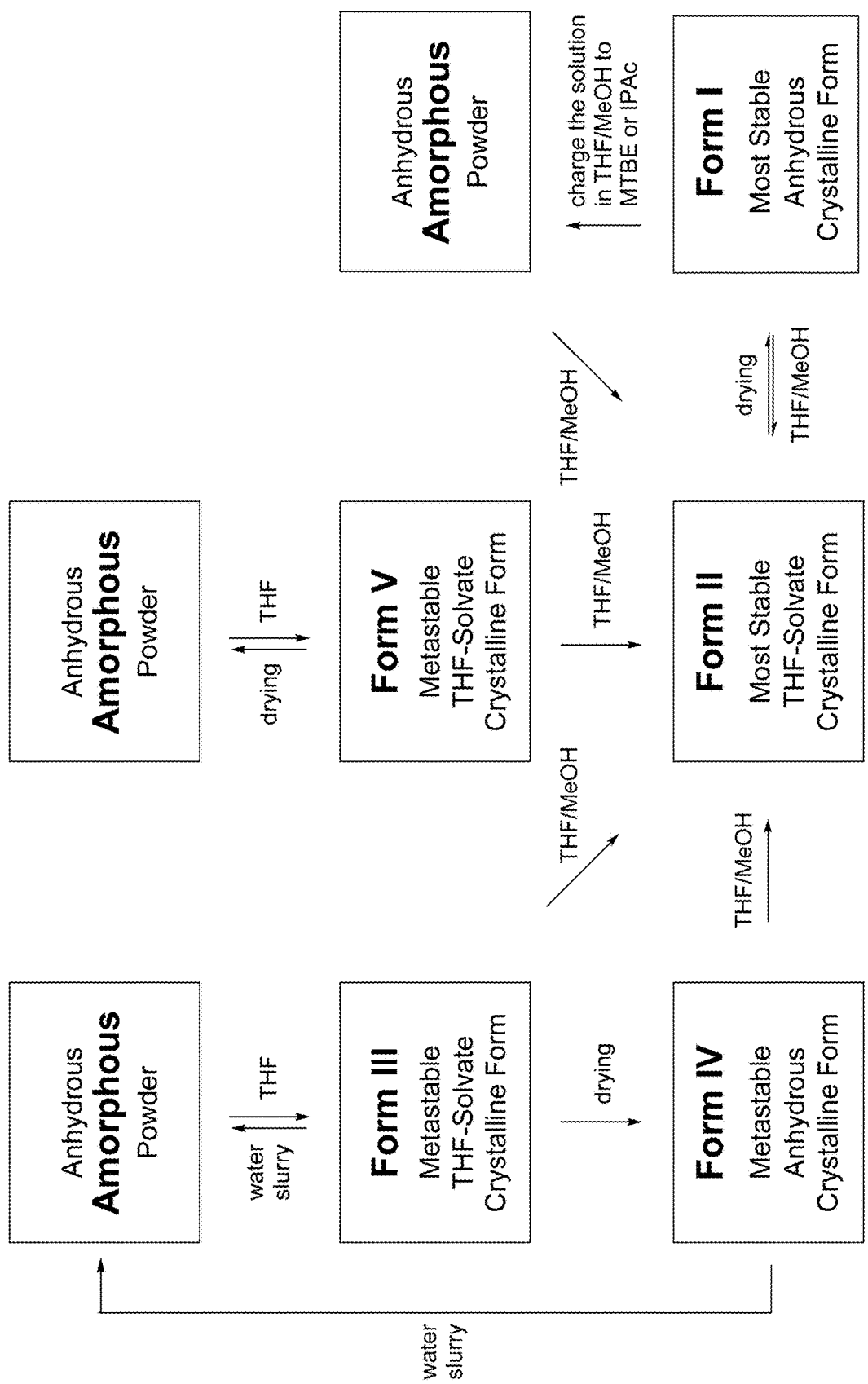
FIG. 19 shows the relationship and interconversion of Compound 1 amorphous powder and various crystalline forms.

TGA analysis of Compound 1 amorphous powder revealed 1.4% weight loss below 165° C. It decomposes above 170° C. The TGA thermogram of Compound 1 amorphous powder is provided in FIG. 18.

Example 9. Conversion of the Most Stable Non-Solvate and Non-Hydrate Compound 1 Crystalline Form (Form I) to Compound 1 Amorphous Powder Through the Stable Compound 1 Crystalline THF Solvate Form (Form II)

A suspension of the Compound 1 Form I crystals (1.06 g) in THF (36 mL) and MeOH (4 mL) was heated to 60° C. to provide a clear solution. The solution was distilled to about 9 mL at 1 atmosphere. The resulting concentrated solution was then added to a cold solution of IPAc (35 mL) at 0-5° C. in 15 minutes. After agitated at 0-5° C. for 30 minutes, the solids were collected by filtration, dried on the filter funnel to provide the desired product, Compound 1 (0.94 g, 90% yield), as a yellow amorphous powder.

Example 10. Conversion of the Meta-Stable Compound 1 Crystalline THF Solvate Form (Form III) to Compound 1 Amorphous Powder Through the Meta-Stable Non-Solvate Compound 1 Crystalline Form (Form IV)

The wet cake of the meta-stable crystalline THF solvate form (Form III) on the filter was dried at ambient temperature for 22 hours. The THF content was reduced from 5.9 wt % to approximately 0.5 wt % and the crystalline form was changed to the non-solvate crystalline form (Form IV). Water (2 g) was then added to the crystalline Form IV solids (1.0 g) on the filter funnel under house vacuum. After drying on the filter at ambient temperature for 12-24 hours, the Form IV crystals was completely converted into the amorphous powder.

Example 11. Conversion of the Meta-Stable Compound 1 Crystalline THF Solvate Form (Form V) to Compound 1 Amorphous Powder The wet cake of the Compound 1 Form V crystals was dried on the filter first followed by in a vacuum oven at 65° C. under house vacuum with a gentle nitrogen sweeping for four days. The desired product, Compound 1, was obtained as a light yellow to yellow amorphous powder. In this amorphous powder, no residual THF was detected.

Example A. PD-1/PD-L1 Homogeneous Time-Resolved Fluorescence (HTHF) Binding Assay The assays are conducted in a standard black 384-well polystyrene plate with a final volume of 20 μL. Inhibitors are first serially diluted in DMSO and then added to the plate wells before the addition of other reaction components. The final concentration of DMSO in the assay are 1%. The assays are carried out at 25° C. in the PBS buffer (pH 7.4) with 0.05% Tween-20 and 0.1% BSA. Recombinant human PD-L1 protein (19-238) with a His-tag at the C-terminus are purchased from AcroBiosystems (PD1-H5229). Recombinant human PD-1 protein (25-167) with Fc tag at the C-terminus are purchased from AcroBiosystems (PD1-H5257). PD-L1 and PD-1 proteins are diluted in the assay buffer and 10 μL are added to the plate well. Plates are centrifuged and proteins are preincubated with inhibitors for 40 minutes. The incubation is followed by the addition of 10 μL of HTHF detection buffer supplemented with Europium cryptate-labeled anti-human IgG (PerkinElmer-AD0212) specific for Fc and anti-His antibody conjugated to SureLight®-Allophycocyanin (APC, PerkinElmer-AD0059H). After centrifugation, the plate is incubated at 25° C. for 60 min. before reading on a PHERAstar FS plate reader (665 nm/620 nm ratio). Final concentrations in the assay are—3 nM PD1, 10 nM PD-L1, 1 nM europium anti-human IgG and 20 nM anti-His-Allophycocyanin. $IC_{50}$ determination are performed by fitting the curve of percent control activity versus the log of the inhibitor concentration using the GraphPad Prism 5.0 software.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A crystalline form of Compound 1:

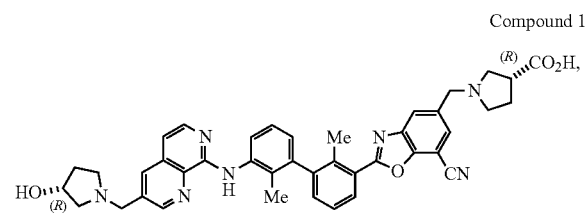

Compound 1 wherein the form is non-solvated, and the form is:

Form I, which has at least one XRPD peak, in terms of 2-theta (±0.2 degrees), selected from 4.5, 7.9, 10.8, 13.1, 15.0, 17.3, 18.0, 20.8, 21.7, and 25.3 degrees; or Form IV, which has at least one XRPD peak, in terms of 2-theta (±0.2 degrees), selected from 6.5, 7.4, 12.3, 14.8, 17.4, 18.9, 19.8, and 24.2 degrees.

2. The crystalline form of claim 1, having Form I, wherein the form has at least four XRPD peaks, in terms of 2-theta (±0.2 degrees), selected from 4.5, 7.9, 10.8, 13.1, 15.0, 17.3, 18.0, 20.8, 21.7, and 25.3 degrees.

3. The crystalline form of claim 1, having Form I, wherein the form has at least one XRPD peak, in terms of 2-theta (±0.2 degrees), selected from 4.5, 7.9, 10.8, 13.1, 15.0, 17.3, and 20.8 degrees.

4. The crystalline form of claim 1, having Form I, wherein the form has at least four XRPD peaks, in terms of 2-theta (±0.2 degrees), selected from 4.5, 7.9, 10.8, 13.1, 15.0, 17.3, and 20.8 degrees.

5. The crystalline form of claim 1, having Form I, wherein the form has an XRPD pattern as substantially shown in FIG. 1.

6. The crystalline form of claim 1, having Form I, which has a first endothermic peak with an onset temperature (±3° C.) at 23° C. and a maximum at 98° C. and a second endothermic peak with an onset temperature (±3° C.) at 147° C. and a maximum at 159° C. in a DSC thermogram.

7. The crystalline form of claim 1, having Form I, wherein the form has a DSC thermogram substantially as shown in FIG. 2.

8. The crystalline form of claim 1, having Form I, wherein the form has a TGA thermogram substantially as shown in FIG. 3.

9. The crystalline form of claim 1, having Form IV, wherein the form has at least four XRPD peaks, in terms of 2-theta (±0.2 degrees), selected from 6.5, 7.4, 12.3, 14.8, 17.4, 18.9, 19.8, and 24.2 degrees.

10. The crystalline form of claim 1, having Form IV, which has a first endothermic peak with an onset temperature (±3° C.) at 31° C. and a maximum at 62° C. and a second endothermic peak with an onset temperature (±3° C.) at 135° C. and a maximum at 145° C. in a DSC thermogram.

11. A crystalline form of Compound 1:

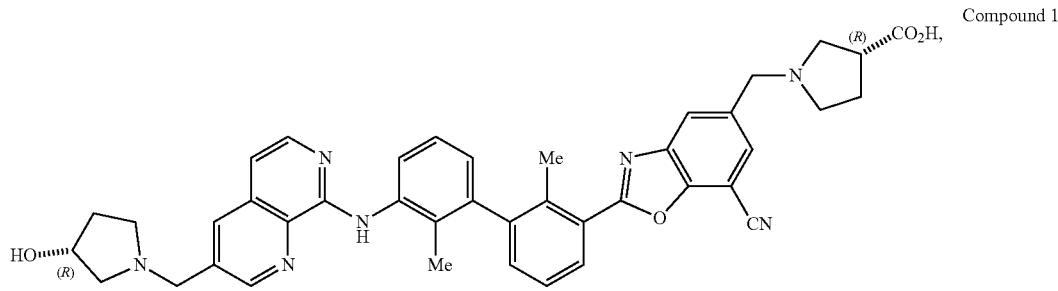

Compound 1 or a solvate thereof, wherein the form is a tetrahydrofuran solvate, and the form is:

Form II, which has at least one XRPD peak, in terms of 2-theta (±0.2 degrees), selected from 7.5, 9.9, 12.8, 13.4, 14.4, 15.0, 17.1, 19.8, and 23.3 degrees;

Form III, which has at least one XRPD peak, in terms of 2-theta (±0.2 degrees), selected from 5.9, 8.0, 12.6, 15.1, 17.0, 18.4, and 18.9 degrees; or Form V, which has at least one XRPD peak, in terms of 2-theta (±0.2 degrees), selected from 5.8, 8.0, 12.5, 15.1, 16.3, 17.0, 18.3, 18.9, 20.7, and 21.7 degrees.

12. The crystalline form of claim 11, having Form II, wherein the form has at least four XRPD peaks, in terms of 2-theta (±0.2 degrees), selected from 7.5, 9.9, 12.8, 13.4, 14.4, 15.0, 17.1, 19.8, and 23.3 degrees.

13. The crystalline form of claim 11, having Form II, which has a first endothermic peak with an onset temperature (±3° C.) at 68° C. and a maximum at 95° C. and a second endothermic peak with an onset temperature (±3° C.) at 153° C. and a maximum at 165° C. in a DSC thermogram.

14. The crystalline form of claim 11, having Form III, wherein the form has at least four XRPD peaks, in terms of 2-theta (±0.2 degrees), selected from 5.9, 8.0, 12.6, 15.1, 17.0, 18.4, and 18.9 degrees.

15. The crystalline form of claim 11, having Form III, which has a first endothermic peak with an onset temperature (±3° C.) at 23° C. and a maximum at 56° C. and a second endothermic peak with an onset temperature (±3° C.) at 106° C. and a maximum at 122° C. in a DSC thermogram.

16. The crystalline form of claim 11, having Form V, wherein the form has at least four XRPD peaks, in terms of 2-theta (±0.2 degrees), selected from 5.8, 8.0, 12.5, 15.1, 16.3, 17.0, 18.3, 18.9, 20.7, and 21.7 degrees.

17. The crystalline form of claim 11, having Form V, which has a first endothermic peak with an onset temperature (±3° C.) at 23° C. and a maximum at 48° C. and a second endothermic peak with an onset temperature (±3° C.) at 113° C. and a maximum at 117° C. in a DSC thermogram.

18. A pharmaceutical composition comprising a crystalline form of claim 1, and a pharmaceutically acceptable carrier or excipient.

19. A solid oral dosage form comprising the pharmaceutical composition of claim 18.

20. A process of preparing the crystalline form of claim 1,

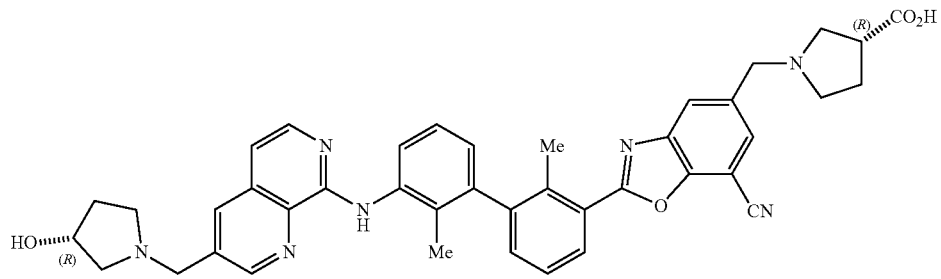

which is Form I, comprising converting a tetrahydrofuran solvate of Compound 1 to said Form I.

21. The process of claim 20, wherein the tetrahydrofuran solvate is Form II of Compound 1, wherein Form II has at least one XRPD peak, in terms of 2-theta (±0.2 degrees), selected from 7.5, 9.9, 12.8, 13.4, 14.4, 15.0, 17.1, 19.8, and 23.3 degrees.

22. The process of claim 20, wherein the converting comprises slurrying the Form II in a solvent component to form the Form I, wherein Form II has at least one XRPD peak, in terms of 2-theta (±0.2 degrees), selected from 7.5, 9.9, 12.8, 13.4, 14.4, 15.0, 17.1, 19.8, and 23.3 degrees.

23. The process of claim 22, wherein the slurrying comprises preparing a suspension comprising the Form II and a solvent component.

24. The process of claim 22, wherein the slurrying comprises preparing a suspension comprising the Form II and a solvent component; heating the suspension to a temperature of about 35° C. to about 70° C.; and after said heating, cooling the suspension to a temperature of about 15° C. to about 25° C. to form the Form I as a solid; wherein the solvent component comprises acetone and water.

25. The process of claim 20, wherein the converting comprises drying the Form II to form the Form I, wherein Form II has at least one XRPD peak, in terms of 2-theta (±0.2 degrees), selected from 7.5, 9.9, 12.8, 13.4, 14.4, 15.0, 17.1, 19.8, and 23.3 degrees.

26. A process of preparing the crystalline, tetrahydrofuran solvate of claim 11,

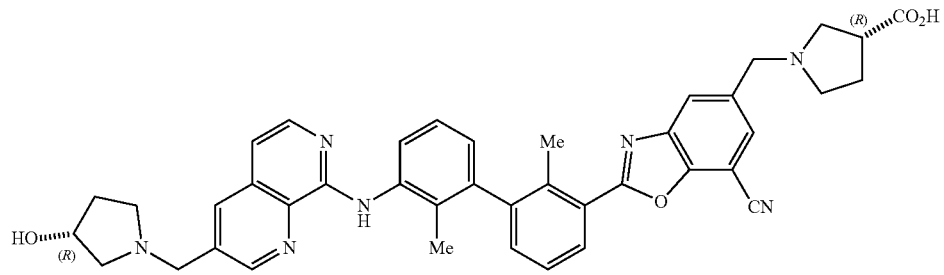

which is Form II,
comprising:
treating a solution comprising tetrahydrofuran and Compound 1 potassium salt:

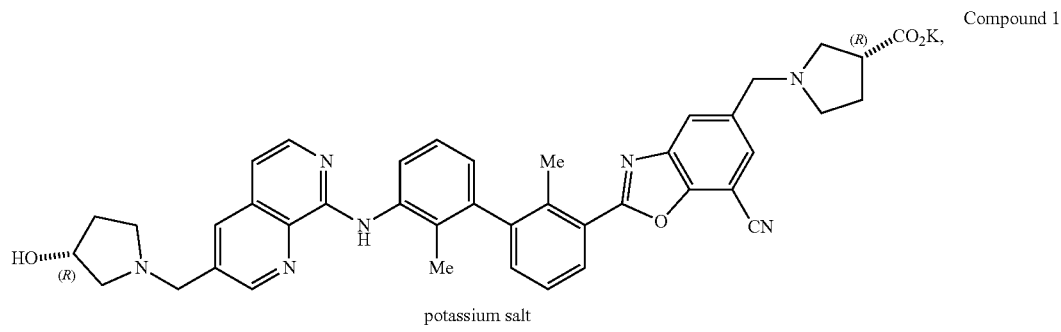

Compound 1 potassium salt with a metal scavenger or an ion exchange resin; and precipitating Form II of Compound 1.

27. The process of claim 26, wherein the treating comprises treating with the metal scavenger and the ion exchange resin.

28. The process of claim 26, wherein the solution further comprises a $C_{1-6}$ alcohol, and wherein the $C_{1-6}$ alcohol comprises methanol.

29. The process of claim 26 about 55° C.; after said cooling, filtering the solution and concentrating filtrate; and after concentrating said filtrate, adding seed crystals of Form I to said concentrated filtrate to provide a suspension.

30. The process of claim 29, further comprising adding a solvent component to the suspension.

31. The process of claim 29, further comprising adding a solvent component to the suspension, wherein the solvent component is isopropyl acetate.

32. A process of preparing the crystalline, tetrahydrofuran solvate of claim 11, which is Form II, comprising converting Form III, Form IV, or Form V of the compound to Form II in the presence of a solvent component comprising tetrahydrofuran;

wherein Form IV has at least one XRPD peak, in terms of 2-theta (±0.2 degrees), selected from 6.5, 7.4, 12.3, 14.8, 17.4, 18.9, 19.8, and 24.2 degrees.

33. The process of claim 32, wherein the converting comprises preparing a suspension of Form III, Form IV, or Form V in the solvent component; heating the suspension to provide a solution; after said heating, cooling the solution; after said cooling, adding seed crystals of Form I to the cooled solution to provide a seeded suspension; and adding an anti-solvent to the seeded suspension.

34. The process of claim 32, wherein the converting comprises preparing a suspension of Form III, Form IV, or Form V in the solvent component; heating the suspension to a temperature of about 35° C. to about 70° C. to provide a solution; after said heating, cooling the solution to about ambient temperature; after said cooling, adding seed crystals

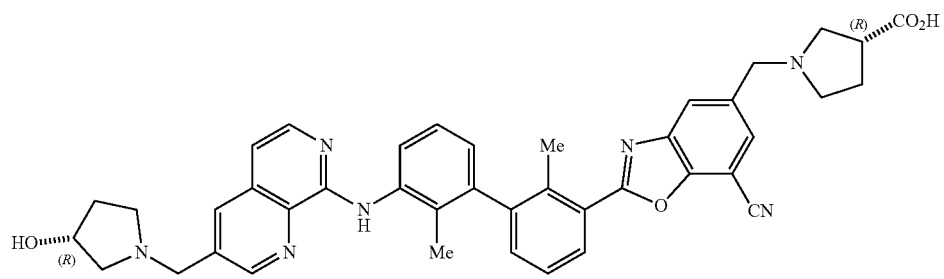

Form I to the cooled solution to provide a seeded suspension; and adding an anti-solvent component to the seeded suspension.

36. The process of claim 32, wherein the solvent component comprises tetrahydrofuran or a mixture of tetrahydrofuran and methanol.

35. The process of claim 33, wherein the anti-solvent component comprises isopropyl acetate.

37. A process of preparing an amorphous form of Compound 1:

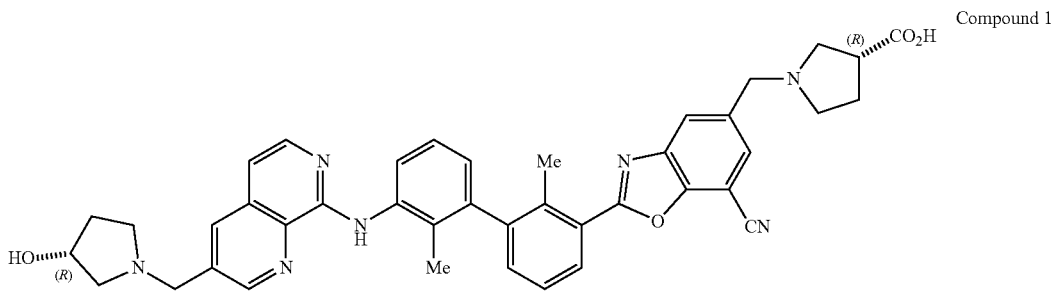

Compound 1 comprising converting Form I of Compound 1 to said amorphous form of Compound 1, wherein Form I has at least one XRPD peak, in terms of 2-theta (±0.2 degrees), selected from 4.5, 7.9, 10.8, 13.1, 15.0, 17.3, 18.0, 20.8, 21.7, and 25.3 degrees.

38. The process of claim 37, wherein the converting comprises preparing a suspension of the Form I of Compound 1 in a solvent component; heating the suspension to a temperature of about 40° C. to about 80° C. to form a solution; after said heating, concentrating the solution; after said concentrating, adding the solution to a cold anti-solvent component at a temperature of about −10° C. to about 15° C. to form a suspension of the amorphous form of Compound 1.

39. The process of claim 38, wherein the solvent component comprises tetrahydrofuran and methanol.

40. The process of claim 38, wherein the cold anti-solvent component comprises isopropyl acetate.

41. A method of inhibiting PD-1/PD-L1 interaction, said method comprising administering to a patient a crystalline form of claim 1.

42. A method of treating a disease or disorder associated with inhibition of PD-1/PD-L1 interaction, said method comprising administering to a patient in need thereof a therapeutically effective amount of a crystalline form of claim 1, wherein the disease or disorder is cancer, selected from a metastatic cancer that expresses PD-L1, small cell lung cancer, non-small cell lung cancer, hepatic cancer, hepatocellular carcinoma, melanoma, cancer of the bladder, cancer of the urethra, renal cancer, clear cell renal carcinoma, and cutaneous squamous cell carcinoma.

43. A pharmaceutical composition comprising a crystalline form of claim 11, and a pharmaceutically acceptable carrier or excipient.

44. A solid oral dosage form comprising the pharmaceutical composition of claim 43.

45. A method of inhibiting PD-1/PD-L1 interaction, said method comprising administering to a patient a crystalline form of claim 11.

46. A method of treating a disease or disorder associated with inhibition of PD-1/PD-L1 interaction, said method comprising administering to a patient in need thereof a therapeutically effective amount of a crystalline form of claim 11, wherein the disease or disorder is cancer, selected from a metastatic cancer that expresses PD-L1, small cell lung cancer, non-small cell lung cancer, hepatic cancer, hepatocellular carcinoma, melanoma, cancer of the bladder, cancer of the urethra, renal cancer, clear cell renal carcinoma, and cutaneous squamous cell carcinoma.

* * * * *

UNITED STATES PATENT AND TRADEMARK OFFICE
CERTIFICATE OF CORRECTION

PATENT NO. : 11,760,756 B2  
APPLICATION NO. : 17/520264  
DATED : September 19, 2023  
INVENTOR(S) : Zhongjiang Jia et al.

Page 1 of 1

It is certified that error appears in the above-identified patent and that said Letters Patent is hereby corrected as shown below:

In the Claims

Column 80, Line 52, Claim 34, after "crystals" insert -- of --.

Signed and Sealed this
Fifth Day of March, 2024

Katherine Kelly Vidal
*Director of the United States Patent and Trademark Office*